(12) United States Patent
Man et al.

(10) Patent No.: US 7,887,641 B2
(45) Date of Patent: Feb. 15, 2011

(54) NEUTRAL OR ALKALINE MEDIUM CHAIN PEROXYCARBOXYLIC ACID COMPOSITIONS AND METHODS EMPLOYING THEM

(75) Inventors: Victor Fuk-Pong Man, St. Paul, MN (US); Gina Marie Fasching, Eden Prairie, MN (US); Nathan Daniel Peitersen, Richfield, MN (US); Mark Raymond Altier, Mendota Heights, MN (US)

(73) Assignee: Ecolab USA Inc., St. Paul, MN (US)

( * ) Notice: Subject to any disclaimer, the term of this patent is extended or adjusted under 35 U.S.C. 154(b) by 1010 days.

(21) Appl. No.: 11/181,257

(22) Filed: Jul. 14, 2005

(65) Prior Publication Data
US 2006/0113506 A1    Jun. 1, 2006

Related U.S. Application Data

(63) Continuation-in-part of application No. 11/030,641, filed on Jan. 4, 2005, and a continuation-in-part of application No. 11/030,271, filed on Jan. 4, 2005, now Pat. No. 7,498,051, and a continuation-in-part of application No. 11/029,235, filed on Jan. 4, 2005, now Pat. No. 7,504,124, and a continuation-in-part of application No. 11/030,233, filed on Jan. 4, 2005, now abandoned, and a continuation-in-part of application No. 10/754,426, filed on Jan. 9, 2004, and a continuation-in-part of application No. 10/754,396, filed on Jan. 9, 2004, now Pat. No. 7,504,123, and a continuation-in-part of application No. 10/754,436, filed on Jan. 9, 2004, now Pat. No. 7,507,429, and a continuation-in-part of application No. 10/754,405, filed on Jan. 9, 2004.

(60) Provisional application No. 60/697,303, filed on Jul. 6, 2005.

(51) Int. Cl.
*B08B 3/00* (2006.01)
*C01B 15/10* (2006.01)

(52) U.S. Cl. .............................. 134/27; 134/28; 134/29; 134/34; 134/42; 134/3; 134/22.1; 134/22.11; 252/186.23; 252/186.26; 252/186.41

(58) Field of Classification Search .................... 134/27
See application file for complete search history.

(56) References Cited

U.S. PATENT DOCUMENTS 2,512,640 A    6/1950    Greenspan et al.

(Continued)

FOREIGN PATENT DOCUMENTS

CA    2181416    1/1997

(Continued)

OTHER PUBLICATIONS

"Emery® Fatty and Dibasic Acids Specifications and Characteristics", *Emery Industries*, Bulletin 145, (Oct. 1983).

(Continued)

*Primary Examiner*—Joseph D Anthony
(74) *Attorney, Agent, or Firm*—Andrew D. Sorensen; Laura C. DiLorenzo

(57) ABSTRACT

The present invention relates to medium chain peroxycarboxylic acid compositions of neutral or alkaline pH, to methods of making these compositions, and to methods employing these compositions. The methods include methods of cleaning. The compositions include cleaning compositions.

12 Claims, 7 Drawing Sheets

U.S. PATENT DOCUMENTS

| | | | |
|---|---|---|---|
| 3,122,417 A | 2/1964 | Blaser et al. | |
| 3,248,281 A | 4/1966 | Goodenough | |
| 3,350,265 A | 10/1967 | Rubinstein et al. | |
| 3,514,278 A | 5/1970 | Brink | |
| 3,895,116 A | 7/1975 | Herting et al. | |
| 3,929,678 A | 12/1975 | Laughlin et al. | |
| 3,996,386 A | 12/1976 | Malkki et al. | |
| 4,041,149 A | 8/1977 | Gaffar et al. | |
| 4,051,058 A | 9/1977 | Böwing et al. | |
| 4,051,059 A | 9/1977 | Böwing et al. | |
| 4,094,953 A | 6/1978 | Hadi et al. | |
| 4,129,517 A | 12/1978 | Eggensperger et al. | |
| 4,191,660 A | 3/1980 | Schreiber et al. | |
| 4,244,884 A | 1/1981 | Hutchins et al. | |
| 4,289,728 A | 9/1981 | Peel et al. | |
| 4,321,157 A | 3/1982 | Harris et al. | |
| 4,370,199 A | 1/1983 | Orndorff | |
| 4,404,040 A | 9/1983 | Wang | |
| 4,477,438 A | 10/1984 | Willcockson et al. | |
| 4,478,683 A | 10/1984 | Orndorff | |
| 4,501,681 A | 2/1985 | Groult et al. | |
| 4,521,375 A * | 6/1985 | Houlsby | 422/29 |
| 4,529,534 A | 7/1985 | Richardson | |
| 4,557,898 A | 12/1985 | Greene et al. | |
| 4,566,980 A | 1/1986 | Smith | |
| 4,591,565 A | 5/1986 | Branner-Jorgensen | |
| 4,592,488 A | 6/1986 | Simon et al. | |
| 4,613,452 A | 9/1986 | Sanderson | |
| 4,655,781 A * | 4/1987 | Hsieh et al. | 8/111 |
| 4,659,494 A | 4/1987 | Soldanski et al. | |
| 4,666,622 A | 5/1987 | Martin et al. | |
| 4,671,891 A * | 6/1987 | Hartman | 252/186.42 |
| 4,683,618 A | 8/1987 | O'Brien | |
| 4,695,290 A | 9/1987 | Kindig et al. | |
| 4,704,404 A | 11/1987 | Sanderson | |
| 4,715,980 A | 12/1987 | Lopes et al. | |
| 4,738,840 A | 4/1988 | Simon et al. | |
| 4,740,308 A | 4/1988 | Fremont et al. | |
| 4,753,033 A | 6/1988 | Kindig | |
| 4,802,994 A | 2/1989 | Mouché et al. | |
| 4,834,900 A | 5/1989 | Soldanski et al. | |
| 4,865,752 A | 9/1989 | Jacobs | |
| 4,900,721 A | 2/1990 | Bansemir et al. | |
| 4,906,617 A | 3/1990 | Jacquet et al. | |
| 4,908,306 A | 3/1990 | Lorincz | |
| 4,917,815 A | 4/1990 | Beilfuss et al. | |
| 4,923,677 A | 5/1990 | Simon et al. | |
| 4,937,066 A | 6/1990 | Vlock | |
| 4,943,414 A | 7/1990 | Jacobs et al. | |
| 4,945,110 A | 7/1990 | Brokken et al. | |
| 4,996,062 A | 2/1991 | Lehtonen et al. | |
| 4,997,571 A | 3/1991 | Roensch et al. | |
| 4,997,625 A | 3/1991 | Simon et al. | |
| 5,004,760 A | 4/1991 | Patton et al. | |
| 5,010,109 A | 4/1991 | Inoi | |
| 5,015,408 A | 5/1991 | Reuss | |
| 5,021,096 A | 6/1991 | Abadi | |
| 5,043,176 A | 8/1991 | Bycroft et al. | |
| 5,069,286 A | 12/1991 | Roensch et al. | |
| 5,078,896 A | 1/1992 | Rorig et al. | |
| 5,084,239 A | 1/1992 | Moulton et al. | |
| 5,093,140 A | 3/1992 | Watanabe | |
| 5,114,178 A | 5/1992 | Baxter | |
| 5,114,718 A | 5/1992 | Damani | |
| 5,122,538 A | 6/1992 | Lokkesmoe et al. | |
| 5,129,824 A | 7/1992 | Keller | |
| 5,130,124 A | 7/1992 | Merianos et al. | |
| 5,139,788 A | 8/1992 | Schmidt | |
| 5,168,655 A | 12/1992 | Davidson et al. | |
| 5,176,899 A | 1/1993 | Montgomery | |
| 5,184,471 A | 2/1993 | Losacco et al. | |
| 5,200,189 A * | 4/1993 | Oakes et al. | 424/405 |
| 5,208,057 A | 5/1993 | Greenley et al. | |
| 5,234,703 A | 8/1993 | Guthery | |
| 5,234,719 A | 8/1993 | Richter et al. | |
| 5,266,587 A | 11/1993 | Sankey et al. | |
| 5,268,003 A | 12/1993 | Coope et al. | |
| 5,269,962 A * | 12/1993 | Brodbeck et al. | 510/312 |
| 5,292,447 A | 3/1994 | Venturello et al. | |
| 5,306,350 A | 4/1994 | Hoy et al. | |
| 5,314,687 A | 5/1994 | Oakes et al. | |
| 5,320,805 A | 6/1994 | Kramer et al. | |
| 5,336,500 A | 8/1994 | Richter et al. | |
| 5,364,650 A | 11/1994 | Guthery | |
| 5,391,324 A | 2/1995 | Reinhardt et al. | |
| 5,409,633 A * | 4/1995 | Clements et al. | 252/186.42 |
| 5,409,713 A | 4/1995 | Lokkesmoe et al. | |
| 5,419,908 A | 5/1995 | Richter et al. | |
| 5,429,769 A * | 7/1995 | Nicholson et al. | 510/376 |
| 5,435,808 A | 7/1995 | Holzhauer et al. | |
| 5,436,008 A | 7/1995 | Richter et al. | |
| 5,437,868 A | 8/1995 | Oakes et al. | |
| 5,481,084 A | 1/1996 | Patrick et al. | |
| 5,489,434 A | 2/1996 | Oakes et al. | |
| 5,489,706 A | 2/1996 | Revell | |
| 5,494,588 A | 2/1996 | LaZonby | |
| 5,508,046 A | 4/1996 | Cosentino et al. | |
| 5,512,309 A | 4/1996 | Bender et al. | |
| 5,527,898 A | 6/1996 | Bauer et al. | |
| 5,545,343 A | 8/1996 | Brougham et al. | |
| 5,545,374 A | 8/1996 | French et al. | |
| 5,567,444 A | 10/1996 | Hei et al. | |
| 5,578,134 A | 11/1996 | Lentsch et al. | |
| 5,591,706 A | 1/1997 | Ploumen | |
| 5,595,967 A | 1/1997 | Miracle et al. | |
| 5,597,790 A | 1/1997 | Thoen | |
| 5,616,335 A | 4/1997 | Nicolle et al. | |
| 5,616,616 A | 4/1997 | Hall et al. | |
| 5,624,634 A | 4/1997 | Brougham et al. | |
| 5,632,676 A | 5/1997 | Kurschner et al. | |
| 5,641,530 A | 6/1997 | Chen | |
| 5,656,302 A | 8/1997 | Cosentino et al. | |
| 5,658,467 A | 8/1997 | LaZonby et al. | |
| 5,658,595 A | 8/1997 | Van Os | |
| 5,674,538 A | 10/1997 | Lokkesmoe et al. | |
| 5,674,828 A | 10/1997 | Knowlton et al. | |
| 5,683,724 A | 11/1997 | Hei et al. | |
| 5,692,392 A | 12/1997 | Swier | |
| 5,712,239 A | 1/1998 | Knowlton et al. | |
| 5,718,910 A | 2/1998 | Oakes et al. | |
| 5,720,983 A | 2/1998 | Malone | |
| 5,725,678 A | 3/1998 | Cannon et al. | |
| 5,741,767 A | 4/1998 | Nicholson et al. | |
| 5,756,139 A | 5/1998 | Harvey et al. | |
| 5,785,867 A * | 7/1998 | LaZonby et al. | 210/759 |
| 5,840,343 A | 11/1998 | Hall et al. | |
| 5,851,483 A | 12/1998 | Nicolle et al. | |
| 5,866,005 A | 2/1999 | DeSimone et al. | |
| 5,891,392 A | 4/1999 | Monticello et al. | |
| 5,900,256 A | 5/1999 | Scoville, Jr. et al. | |
| 5,902,619 A | 5/1999 | Rubow et al. | |
| 5,954,851 A | 9/1999 | Sakae | |
| 5,968,539 A | 10/1999 | Beerse et al. | |
| 5,989,611 A | 11/1999 | Stemmler, Jr. et al. | |
| 5,993,562 A | 11/1999 | Roelofs | |
| 5,998,358 A | 12/1999 | Herdt et al. | |
| 6,008,405 A | 12/1999 | Gray et al. | |
| 6,010,729 A | 1/2000 | Gutzmann et al. | |
| 6,024,986 A | 2/2000 | Hei | |
| 6,028,104 A | 2/2000 | Schmidt et al. | |
| 6,033,705 A | 3/2000 | Isaacs | |
| 6,039,992 A | 3/2000 | Compardre et al. | |
| 6,049,002 A | 4/2000 | Mattila et al. | |
| 6,071,356 A | 6/2000 | Olsen | |

| | | | | | | |
|---|---|---|---|---|---|---|
| 6,080,712 A | 6/2000 | Revell et al. | | EP | 0 242 990 A2 | 10/1987 |
| 6,096,226 A | 8/2000 | Fuchs et al. | | EP | 0 361 955 A2 | 4/1990 |
| 6,096,266 A | 8/2000 | Duroselle | | EP | 0 404 293 A2 | 12/1990 |
| 6,096,348 A | 8/2000 | Miner et al. | | EP | 0 460 962 | 12/1991 |
| 6,103,286 A | 8/2000 | Gutzmann et al. | | EP | 0 461 700 A1 | 12/1991 |
| 6,111,963 A | 8/2000 | Thompson, III | | EP | 0 569 066 A1 | 11/1993 |
| 6,113,963 A | 9/2000 | Gutzmann et al. | | EP | 0 603 329 | 6/1994 |
| 6,165,483 A | 12/2000 | Hei et al. | | EP | 0 667 392 A2 | 2/1995 |
| 6,176,971 B1 | 1/2001 | Sun Yu et al. | | EP | 0 779 357 A1 | 12/1995 |
| 6,183,807 B1 | 2/2001 | Gutzmann et al. | | EP | 0 805 198 A1 | 7/1996 |
| 6,194,367 B1 | 2/2001 | Talley | | EP | 0 843 001 A1 | 11/1996 |
| 6,221,323 B1 | 4/2001 | Mizuno et al. | | EP | 0751211 A1 | 1/1997 |
| 6,238,685 B1 | 5/2001 | Hei et al. | | EP | 0772971 A2 | 5/1997 |
| 6,257,253 B1 | 7/2001 | Lentsch et al. | | EP | 0 967 203 | 12/1999 |
| 6,274,542 B1 | 8/2001 | Carr et al. | | EP | 0 985 349 A2 | 3/2000 |
| 6,302,968 B1 | 10/2001 | Baum et al. | | EP | 1 010 750 A1 | 6/2000 |
| 6,306,252 B1 | 10/2001 | Ryham | | EP | 1 382 666 A1 | 1/2004 |
| 6,395,703 B2 | 5/2002 | Scepanski | | FR | 2 578 988 | 9/1986 |
| 6,423,868 B1 | 7/2002 | Carr et al. | | GB | 1 570 492 | 11/1975 |
| 6,436,445 B1 | 8/2002 | Hei et al. | | GB | 1577396 | 10/1980 |
| 6,451,746 B1 | 9/2002 | Moore et al. | | GB | 2 182 051 | 5/1987 |
| 6,472,199 B1 | 10/2002 | Monken | | GB | 2 187 958 | 9/1987 |
| 6,489,281 B1 | 12/2002 | Smith et al. | | GB | 2 207 354 | 2/1989 |
| 6,514,556 B2 | 2/2003 | Hilgren et al. | | GB | 2 255 507 | 11/1992 |
| 6,545,047 B2 | 4/2003 | Gutzmann et al. | | GB | 2 257 630 | 1/1993 |
| 6,589,565 B1 | 7/2003 | Richter et al. | | GB | 2 353 800 | 3/2001 |
| 6,593,283 B2 | 7/2003 | Hei et al. | | GR | 1 494 109 | 12/1977 |
| 6,627,593 B2 | 9/2003 | Hei et al. | | JP | 7-31210 | 2/1995 |
| 6,627,657 B1 | 9/2003 | Hilgren et al. | | JP | 7-258005 | 10/1995 |
| 6,630,439 B1 | 10/2003 | Norwood et al. | | NL | 9201631 | 9/1992 |
| 6,635,286 B2 | 10/2003 | Hei et al. | | RU | 2102447 C1 | 8/1996 |
| 6,638,902 B2 | 10/2003 | Tarara et al. | | WO | WO 93/01716 | 2/1993 |
| 6,674,538 B2 | 1/2004 | Takahashi | | WO | WO 94/06294 | 3/1994 |
| 6,783,767 B2 | 8/2004 | Shroot et al. | | WO | WO 94/14321 | 7/1994 |
| 7,056,536 B2 * | 6/2006 | Richter et al. ............... 424/616 | | WO | WO 94/15465 | 7/1994 |
| 7,150,884 B1 * | 12/2006 | Hilgren et al. ............... 424/616 | | WO | WO 94/21122 | 9/1994 |
| 7,498,051 B2 * | 3/2009 | Man et al. .................... 426/332 | | WO | WO 94/23575 | 10/1994 |
| 7,504,123 B2 * | 3/2009 | Man et al. .................... 426/332 | | WO | WO 95/34537 | 12/1995 |
| 7,504,124 B2 * | 3/2009 | Man et al. .................... 426/332 | | WO | WO 96/19559 | 6/1996 |
| 7,507,429 B2 * | 3/2009 | Man et al. .................... 426/332 | | WO | WO 96/30474 | 10/1996 |
| 2002/0128312 A1 | 9/2002 | Hei et al. | | WO | WO 98/28267 | 7/1998 |
| 2002/0159917 A1 | 10/2002 | Swart et al. | | WO | WO 99/51095 | 10/1999 |
| 2002/0177220 A1 | 11/2002 | Monken | | WO | WO 00/18870 | 4/2000 |
| 2003/0087786 A1 | 5/2003 | Hei et al. | | WO | WO 01/47359 | 7/2001 |
| 2003/0139311 A1 * | 7/2003 | Biering et al. ............... 510/302 | | WO | WO 02/03799 | 1/2002 |
| 2003/0157192 A1 | 8/2003 | Shroot et al. | | WO | WO 02/054866 A1 | 7/2002 |
| 2003/0199583 A1 | 10/2003 | Gutzmann et al. | | WO | WO 02/060280 | 8/2002 |
| 2004/0007255 A1 | 1/2004 | Labib | | WO | WO 2004/043162 | 5/2004 |
| 2004/0029755 A1 | 2/2004 | Bragulla | | WO | WO2005/090542 | 9/2005 |
| 2004/0147423 A1 | 7/2004 | Scialla et al. | | | | |
| 2004/0266639 A1 | 12/2004 | Spindler | | | | |
| 2005/0153859 A1 * | 7/2005 | Gohl et al. ................... 510/302 | | | OTHER PUBLICATIONS | |
| 2005/0183744 A1 | 8/2005 | Staub et al. | | | | |
| 2006/0042665 A1 | 3/2006 | Fernholz et al. | | | | |
| 2006/0046945 A1 | 3/2006 | Herdt et al. | | | | |
| 2008/0121250 A1 | 5/2008 | Fernholz et al. | | | | |
| 2009/0145859 A1 * | 6/2009 | Man et al. .................... 210/759 | | | | |

FOREIGN PATENT DOCUMENTS

| | | |
|---|---|---|
| DE | 30 03 875 A1 | 8/1981 |
| DE | 3543500 | 6/1987 |
| DE | 39 06 044 A1 | 8/1990 |
| DE | 0538/9310 | 5/1993 |
| DE | 19804829 | 8/1999 |
| DK | 9300538 | 11/1994 |
| EP | 0 125 781 | 11/1984 |
| EP | 0 140 648 | 5/1985 |
| EP | 0 167 375 A2 | 1/1986 |
| EP | 186052 | 7/1986 |
| EP | 0 195 619 A2 | 9/1986 |
| EP | 0 233 731 A2 | 8/1987 |
| EP | 0 233 731 | 9/1987 |

OTHER PUBLICATIONS

Abstract: "Indirect food additives: adjuvants, production aids, and sanitizers", *Fed. Register*, 61(108), 28051-28053, 1 pg. (Jun. 4, 1996).

Armak Chemicals, "NEO-FAT Fatty Acids", *Akzo Chemicals Inc.*, Bulletin No. 86-17 (1986).

Baldry, M.G.C., "The bactericidal, fungicidal and sporicidal properties of hydrogen peroxide and peracetic acid," *Journal of Applied Bacteriology*, vol. 54 (1983) pp. 417-423.

Baldry et al., "Disinfection of Sewage Effluent with Peracetic Acid," *Wat. Sci. Tech.*, vol. 21, No. 3 (1989) pp. 203-206.

Bayliss et al., "The Synergistic Killing of Spores of *Bacillus subtilis* by Hyrdrogen Peroxide and Ultra-Violet Light Irradiation," *FEMS Microbiology Letters*, 5 (1979) pp. 331-333.

Bell, K. et al., "Reduction of foodborne micro-organisms on beef carcass tissue using acetic acid, sodium bicarbonate, and hydrogen peroxide spray washes", *Food Microbiology*, vol. 14, pp. 439-448 (1997).

Beuchat, Larry R., "Surface Disinfection of Raw Produce," *Dairy, Food and Environmental Sanitation*, vol. 12, No. 1 (Jan. 1992) pp. 6-9.

Block, Seymour S., "Peroxygen Compounds," *Disinfection, Sterilization, and Preservation*, Fourth Edition, Chapter 9 (1991) pp. 167-181.

Block, Seymour S., "Peroxygen Compounds," *Disinfection, Sterilization and Preservation*, Fifth Edition, Chapter 9 (2001) pp. 185-204.

Breen, P. et al., "Elimination of *Salmonella* Contamination from Poultry Tissues by Cetylpyridinium Chloride Solutions", *Journal of Food Protection*, 60(9): 1019-1021 (1997).

Breen, P. et al., "Quaternary Ammonium Compounds Inhibit and Reduce the Attachment of Viable *Salmonella typhimurium* to Poultry Tissues", *Journal of Food Science*, 60(6):1191-1196 (1995).

Brown, G. Eldon, "Use of Xanthomonas-campestris pv-vesicatoria to Evaluate Surface Disinfectants for Canker Quarantine Treatment of Citrus Fruit," *Plant Disease* (Apr. 1987) pp. 319-323.

Computer search results—Level 1—5 patents (Mar. 1994).

Computer search results from Ecolab Information Center (Jun. 1998).
International Search Report dated Jan. 30, 2002.
International Search Report dated Jun. 3, 2002.
International Search Report dated Dec. 27, 2002.
International Search Report dated Jul. 4, 2005 (PCT/US2005/000147).
International Search Report dated Jun. 28, 2005 (PCT/US2005/000149).
International Search Report dated Jun. 28, 2005 (PCT/US2005/000231).
International Search Report dated May 3, 2005.
Cords, B.R., "New Peroxyacetic Acid Sanitizer", *Proceedings*, Twenty-Third Convention, Institute of Brewing, Sydney Australia, pp. 165-169 (1995).
Dickens, J. et al., "The Effect of Acetic Acid and Air Injection on Appearance, Moisture Pick-Up, Microbiological Quality, and *Salmonella* Incidence on Processed Poultry Carcasses", *Poultry Science*, 73:582-586 (1994).
Dickens, J. et al., "The Effect of an Acetic Acid Dip on Carcass Appearance, Microbiological Quality, and Cooked Breast Meat Texture and Flavor", *Poultry Science*, 73:576-581 (1994).
Dickens, J. et al., "The Effects of Extended Chilling Times with Acetic Acid on the Temperature and Microbiological Quality of Processed Poultry Carcasses", *Poultry Science*, 74:1044-1048 (1995).
Dickens, J. et al., "Effects of Acetic Acid and Hydrogen Peroxide Application During Defeathering on the Microbiological Quality of Broiler Carcasses Prior to Evisceration", *Poultry Science*, 76:657-660 (1997).
Dickinson, J. et al., "Microbiological Decontamination of Food Animal Carcasses by Washing and Sanitizing Systems: A Review", *Journal of Food Protection*, 55(2):133-140 (Feb. 1992).
Eggensperger, H., "Disinfectants Based on Peracid-Splitting Compounds", *Zbl. Bakt. Hyg.*, I. Abt. Orig. B 168, pp. 517-524 (1979).
Focus on Interox, *Effluent + Water Treatment Journal* (Aug. 1979).
Fraser, J.A.L., "Novel applications of peracetic acid in industrial disinfection," *Specialty Chemicals*, vol. 7, No. 3 (1987) pp. 178, 180, 182, 184, 186.
FSTA abstract, accession No. 1999(10):C1223, abstracting: Journal of Food Protection, vol. 62(7), pp. 761-765 (1999).
FSTA abstract, accession No. 2000(06):J1220, abstracting: Dairy, Food and Environmental Sanitation, vol. 19(12), pp. 842-847 (1999).
Greenspan et al., "The Application of Peracetic Acid Germicidal Washes to Mold Control of Tomatoes," *Food Technology*, vol. 5, No. 3 (Mar. 1951) pp. 95-97.
Han et al., "Destruction of Bacterial Spores on Solid Surfaces," *Journal of Food Processing and Preservation*, vol. 4, No. 1-2 (1980) pp. 95-110.
Heinemann, P.G., "The Germicidal Efficiency of Commercial Preparations of Hydrogen Peroxid," *The Journal of the American Medical Association* , vol. LX, No. 21 (1913) pp. 1603-1606.
Hilgren, J. et al., *Patent Application*, U.S. Appl. No. 09/614,631, filed Jul. 12, 2000.
Hutchings et al., "Comparative Evaluation of the Bactericidal Efficiency of Peracetic Acid, Quaternaries, and Chlorine-Containing Compounds," *Presented at the 49th General Meeting of the Society of American Bacteriologists*, (Abstract) (1949) pp. 50-51.
Jager et al., "Peracetic acid as a disinfectant in breweries and soft drink factories," *Mitt. Versuch. Gaorung. Wien.*, vol. 34 (1980) pp. 32-36.
Kim, J. et al., "Cetylpyridinium Chloride (CPC) Treatment on Poultry Skin to Reduce Attached *Salmonella", Journal of Food Protection*, 59(3):322-326 (1995).
Kunzmann, T., "Investigations on the disinfecting action of hydrogen peroxides," *Fortschr. Med.*, vol. 52, No. 16 (1934) pp. 357-359.
Laska, M. et al., "Odor structure-activity relationships of carboxylic acids correspond between squirrel monkeys and humans", *Am. J. Physiol.*, 274:R1639-R1645 (1998).
Lillard, H., "Bacterial Cell Characteristics and Conditions Influencing their Adhesion to Poultry Skin", *Journal of Food Protection*, 48(9):803-807 (Sep. 1985).
Lillard, H., "Factors Affecting the Persistence of *Salmonella* During the Processing of Poultry", *Journal of Food Protection*, 52(11):829-832 (Nov. 1989).
Lion C. et al., "New decontaminants. Reaction of peroxyacid esters with toxic insecticides", *Bull. Soc. Chim. Belg.*, vol. 100, No. 7, pp. 555-559 (1991).
Merka, V. et al., "Disinfectant properties of some peroxide compounds.", Abstract No. 67542e, *Chemical Abstracts*, vol. 67 (1967).
MicroPatent Report dated Aug. 18, 2003.
Mulder, R.W.A.W. et al., "Research Note: *Salmonella* Decontamination of Broiler Carcasses with Lactic Acid, L-Cysteine, and Hdrogen Peroxide", *Poultry Science*, vol. 66, pp. 1555-1557 (1987).
Opinion Letter dated Apr. 11, 2000.
Orth et al., "Is the control of *Listeria, Campylobacter* and *Yersinia* a disinfection problem?", *Fleischwirtsch*, 69 (10) (1989) pp. 1575-1576.
Parker, W. et al., "Peroxides. II. Preparation, Characterization and Polarographic Behavior of Longchaing Aliphatic Peracids", *Synthesis and Properties of LongChain Aliphatic Peracids*, vol. 77, pp. 4037-4041 (Aug. 5, 1955).
Parker, W. et al., "Peroxides. IV. Aliphatic Diperacids", *Aliphatic Diperacids*, vol. 79, pp. 1929-1931 (Apr. 20, 1957).
Poffe et al., "Disinfection of Effluents from Municipal Sewage Treatment Plants with Peroxy Acids," *Zbl. Bakt. Hyg., I. Abt. Orig.* B 167 (1978) pp. 337-346.
Ranganna et al., "Chemical Preservatives and Antioxidants," *Indian Food Packer* (May-Jun. 1981) pp. 30-44.
Richardson, B.W., "On Peroxide of Hydrogen, or Ozone Water, as a Remedy," *The Lancet* (Mar. 1891) pp. 707-709, 760-763.
Search Results (2003).
Sims, Alan F.E., "Industrial effluent treatment with hydrogen peroxide," *Chemistry and Industry*, No. 14 (1983) pp. 555-558.
Tamblyn, K. et al., "Bactericidal Activity of Organic Acids against *Salmonella typhimurium* Attached to Broiler Chicken Skin", *Journal of Food Protection*, 60(6):629-633 (1997).
Taylor, J.H. et al., "A comparison of the bactericidal efficacy of 18 disinfectants used in the food industry against *Escherichia coli* O 157:H7 . . . " *Journal of Applied Microbiology*, 87:718-725 (1999).
Xiong, H. et al., "Spraying Chicken Skin with Selected Chemicals to Reduce Attached *Salmonella typhimurium", Journal of Food Protection*, 61(3):272-275 (1998).
Yoshpe et al., "Disinfection of Water by Hydrogen Peroxide," *Health Laboratory Science*, vol. 5, No. 4 (1968) pp. 233-238.
Baldry et al., "Disinfection with peroxygens," Industrial Biocides, edited by K.R. Payne, New York, John Wiley & Sons, pp. 91-116 (1988).
Interox Chemicals Ltd. product brochure entitled "Oxymaster Peracetic Acid 12%" (before May 9, 2006).
Interox Chemicals Ltd. product brochure entitled "Proxitane 4002 Peracetic Acid 36-40%" (1982).
Nambudripad et al., "Bactericidal Efficiency of Hydrogen Peroxide Part I. Influence of different concentrations on the rate and extent of destruction of some bacteria of dairy importance" (Received Jan. 22, 1949).

Pfizer Chemical Division, "Pfizer Flocon® Biopolymers for Industrial Uses (xanthan broths)", Data Sheet 679 (before May 9, 2006).

Search Report for the use of amine oxides with hydrogen peroxide in bleaching, sanitizing, disinfectant or hard surface cleaners (2003).

Search Result from Database WPI and Database Inpadoc (1998).

Solvay product brochure entitled Oxymaster®—Proxitane® Peracetic Acid Applications (1998).

Solvay product brochure entitled Oxymaster®—Proxitane® Peracetic Acid Solutions: Handling, Storage and Transport Information (Safety Documentation) (1999).

Towle, G. et al., "Industrial Gums Polysaccharides and Their Derivatives", Second Edition, Ch. XIX, "Pectin", pp. 429-444 (1973).

* cited by examiner

NEUTRAL OR ALKALINE MEDIUM CHAIN PEROXYCARBOXYLIC ACID COMPOSITIONS AND METHODS EMPLOYING THEM

CROSS REFERENCE TO RELATED APPLICATIONS

The present application claims the benefit of U.S. Provisional Patent Application Ser. No. 60/697,303, filed Jul. 6, 2005, and claims priority as continuation-in-parts to the following 8 applications: Ser. No. 11/030,641 filed Jan. 4, 2005 and now pending; Ser. No. 11/030,271 filed Jan. 4, 2005 now U.S. Pat. No. 7,498,051; Ser. No. 11/029,235 filed Jan. 4, 2005 now U.S. Pat. No. 7,504,124; Ser. No. 11/030,233 filed Jan. 4, 2005 now abandoned; Ser. No. 10/754,426 filed Jan. 9, 2004 now allowed; Ser. No. 10/754,396 filed Jan. 9, 2004 now U.S. Pat. No. 7,504,123; Ser. No. 10/754,436 filed Jan. 9, 2004 now U.S. Pat. No. 7,507,429; and Ser. No. 10/754,405 filed Jan. 9, 2004 now pending. The disclosures of which are incorporated herein by reference.

FIELD OF THE INVENTION

The present invention relates to medium chain peroxycarboxylic acid compositions of neutral or alkaline pH, to methods of making these compositions, and to methods employing these compositions. The methods include methods of cleaning. The compositions include cleaning compositions.

BACKGROUND OF THE INVENTION

Conventional peroxycarboxylic acid compositions typically include short chain peroxycarboxylic acids or mixtures of short chain peroxycarboxylic acids and medium chain peroxycarboxylic acids (see, e.g., U.S. Pat. Nos. 5,200,189, 5,314,687, 5,409,713, 5,437,868, 5,489,434, 6,674,538, 6,010,729, 6,111,963, and 6,514,556). Ongoing research efforts have strived for improved peroxycarboxylic acid compositions. In particular, these efforts have strived for compositions that have effective antimicrobial activity, that can be readily made, and that have beneficial properties. There remains a need for peroxycarboxylic acid compositions that are effective cleaners and for methods employing such compositions.

SUMMARY OF THE INVENTION

The present invention relates to compositions including medium chain peroxycarboxylic acid that are at or are brought to neutral or alkaline pH, and to methods employing them. The methods include methods of cleaning. The compositions include cleaning compositions.

In an embodiment, the present invention relates to a method of cleaning a soiled object. This embodiment of the method can include contacting the object with neutral or alkaline medium chain peroxycarboxylic acid composition. The composition can be at any of a variety of neutral or alkaline pH. In an embodiment, the neutral or alkaline pH is about 6 to about 14. In an embodiment, the neutral or alkaline pH is about 9 to about 12. In an embodiment, the neutral or alkaline pH is about 6 to about 8. In an embodiment, the neutral or alkaline pH is about 8 to about 14.

The neutral or alkaline medium chain peroxycarboxylic acid composition can be formed or provided in any of a variety of ways. In an embodiment, the method can include contacting the object with an acid pH medium chain peroxycarboxylic acid composition and contacting the object with a source of alkalinity to form the neutral or alkaline medium chain peroxycarboxylic acid composition. In an embodiment, the method can include providing an acid pH medium chain peroxycarboxylic acid composition; providing a source of alkalinity; and mixing the acid pH medium chain peroxycarboxylic acid composition and the source of alkalinity at the point of use to form the neutral or alkaline medium chain peroxycarboxylic acid composition. In an embodiment, the method can include providing an acid pH medium chain peroxycarboxylic acid composition; providing a source of alkalinity; and mixing the acid pH medium chain peroxycarboxylic acid composition and the source of alkalinity during use to form the neutral or alkaline medium chain peroxycarboxylic acid composition.

The method can employ any of a variety of sources of alkalinity. In an embodiment, the source of alkalinity includes or is alkali metal hydroxide, alkali metal phosphate, alkali metal carbonate, alkanol amine, or the like, or mixture thereof. In an embodiment, the source of alkalinity includes or is neutral or alkaline pH medium chain peroxycarboxylic acid composition.

The method can include any of a ways of contacting an object with the neutral or alkaline medium chain peroxycarboxylic acid composition. In an embodiment, the method can include contacting the object with an acid pH medium chain peroxycarboxylic acid composition for a predetermined time; and after passage of the predetermined time, contacting the object with a source of alkalinity to form the neutral or alkaline medium chain peroxycarboxylic acid composition. In an embodiment, the method can include contacting the object with an acid pH medium chain peroxycarboxylic acid composition and contacting the object with a source of alkalinity to form an intermediate pH neutral or alkaline medium chain peroxycarboxylic acid composition. In an embodiment, the method can include contacting the object with a source of alkalinity to form a second pH neutral or alkaline medium chain peroxycarboxylic acid composition. In an embodiment, the intermediate pH is about 9. In an embodiment, the second pH is about 12.

The method can be employed to clean any of a variety of objects. In an embodiment, the soiled object includes or is pipes or vessels in a food processing plant, wares, laundry, an oven, a grill, or a floor, a carpet, a medical device. In an embodiment, the soiled object includes or is heat transfer equipment.

The present invention also relates to a medium chain peroxycarboxylic acid composition of neutral or alkaline pH. In an embodiment, the composition includes an acid pH medium chain peroxycarboxylic acid composition and a source of alkalinity.

DETAILED DESCRIPTION OF THE INVENTION

Definitions

Figure 1:
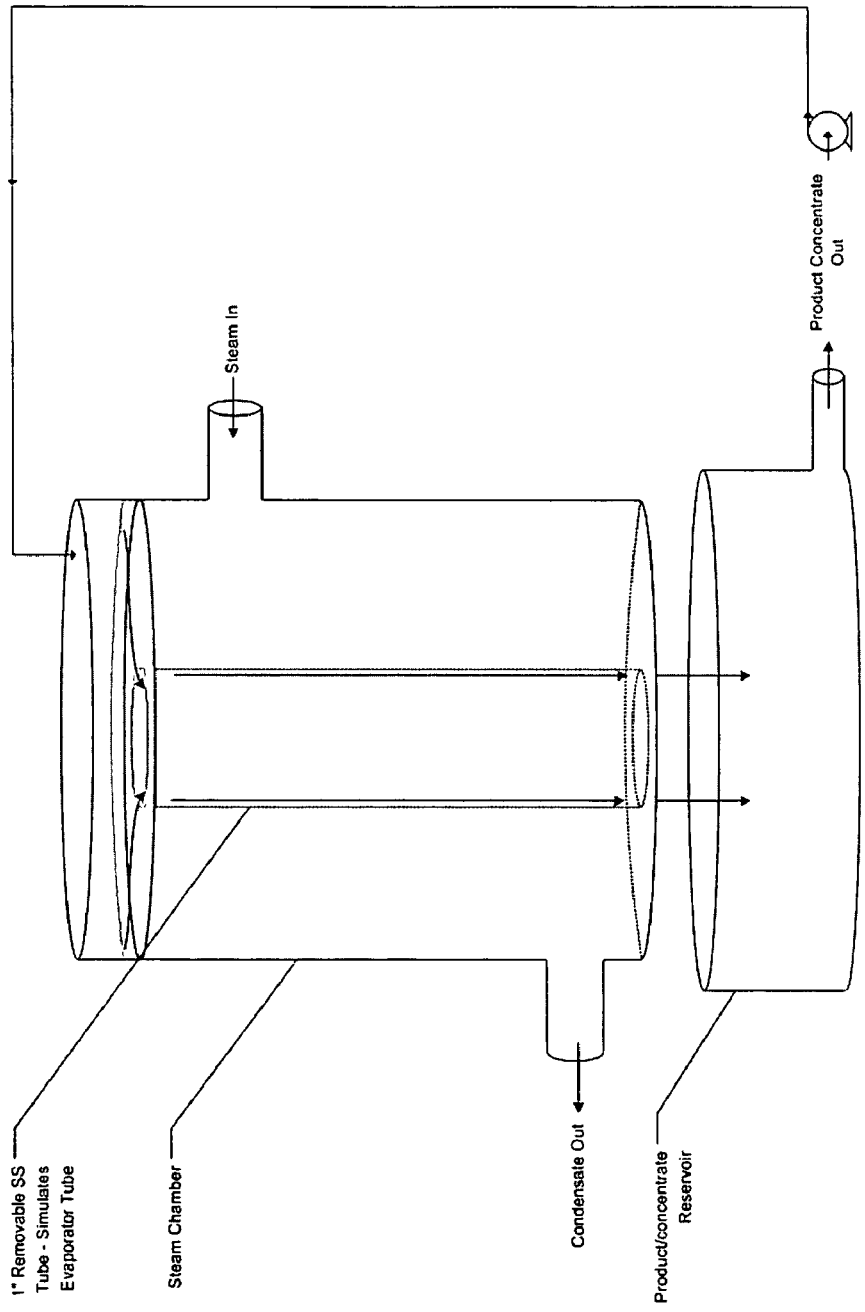
FIG. 1 schematically illustrates a lab-scale evaporator tube apparatus employed for evaluating the present compositions for cleaning of soil in an apparatus such as an evaporator tube.

As used herein, the phrase "medium chain carboxylic acid" refers to a carboxylic acid that: 1) has reduced or is lacking odor compared to the bad, pungent, or acrid odor associated with an equal concentration of small chain carboxylic acid, and 2) has a critical micellar concentration greater than 1 mM in aqueous buffers at neutral pH. Medium chain carboxylic acids exclude carboxylic acids that are infinitely soluble in or miscible with water at 20° C. Medium chain carboxylic acids include carboxylic acids with boiling points (at 760 mm Hg pressure) of 180 to 300° C. In an embodiment, medium chain carboxylic acids include carboxylic acids with boiling points (at 760 mm Hg pressure) of 200 to 300° C. In an embodiment, medium chain carboxylic acids include those with solubility in water of less than 1 g/L at 25° C. Examples of medium chain carboxylic acids include pentanoic acid, hexanoic acid, heptanoic acid, octanoic acid, nonanoic acid, decanoic acid, undecanoic acid, and dodecanoic acid.

As used herein, the phrase "medium chain peroxycarboxylic acid" refers to the peroxycarboxylic acid form of a medium chain carboxylic acid.

As used herein, the phrase "short chain carboxylic acid" refers to a carboxylic acid that: 1) has characteristic bad, pungent, or acrid odor, and 2) is infinitely soluble in or miscible with water at 20° C. Examples of short chain carboxylic acids include formic acid, acetic acid, propionic acid, and butyric acid.

As used herein, the phrase "short chain peroxycarboxylic acid" refers to the peroxycarboxylic acid form of a short chain carboxylic acid.

As used herein, the term "solubilizer" refers to a component of the present compositions to that makes soluble or increases the solubility in a carrier (e.g., water) of the medium chain carboxylic acid, medium chain peroxycarboxylic acid, or mixture thereof. For example, in an embodiment, the solubilizer can keep a composition including medium chain carboxylic acid, medium chain peroxycarboxylic acid, or mixture thereof in solution or can keep the composition finely and evenly dispersed under ordinary storage conditions without forming a separate layer. The solubilizer can, for example, solubilize a medium chain carboxylic acid to an extent sufficient to allow it to react with an oxidizing agent, such as hydrogen peroxide. A solubilizer can be identified by a test that measures phase separation under ordinary storage conditions, such as room temperature, 100° F., or 60° C. As used herein, the term "solubilizer" does not include short chain carboxylic acids; they are not solubilizers.

As used herein, the term "microemulsion" refers to a thermodynamically stable dispersion of one liquid phase into another stabilized by an interfacial film of surfactant. The dispersion can be oil-in-water or water-in-oil. Microemulsions are typically clear solutions when the droplet diameter is approximately 100 nanometers or less. In an embodiment, the present microemulsion composition is a shear thinning viscoelastic gel that has a blue tyndall appearance.

As used herein, the phrases "blue tyndall appearance" or "blue tyndall" refer to a bluish hue due to scattering of blue light or the blue region of the light spectrum.

As used herein, the phrases "viscoelastic gel" and "viscoelastic liquid" refer to a liquid composition that exhibits both viscous and elastic characteristics or responses, which is indicative of long range order or structure.

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods short chain carboxylic acids, short chain peroxycarboxylic acids, or mixtures thereof; unless such an ingredient is specifically listed after the phrase.

As used herein, a composition or combination "substantially free of" one or more ingredients refers to a composition that includes none of that ingredient or that includes only trace or incidental amounts of that ingredient. Trace or incidental amounts can include the amount of the ingredient found in another ingredient as an impurity or that is generated in a minor side reaction during formation or degradation of the medium chain peroxycarboxylic acid.

As used herein, the phrase "a level insufficient to solubilize" refers to a concentration of an ingredient at which the ingredient is not sufficient to solubilize an insoluble material and to keep the composition substantially in one phase.

As used herein, the phrases "objectionable odor", "offensive odor", or "malodor" refer to a sharp, pungent, or acrid odor or atmospheric environment from which a typical person withdraws if they are able to. Hedonic tone provides a measure of the degree to which an odor is pleasant or unpleasant. An "objectionable odor", "offensive odor", or "malodor" has an hedonic tone rating it as unpleasant as or more unpleasant than a solution of 5 wt-% acetic acid, propionic acid, butyric acid, or mixtures thereof.

As used herein, the term "microorganism" refers to any noncellular or unicellular (including colonial) organism. Microorganisms include all prokaryotes. Microorganisms include bacteria (including cyanobacteria), lichens, fungi, protozoa, virinos, viroids, viruses, phages, and some algae. As used herein, the term "microbe" is synonymous with microorganism.

As used herein, the term "biofilm" refers to a population of microorganisms concentrated at an interface (usually solid/liquid) and typically surrounded by an extracellular polymeric slime matrix. Biofilms include complex associations of cells, extracellular products, and detritus either trapped within the biofilm or released from cells which have lysed as the biofilm ages. The main 'cement' for all these cells and products can be the mixture of polysaccharides secreted by the cells established within the biofilm. These polysaccharides are typically referred to as exopolysaccharides. In contrast, flocs are suspended aggregates of micro-organisms surrounded by an extracellular polymeric slime matrix that formed in liquid suspension. They have many of the same characteristics as biofilms.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, a membrane, and the like. Objects also include surfaces and articles employed in hospitality and industrial sectors.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a stabilized composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthroscopes) and related equipment, and the like, or combinations thereof.

As used herein, "agricultural" or "veterinary" objects or surfaces include animal watering stations and enclosures, animal quarters, animal veterinarian clinics (e.g. surgical or treatment areas), animal surgical areas, and the like.

As used herein, "residential" or "institutional" objects or surfaces include those found in structures inhabited by humans. Such objects or surfaces include bathroom surfaces, drains, drain surfaces, kitchen surfaces, and the like.

As used herein, weight percent (wt-%), percent by weight, % by weight, and the like are synonyms that refer to the concentration of a substance as the weight of that substance divided by the weight of the composition and multiplied by 100. Unless otherwise specified, the quantity of an ingredient refers to the quantity of active ingredient.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the phrase "densified fluid" refers to a fluid in a critical, subcritical, near critical, or supercritical state. The fluid is generally a gas at standard conditions of one atmosphere pressure and 0° C. As used herein, the phrase "supercritical fluid" refers to a dense gas that is maintained above its critical temperature, the temperature above which it cannot be liquefied by pressure. Supercritical fluids are typically less viscous and diffuse more readily than liquids. In an embodiment, a densified fluid is at, above, or slightly below its critical point. As used herein, the phrase "critical point" is the transition point at which the liquid and gaseous states of a substance merge into each other and represents the combination of the critical temperature and critical pressure for a substance. The critical pressure is a pressure just sufficient to cause the appearance of two phases at the critical temperature. Critical temperatures and pressures have been reported for numerous organic and inorganic compounds and several elements.

As used herein, the terms "near critical" fluid or "subcritical" fluid refer to a fluid material that is typically below the critical temperature of a supercritical fluid, but remains in a fluid state and denser than a typical gas due to the effects of pressure on the fluid. In an embodiment, a subcritical or near critical fluid is at a temperature and/or pressure just below its critical point. For example, a subcritical or near critical fluid can be below its critical temperature but above its critical pressure, below its critical pressure but above its critical temperature, or below both its critical temperature and pressure. The terms near critical and subcritical do not refer to materials in their ordinary gaseous or liquid state.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

Neutral or Alkaline Medium Chain Peroxycarboxylic Acid Compositions

The present invention relates to medium chain peroxycarboxylic acid compositions of neutral or alkaline pH, to methods of making these compositions, and to methods employing these compositions. The compositions can be provided having a neutral or alkaline pH. The compositions can be provided at a lower pH and brought to neutral or alkaline pH at the point of use. The compositions can be provided at a lower pH and brought to neutral or alkaline pH during use. The compositions can be made by mixing a buffer or alkaline component with an acidic medium chain peroxycarboxylic acid composition.

In an embodiment, the present method can include contacting an object with a neutral or alkaline pH medium chain peroxycarboxylic acid composition and cleaning the object. Such a method can include applying an acid pH medium chain peroxycarboxylic acid composition the object and applying a source of alkalinity to the object. Applying the source of alkalinity can be before, simultaneous with, or after applying the acid pH medium chain peroxycarboxylic acid composition to the object. Such a method can include applying a neutral pH medium chain peroxycarboxylic acid composition the object and applying a source of alkalinity to the object. Applying the source of alkalinity can be before, simultaneous with, or after applying the neutral pH medium chain peroxycarboxylic acid composition to the object.

These compositions can be employed in methods including cleaning, reducing population of a microbe, or both. For example, a method employing the medium chain peroxycarboxylic acid composition can include applying an acid pH medium chain peroxycarboxylic acid composition, reducing the population of a microbe on an object, increasing the pH of the composition, and cleaning the object. For example, a method employing the medium chain peroxycarboxylic acid composition can include applying a neutral pH medium chain peroxycarboxylic acid composition (optionally cleaning also), reducing the population of a microbe on an object, increasing the pH of the composition, and cleaning the object. Increasing the pH of the composition can be accomplished, for example, by adding additional medium chain peroxycarboxylic acid composition of neutral or alkaline pH. Increasing the pH of the composition can be accomplished, for example, by mixing a buffer or alkaline component with the composition already contacting the object.

In certain embodiments, the compositions can be at, or the methods can employ, a neutral or alkaline pH of about 6 to about 14, about 7 to about 13, or about 8 to about 12, for example, about 8, about 9, about 10, about 11, about 12, about 13, or about 14. In certain embodiments, the compositions can be at, or the methods can employ, a neutral pH of about 6 to about 8. In certain embodiments, the compositions can be at, or the methods can employ, an alkaline pH of about 8 to about 14, about 8 to about 12, or about 9 (e.g., 8.7) to about 12 (e.g., 11.8), for example, about 8, about 9, about 10, about 11, about 12, about 13, or about 14. In certain embodiments, the compositions can be at, or the methods can employ, an alkaline pH of at least about 9, at least about 10, at least about 11, at least about 12, at least about 13, or at least about 14.

In an embodiment, the present method employing the medium chain peroxycarboxylic acid composition can include applying an acid pH medium chain peroxycarboxylic acid composition to a soiled object. For example, the composition can be introduced into pipes or vessels in a plant, such as a food processing plant. The pipes or vessels can be subjected to cleaning-in-place (CIP). Upon applying, the composition can be allowed to contact the soiled object for a predetermined amount of time. The amount of time can be sufficient to allow the composition to penetrate soil. The method can include penetrating the soil with the composition.

This embodiment of the method also includes applying a source of alkalinity to the soiled object or to the composition contacting the soiled object. The source of alkalinity can include a buffer or alkaline component. This embodiment of the method can include applying a buffer or alkaline component to the composition already contacting the soiled object. Applying the source of alkalinity can increase the pH of the cleaning composition to, for example, the neutral or alkaline ranges or values described herein. Alternatively, the buffer or alkaline component can be used to treat the soil before adding the medium chain peroxycarboxylic composition.

An embodiment of such a method can include applying a source of alkalinity to the soiled object or to the composition contacting the soiled object to increase the pH to an intermediate value. Upon applying, the soiled object can be contacted with the composition at the intermediate pH for a predetermined amount of time. The intermediate pH can be about pH 9. This embodiment can include applying additional or second source of alkalinity to the soiled object or to the composition contacting the soiled object to further increase the pH to a second neutral or alkaline value. Upon applying, the soiled object can be contacted with the composition at the second neutral or alkaline pH for a predetermined amount of time. The second neutral or alkaline pH can be about pH 12.

In an embodiment, the present method employing the medium chain peroxycarboxylic acid composition can include applying an acid pH medium chain peroxycarboxylic acid composition to soiled wares. For example, the composition can be introduced in a first cycle in a ware washing machine. Upon applying, the composition can be allowed to contact the soiled wares for a predetermined amount of time. This embodiment can also include applying (e.g., by spraying) a source of alkalinity to the soiled wares. Applying the source of alkalinity can increase the pH of the cleaning composition to, for example, the neutral or alkaline ranges or values described herein.

In an embodiment, the present method can include low temperature machine washing of wares. The acid pH medium chain peroxycarboxylic acid composition can be applied to wares in the last step of a cycle. This can sanitize the wares. This acid pH medium chain peroxycarboxylic acid composition can then be mixed with an alkaline cleaner used in a subsequent cleaning step. The resulting neutral or alkaline medium chain peroxycarboxylic acid composition can increase cleaning by the alkaline cleaner.

In an embodiment, the present method employing the medium chain peroxycarboxylic acid composition can include applying an acid pH medium chain peroxycarboxylic acid composition to soiled wares or to soiled laundry. For example, the composition can be employed as a presoak. Upon soaking, the composition can be allowed to contact the soiled wares or laundry for a predetermined amount of time. The presoak composition can be added to the laundry or ware washing machine. Then the laundry or ware can be cleaned with a conventional alkaline cleaning composition. The medium chain peroxycarboxylic acid composition can increase cleaning by the alkaline cleaning composition.

In an embodiment, the present method employing the medium chain peroxycarboxylic acid composition can include applying an acid pH medium chain peroxycarboxylic acid composition to a soiled object. This embodiment also includes applying a source of alkalinity to the soiled object. The source of alkalinity can include a buffer or alkaline component. The medium chain peroxycarboxylic acid composition and the source of alkalinity can be applied simultaneously or nearly so (generally at the same or an overlapping time). The medium chain peroxycarboxylic acid composition and the source of alkalinity can be mixed and then applied. For example, the compositions can be applied to a hard surface (such as an interior surface of an oven, a surface of a grill, or a floor), to a carpet, or employed for spray cleaning degreasing. Applying the source of alkalinity can increase the pH of the cleaning composition to, for example, the neutral or alkaline ranges or values described herein.

In such an embodiment, the compositions can be applied employing a co-spraying system. For example, the co-spraying system can include two compartments, one for a use solution of the medium chain peroxycarboxylic acid composition (e.g., at an acidic pH) and another for the use solution of the neutral or alkaline composition. The neutral or alkaline composition can include, for example, non-caustic alkalinity such as $K_3PO_4$, $K_2CO_3$, or monoethanol amine. Co-spraying the source of alkalinity can increase the pH of the cleaning composition to, for example, the neutral or alkaline ranges or values described herein. In embodiment, co-spraying can apply a foaming composition.

In an embodiment, for example for spray cleaning degreasing, the method can include varying the mixture applied by co-spraying. For example, the mixture can be varied to suit the soil to be removed. More polymerized grease and/or baked on soil can use a higher proportion of alkali, while a less polymerized grease and/or less baked on soil can use a lower proportion of alkali. When more soil penetration is desired, the method can first apply acid pH medium chain peroxycarboxylic acid composition and then apply source of alkalinity.

In an embodiment, the present method employing the medium chain peroxycarboxylic acid composition can include applying an acid pH medium chain peroxycarboxylic acid composition to a soiled object and applying a neutral or alkaline medium chain peroxycarboxylic acid composition to the soiled object. For example, the acid pH medium chain peroxycarboxylic acid composition can be applied to a floor or a carpet. The acid pH medium chain peroxycarboxylic acid composition can reduce the population of a microbe (e.g., sanitize or disinfect) on the floor or carpet. Subsequently, the method can include applying neutral or alkaline medium chain peroxycarboxylic acid composition to the floor or carpet. The neutral or alkaline medium chain peroxycarboxylic acid composition can clean the floor or carpet. The method can include applying the acid pH composition and the neutral or alkaline composition sequentially during a single shift (e.g., 8 hour period). The method can include applying the acid pH composition and the neutral or alkaline composition on alternate days.

In an embodiment, the present method can include reducing the population of one or more microbes, such as *Mycobacterium bovis*, bacterial spores, or fungal spores. Such antimicrobial activity can be obtained by employing a neutral pH medium chain peroxycarboxylic acid composition. In an embodiment, the present method or composition can provide faster antimicrobial action (e.g., disinfection) at a lower concentration than glutaraldehyde or peracetic acid.

In an embodiment, the present method can include removing biofilm. A method for removing biofilm can include applying an acid pH medium chain peroxycarboxylic acid composition to a biofilm. For example, the composition can be introduced into pipes or vessels in a plant, such as a food processing plant. The pipes or vessels can be subjected to cleaning-in-place (CIP). Upon applying, the composition can be allowed to contact the biofilm soiled object for a predetermined amount of time. The amount of time can be sufficient to allow the composition to penetrate biofilm. The method can include penetrating the biofilm with the composition.

This embodiment of the method also includes applying a source of alkalinity to the biofilm soiled object or to the composition contacting the biofilm soiled object. The source of alkalinity can include a buffer or alkaline component. This embodiment of the method can include applying a buffer or alkaline component to the composition already contacting the biofilm soiled object. Applying the source of alkalinity can increase the pH of the cleaning composition to, for example, the neutral or alkaline ranges or values described herein. Alternatively, the buffer or alkaline component can be used to treat the biofilm prior to the addition of the medium chain peroxycarboxylic composition In an embodiment, the present composition can include buffer or alkaline component segregated from the peroxycarboxylic acid in a single product. This can be accomplished in a solid product or by encapsulation or other system in a liquid product. The buffer or alkaline component can be allowed to mix with the peroxycarboxylic acid when diluted for use.

A composition employed in the method of the present invention can include any of a variety of effective amounts of acid pH medium chain peroxycarboxylic acid composition. In certain embodiments, the present method can employ a composition including about 0.5 to about 10 wt-% acid pH medium chain peroxycarboxylic acid composition, about 1 to about 5 wt-% acid pH medium chain peroxycarboxylic acid composition, or about 1.5 to about 3 wt-% acid pH medium chain peroxycarboxylic acid composition. In certain embodiments, the present method can employ a composition including about 0.5, 1, 1.5, 2, 2.5, 3, 3.5, 4, 4.5, or 5 wt-% acid pH medium chain peroxycarboxylic acid composition. The method can employ or the composition can include these amounts or ranges not modified by about.

Source of Alkalinity

The present composition can include and the present method can employ a source of alkalinity. Any of a variety of sources of alkalinity suitable for providing pH of the cleaning composition at the neutral or alkaline ranges or values described herein can be included or employed. Suitable sources of alkalinity include hydroxide salt, phosphate salt, carbonate salt, borate salt, silicate salt, phosphonate salt, amine, mixtures thereof, of the like. Suitable sources of alkalinity include alkali metal hydroxide, alkali metal phosphate, alkali metal carbonate, alkali metal borate, alkali metal silicate, alkali metal phosphonate, amine, mixtures thereof, of the like. For example, the source of alkalinity can be an alkali metal hydroxide, such as sodium hydroxide or potassium hydroxide, mixtures thereof, of the like. For example, suitable sources of alkalinity include non-caustic alkalinity such as alkali metal phosphate, alkali metal carbonate, alkali metal borate, alkali metal silicate, alkali metal phosphonate, amine, mixtures thereof, of the like. Suitable sources of non-caustic alkalinity include, for example, $K_3PO_4$, $K_2CO_3$, monoethanol amine, mixtures thereof, of the like. Suitable amines include alkanol amines, such as monoethanol amine, diethanolamine, triethanolamine, and monoisopropanolamine.

Examples of suitable alkalinity sources include alkali metal salts, acid salts (e.g., weak acid salts), inorganic alkalinity sources, and the like. Some examples of alkali metal salts include alkali metal carbonate, alkali metal silicate, alkali metal phosphate, alkali metal phosphonate, alkali metal sulfate, alkali metal borate, or the like, and mixtures thereof. Suitable alkali metal carbonates include sodium or potassium carbonate, sodium or potassium bicarbonate, sodium or potassium sesquicarbonate, mixtures thereof, and the like; such as sodium carbonate, potassium carbonate, or mixtures thereof.

Suitable inorganic alkalinity sources include alkali metal hydroxide, alkali metal silicate, or the like. Examples of useful alkaline metal silicates include sodium or potassium silicate (for example, with a $M_2O:SiO_2$ ratio of 1:2.4 to 5:1, M representing an alkali metal) or sodium or potassium metasilicate.

A composition employed in the method of the present invention can include 0.5, 1, 1.5, 2, 2.5, 3, 3.5, 4, 4.5, or 5 wt-% source of alkalinity. In certain embodiments, the present composition can include about an amount of source of alkalinity sufficient to achieve pH 6 in a use composition to about 10 wt-% source of alkalinity, about 0.05 to about 10 wt-% source of alkalinity, about 0.3 to about 5 wt-% source of alkalinity, or about 0.5 to about 2.5 wt-% source of alkalinity. The method can employ or the composition can include these amounts or ranges not modified by about.

EMBODIMENTS OF THE PRESENT COMPOSITIONS AND METHODS

Although not limiting to the present invention, it is believed that neutral or alkaline medium chain peroxycarboxylic acid compositions can provide, in some embodiments, certain advantages. For example, it is believed that the anion of the medium chain peroxycarboxylic acid can provide advantageous surface or interfacial activity. Certain embodiments of the neutral or alkaline medium chain peroxycarboxylic acid compositions can provide low foam compositions. It is believed that the anion of the medium chain peroxycarboxylic acid can complex $Ca^{++}$ and $Mg^{++}$ ions that can be found in service water and that such complexes are defoaming.

Certain embodiments of the neutral or alkaline medium chain peroxycarboxylic acid compositions can provide decreased odor or volatility, for example, compared to lower peroxycarboxylic acid compositions, such as peroxyacetic or peroxypropionic acid. For example, the present medium chain peroxycarboxylic acid compositions exhibited much reduced odor as compared to peracetic acid use solutions in evaporator and pasteurizer cleaning. In an embodiment, for example, the present compositions produced virtually no odor at pH>5. At such a pH, the medium chain peroxycarboxylic acid is largely ionized and can be in the form of an alkali metal salt, such as sodium or potassium salt. The salt is less volatile and malodorous than the acid.

Although not limiting to the present invention, it is believed that heat, oxidizing radicals, and/or bubbles can be produced by mixing an alkaline composition with an acid pH medium chain peroxycarboxylic acid composition. Generation of heat, oxidizing radicals, and/or bubbles can enhance soil removal.

Although not limiting to the present invention, it is believed that cleaning by the present medium chain peroxycarboxylic acid compositions can be increased by increasing the pH of the composition to about or above the $pK_a$ of the peroxycarboxylic acid. Although not limiting to the present invention, it is believed that cleaning by the present medium chain peroxycarboxylic acid compositions can be increased by increasing the pH of the composition to about or above the $pK_a$ of hydrogen peroxide. It is believed that at pH<<pKa, of the peroxycarboxylic acid or of the hydrogen peroxide there are not enough peranions to increase cleaning, but that at pH>>pKa, the peranions are unstable and do not last long enough for increasing cleaning.

Although not limiting to the present invention, it is believed that at about pH 6.5 the present medium chain peroxycarboxylic acid compositions can provide advantageous antimicrobial activity and suitable cleaning. In an embodiment, a pH 6.5 composition can be employed, for example, for non-corrosive high level disinfection or for disinfection of a heat sensitive medical device.

Although not limiting to the present invention, it is believed that at about pH 8.7 the present medium chain peroxycarboxylic acid compositions can provide antimicrobial activity and advantageous cleaning. In an embodiment, a pH 8.7 composition can be employed, for example, for non-corrosive cleaning of a heat sensitive medical device. The pKa of the peroxycarboxylic acid is about 8.7. In an embodiment, one step cleaning and disinfection can be achieved at about this pH.

Although not limiting to the present invention, it is believed that at about pH 11.8 the present medium chain peroxycarboxylic acid compositions can provide advantageous cleaning. In an embodiment, a pH 11.8 composition can be employed, for example, for biofilm removal. The pKa of hydrogen peroxide is about 11.8.

In certain embodiments, the present neutral or alkaline medium chain peroxycarboxylic acid compositions can be used according methods described herein for methods of, for example, high level disinfecting, disinfecting a heat sensitive medical device, CIP cleaning, (e.g., on heat-exchange surfaces of a pasteurizer, an evaporator, or the like), machine ware washing, oven cleaning, hard surface cleaning, degreasing, parts cleaning, food preparation area cleaning, cleaning meat and poultry preparation areas, and smoke house cleaning.

In certain embodiments, the present composition can be used as a non-corrosive disinfectant, sporicide, fungicide, virucide, or insecticide. The present compositions can be used as a non-corrosive odor control agent. The present compositions can be used as a non-corrosive sanitizer (e.g., carpet sanitizer or laundry sanitizer). The present compositions can be used as a non-corrosive bleaching agent. Of course, each of these uses can be a method employing the present compositions.

In certain embodiments, the present compositions can be used as a broad spectrum disinfectant or sanitizer or as a destaining rinse aid.

In certain embodiments, the present compositions can be employed for cleaning heat transfer surfaces, such as heat transfer surfaces in food processing facilities (e.g., tomato, citrus fruit, salt brine and sugar beet processing), heat transfer surfaces in distillation and corn ethanol processing facilities.

Foaming the Compositions

In an embodiment of the present invention, the method can include applying the composition to an object by foaming. The foam can be prepared by mixing foaming surfactants with and applying the peroxycarboxylic acid composition, the alkaline composition, or the neutral or alkaline medium chain peroxycarboxylic acid composition at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. Use solution levels of the foaming agents is from about 50 ppm to about 2.0 wt-%. At time of use, compressed air can be injected into the mixture, then applied to the object through a foam application device such as a tank foamer or an aspirated wall mounted foamer.

Medium Chain Peroxycarboxylic Acid Antimicrobial Compositions

The present invention includes medium chain peroxycarboxylic acid compositions. The present medium chain peroxycarboxylic acid compositions can include increased levels of medium chain peroxycarboxylic acid compared to conventional peroxycarboxylic acid compositions. The inventive compositions can include medium chain peroxycarboxylic acid and a solubilizer. The solubilizer can increase or maintain the solubility of the medium chain peroxycarboxylic acid. The present medium chain peroxycarboxylic acid compositions can include a microemulsion or a surfactant that can form a microemulsion. The present medium chain peroxycarboxylic acid compositions need not include substantial amounts of short chain carboxylic acid, short chain peroxycarboxylic acid, or mixture thereof. It is believed that, in conventional mixed peroxycarboxylic acid compositions, the short chain carboxylic acid, short chain peroxycarboxylic acid, or mixture thereof can solubilize medium chain peroxycarboxylic acid. The compositions can be referred to as "acid pH".

In an embodiment, the present compositions include medium chain peroxycarboxylic acid. These compositions can also include medium chain carboxylic acid. Such compositions can include advantageously high levels of medium chain peroxycarboxylic acid. In an embodiment, the present compositions include about 2 or more parts by weight of medium chain peroxycarboxylic acid for each 7 parts by weight of medium chain carboxylic acid. In an embodiment, the present compositions include about 2 or more parts by weight of medium chain peroxycarboxylic acid for each 6 parts by weight of medium chain carboxylic acid. In an embodiment, the present compositions include about 2 or more parts by weight of medium chain peroxycarboxylic acid for each 5 parts by weight of medium chain carboxylic acid. In an embodiment, the present compositions include about 2 or more parts by weight of medium chain peroxycarboxylic acid for each 4 parts by weight of medium chain carboxylic acid. In an embodiment, the present compositions include about 2 parts by weight of medium chain peroxycarboxylic acid for each 3 parts by weight of medium chain carboxylic acid.

In an embodiment, the present compositions include medium chain peroxycarboxylic acid and solubilizer. The solubilizer can include a solvent, a surfactant, or a mixture thereof. Suitable solvents include any of a variety of solvents that solubilize and do not significantly degrade the medium chain peroxycarboxylic acid. In certain embodiments, suitable solvents include polyalkylene oxide, capped polyalkylene oxide, mixtures thereof, or the like. Suitable solvents include nonionic surfactant, such as alkoxylated surfactant. Suitable alkoxylated surfactants include, for example, EO/PO copolymer, capped EO/PO copolymer, alcohol alkoxylate, capped alcohol alkoxylate, mixtures thereof, or the like. When employed as a solvent a surfactant, such as a nonionic surfactant, can be at concentrations higher than those conventionally employed.

The solubilizer can include surfactant (e.g., microemulsion forming surfactant). Suitable surfactants include anionic surfactant, nonionic surfactant, cationic surfactant, amphoteric surfactant, zwitterionic surfactant, mixtures thereof, or the like. The solubilizer can include a microemulsion forming surfactant. Suitable microemulsion forming surfactants include anionic surfactant, cationic surfactant, amphoteric surfactant, zwitterionic surfactant, mixtures thereof, or the like. Suitable microemulsion forming surfactants include anionic surfactants, such as sulfate surfactant, sulfonate surfactant, phosphate surfactant (phosphate ester surfactant), and carboxylate surfactant, mixtures thereof, or the like.

In an embodiment, the present composition need not include substantial amounts of short chain peroxycarboxylic acid. For example, the present compositions can be free of added short chain peroxycarboxylic acid. As used herein, free of added material refers to a composition that includes the material only as a incidental or trace quantity found, for example, as an ingredient of or impurity in another named ingredient or incidentally generated from a minor side reaction.

In an embodiment, the present composition includes only relatively small amounts of short chain peroxycarboxylic acid. For example, the present composition can include about 1 or more parts of medium chain peroxycarboxylic acid for each 8 parts of short chain carboxylic acid, short chain peroxycarboxylic acid, or mixture thereof. For example, the present composition can include short chain peroxycarboxylic acid at a level insufficient to cause odor offensive to a typical person.

In certain embodiments, the present composition does not include substantial amounts of peroxyacetic acid, is free of added peroxyacetic acid, includes about 1 or more parts of medium chain peroxycarboxylic acid for each 8 parts of peroxyacetic acid, or includes peroxyacetic acid at a level insufficient to cause odor offensive to a typical person.

In an embodiment, the present composition need not include substantial amounts of short chain carboxylic acid.

For example, the present compositions can be free of added short chain carboxylic acid. In an embodiment, the present composition includes only relatively small amounts of short chain carboxylic acid. By way of further example, the present composition can include about 1 or more parts of medium chain peroxycarboxylic acid for each 8 parts of short chain carboxylic acid. For example, the present composition can include short chain carboxylic acid at a level insufficient to cause odor offensive to a typical person.

In certain embodiments, the present composition does not include substantial amounts of acetic acid, is free of added acetic acid, includes about 1 or more parts of medium chain peroxycarboxylic acid for each 8 parts of acetic acid, or includes acetic acid at a level insufficient to cause odor offensive to a typical person. In certain embodiments, the present compositions include, for example, less than 10 wt-%, less than less than 5 wt-%, less than 2 wt-%, or less than 1 wt-% acetic acid. In certain embodiments, the present use compositions include, for example, less than 40 ppm, less than 20 ppm, less than 10 ppm, or less than 5 ppm acetic acid.

In an embodiment, the present composition need not include substantial amounts of short chain peroxycarboxylic acid, short chain carboxylic acid, or mixture thereof. For example, the present compositions can be free of added short chain peroxycarboxylic acid, short chain carboxylic acid, or mixture thereof. For example, the present composition can include short chain carboxylic acid, short chain peroxycarboxylic acid, or mixture thereof at a level insufficient to cause odor offensive to a typical person. In certain embodiments, the present composition does not include substantial amounts of acetic acid, peroxyacetic acid, or mixtures thereof; is free of added acetic acid, peroxyacetic acid, or mixtures thereof; includes about 1 or more parts of medium chain peroxycarboxylic acid for each 8 parts of acetic acid, peroxyacetic acid, or mixtures thereof; or includes acetic acid, peroxyacetic acid, or mixtures thereof at a level insufficient to cause odor offensive to a typical person.

In an embodiment, the present composition includes about 1 or more parts of medium chain peroxycarboxylic acid for each 8 parts of short chain carboxylic acid, short chain peroxycarboxylic acid, or mixture thereof. In an embodiment, the present composition includes about 1 or more parts of medium chain peroxycarboxylic acid for each 7 parts of short chain carboxylic acid, short chain peroxycarboxylic acid, or mixture thereof. In an embodiment, the present composition includes about 1 or more parts of medium chain peroxycarboxylic acid for each 6 parts of short chain carboxylic acid, short chain peroxycarboxylic acid, or mixture thereof. In an embodiment, the present composition includes about 1 or more parts of medium chain peroxycarboxylic acid for each 5 parts of short chain carboxylic acid, short chain peroxycarboxylic acid, or mixture thereof. In an embodiment, the present composition includes about 1 or more parts of medium chain peroxycarboxylic acid for each 4 parts of short chain carboxylic acid, short chain peroxycarboxylic acid, or mixture thereof. In an embodiment, the present composition includes about 1 or more parts of medium chain peroxycarboxylic acid for each 3 parts of short chain carboxylic acid, short chain peroxycarboxylic acid, or mixture thereof. In an embodiment, the present composition includes about 1 or more parts of medium chain peroxycarboxylic acid for each 2 parts of short chain carboxylic acid, short chain peroxycarboxylic acid, or mixture thereof. In an embodiment, the present composition includes about 1 or more parts of medium chain peroxycarboxylic acid for each 1 part of short chain carboxylic acid, short chain peroxycarboxylic acid, or mixture thereof.

In an embodiment, the present composition has an odor less unpleasant than (e.g., as measured by an hedonic tone rating) than 5, 4, 3, 2, or 1 wt-% acetic acid in water. In an embodiment, the present composition has an odor less unpleasant than (e.g., as measured by an hedonic tone rating) than 5 wt-% acetic acid in water. In an embodiment, the present composition has an odor less unpleasant than (e.g., as measured by an hedonic tone rating) than 4 wt-% acetic acid in water. In an embodiment, the present composition has an odor less unpleasant than (e.g., as measured by an hedonic tone rating) than 3 wt-% acetic acid in water. In an embodiment, the present composition has an odor less unpleasant than (e.g., as measured by an hedonic tone rating) than 2 wt-% acetic acid in water. In an embodiment, the present composition has an odor with an odor less unpleasant than (e.g., as measured by an hedonic tone rating) than 1 wt-% acetic acid in water.

In certain embodiments, the present composition includes one or more (e.g., at least one) of oxidizing agent, acidulant, stabilizing agent, mixtures thereof, or the like. The present composition can include any of a variety of oxidizing agents, for example, hydrogen peroxide. The oxidizing agent can be effective to convert a medium chain carboxylic acid to a medium chain peroxycarboxylic acid. The oxidizing agent can also have antimicrobial activity, although it may not be present at a concentration sufficient to exhibit such activity. The present composition can include any of a variety of acidulants, for example, an inorganic acid. The acidulant can be effective to bring the pH of the present concentrate composition to less than 1, or to bring the pH of the present use composition to about 5 or below, about 4 or below, or about 3 or below. The acidulant can augment the antimicrobial activity of the present composition. The present composition can include any of a variety of stabilizing agents, for example, sequestrant, for example, phosphonate sequestrant. The sequestrant can be effective to stabilize the peroxycarboxylic acid.

In an embodiment, the present composition exhibits advantageous stability of the peroxycarboxylic acid. It is believed that in approximately one year at ambient conditions or room temperature (or 1 week at 60° C.) the amount of peroxycarboxylic acid in the compositions can be about 80% or more, about 85% or more, about 90% or more, or about 95% or more of the initial values or use composition levels. Such aged compositions are included in the scope of the present invention.

In an embodiment, the present composition exhibits advantageous efficacy compared to other antimicrobial compositions at the same level of active. In certain embodiments, the present composition has reduced or no volatile organic compounds compared to conventional peroxycarboxylic acid compositions. In an embodiment, the present composition has a higher flash point compared to conventional peroxycarboxylic acid compositions. In an embodiment, the present composition exhibits improved operator or user safety compared to conventional peroxycarboxylic acid compositions. In an embodiment, the present composition exhibits improved storage or transportation safety compared to conventional peroxycarboxylic acid compositions.

In certain embodiments, the present composition includes about 0.0005 to about 5 wt-% medium chain peroxycarboxylic acid, about 0.3 to about 7 wt-% medium chain peroxycarboxylic acid, about 0.5 to about 5 wt-% medium chain peroxycarboxylic acid, about 0.5 to about 4 wt-% medium chain peroxycarboxylic acid, about 0.8 to about 3 wt-% medium chain peroxycarboxylic acid, about 1 to about 3 wt-% medium chain peroxycarboxylic acid, or about 1 to about 2 wt-% medium chain peroxycarboxylic acid. The composition can include any of these ranges or amounts not modified by about.

In certain embodiments, the present composition includes about 0.001 to about 8 wt-% medium chain carboxylic acid, about 1 to about 10 wt-% medium chain carboxylic acid, about 1 to about 8 wt-% medium chain carboxylic acid, about 1.5 to about 6 wt-% medium chain carboxylic acid, about 2 to about 8 wt-% medium chain carboxylic acid, about 2 to about 6 wt-% medium chain carboxylic acid, about 2 to about 4 wt-% medium chain carboxylic acid, about 2.5 to about 5 wt-% medium chain carboxylic acid, about 3 to about 6 wt-% medium chain carboxylic acid, or about 3 to about 5 wt-% medium chain carboxylic acid. The composition can include any of these ranges or amounts not modified by about.

In certain embodiments, the present composition includes about 0 to about 98 wt-% carrier, about 0.001 to about 99.99 wt-% carrier, about 0.2 to about 60 wt-% carrier, about 1 to about 98 wt-% carrier, about 5 to about 99.99 wt-% carrier, about 5 to about 97 wt-% carrier, about 5 to about 90 wt-% carrier, about 5 to about 70 wt-% carrier, about 5 to about 20 wt-% carrier, about 10 to about 90 wt-% carrier, about 10 to about 80 wt-% carrier, about 10 to about 50 wt-% carrier, about 10 to about 20 wt-% carrier, about 15 to about 70 wt-% carrier, about 15 to about 80 wt-% carrier, about 20 to about 70 wt-% carrier, about 20 to about 50 wt-% carrier, about 20 to about 40 wt-% carrier, about 20 to about 30 wt-% carrier, about 30 to about 75 wt-% carrier, about 30 to about 70 wt-% carrier, about 40 to about 99.99 wt-% carrier, about 40 to about 90 wt-% carrier, or about 60 to about 70 wt-% carrier. The composition can include any of these ranges or amounts not modified by about.

In certain embodiments, the present composition includes about 0.001 to about 80 wt-% solubilizer, about 0.001 to about 60 wt-% solubilizer, about 1 to about 80 wt-% solubilizer, about 1 to about 25 wt-% solubilizer, about 1 to about 20 wt-% solubilizer, about 2 to about 70 wt-% solubilizer, about 2 to about 60 wt-% solubilizer, about 2 to about 20 wt-% solubilizer, about 3 to about 65 wt-% solubilizer, about 3 to about 15 wt-% solubilizer, about 4 to about 10 wt-% solubilizer, about 4 to about 20 wt-% solubilizer, about 5 to about 70 wt-% solubilizer, about 5 to about 60 wt-% solubilizer, about 5 to about 20 wt-% solubilizer, about 10 to about 70 wt-% solubilizer, about 10 to about 65 wt-% solubilizer, about 10 to about 20 wt-% solubilizer, about 20 to about 60 wt-% solubilizer, or about 40 to about 60 wt-% solubilizer. The composition can include any of these ranges or amounts not modified by about.

In certain embodiments, the present composition includes about 0.001 to about 30 wt-% oxidizing agent, about 0.001 to about 10 wt-% oxidizing agent, 0.002 to about 10 wt-% oxidizing agent, about 2 to about 70 wt-% oxidizing agent, about 2 to about 60 wt-% oxidizing agent, about 2 to about 50 wt-% oxidizing agent, about 2 to about 40 wt-% oxidizing agent, about 2 to about 30 wt-% oxidizing agent, about 2 to about 25 wt-% oxidizing agent, about 2 to about 20 wt-% oxidizing agent, about 4 to about 20 wt-% oxidizing agent, about 5 to about 10 wt-% oxidizing agent, or about 6 to about 10 wt-% oxidizing agent. The composition can include any of these ranges or amounts not modified by about.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

In certain embodiments, the present composition includes about 0.001 to about 50 wt-% stabilizing agent, about 0.001 to about 5 wt-% stabilizing agent, about 0.5 to about 50 wt-% stabilizing agent, about 1 to about 50 wt-% stabilizing agent, about 1 to about 30 wt-% stabilizing agent, about 1 to about 10 wt-% stabilizing agent, about 1 to about 5 wt-% stabilizing agent, about 1 to about 3 wt-% stabilizing agent, about 2 to about 10 wt-% stabilizing agent, about 2 to about 5 wt-% stabilizing agent, or about 5 to about 15 wt-% stabilizing agent. The composition can include any of these ranges or amounts not modified by about.

Compositions of Medium Chain Carboxylic Acids and/or Peroxycarboxylic Acids

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted. The composition and methods of the invention can employ medium chain peroxycarboxylic acids containing, for example, 6 to 12 carbon atoms. For example, medium chain peroxycarboxylic (or percarboxylic) acids can have the formula $R(CO_3H)_n$, where R is a $C_5$-$C_{11}$ alkyl group, a $C_5$-$C_{11}$ cycloalkyl, a $C_5$-$C_{11}$ arylalkyl group, $C_5$-$C_{11}$ aryl group, or a $C_5$-$C_{11}$ heterocyclic group; and n is one, two, or three.

Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide. In an embodiment, the medium chain percarboxylic acids can be made by the direct, acid catalyzed equilibrium action of hydrogen peroxide on the medium chain carboxylic acid. Scheme 1 illustrates an equilibrium between carboxylic acid and oxidizing agent (Ox) on one side and peroxycarboxylic acid and reduced oxidizing agent ($Ox_{red}$) on the other:

$$RCOOH + Ox \leftrightarrows RCOOOH + Ox_{red} \quad (1)$$

Scheme 2 illustrates an embodiment of the equilibrium of scheme 1 in which the oxidizing agent is hydrogen peroxide on one side and peroxycarboxylic acid and water on the other:

$$RCOOH + H_2O_2 \leftrightarrows RCOOOH + H_2O \quad (2)$$

In conventional mixed peroxycarboxylic acid compositions it is believed that the equilibrium constant for the reaction illustrated in scheme 2 is about 2.5, which may reflect the equilibrium for acetic acid. Although not limiting to the present invention, it is believed that the present compositions have an equilibrium constant of about 4.

Peroxycarboxylic acids useful in the compositions and methods of the present invention include peroxypentanoic, peroxyhexanoic, peroxyheptanoic, peroxyoctanoic, peroxynonanoic, peroxyisononanoic, peroxydecanoic, peroxyundecanoic, peroxydodecanoic, peroxyascorbic, peroxyadipic, peroxycitric, peroxypimelic, or peroxysuberic acid, mixtures thereof, or the like. The alkyl backbones of these medium chain peroxycarboxylic acids can be straight chain, branched, or a mixture thereof. Peroxy forms of carboxylic acids with more than one carboxylate moiety can have one or more (e.g., at least one) of the carboxyl moieties present as peroxycarboxyl moieties.

Although not limiting to the present invention, it is believed that branched chain medium chain peroxycarboxylic acid can contribute to defoaming the composition. Branched chain peroxycarboxylic acids useful in the compositions and methods of the present invention include peroxyisopentanoic, peroxyisohexanoic, peroxyisoheptanoic, peroxyisooctanoic, peroxyisononanoic, peroxyisodecanoic, peroxyisoundecanoic, peroxyisododecanoic, peroxyneopentanoic, peroxyneohexanoic, peroxyneoheptanoic, peroxyneooctanoic, peroxyneononanoic, peroxyneodecanoic, peroxyneoundecanoic, peroxyneododecanoic, mixtures thereof, or the like. Suitable branched chain medium chain peroxycarboxylic acids include peroxyisononanoic acid.

Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid is surface active and can assist in wetting hydrophobic surfaces, such as those of microbes.

The composition of the present invention can include a carboxylic acid. Generally, carboxylic acids have the formula R—COOH wherein the R can represent any number of different groups including aliphatic groups, alicyclic groups, aromatic groups, heterocyclic groups, all of which can be saturated or unsaturated as well as substituted or unsubstituted. Carboxylic acids can have one, two, three, or more carboxyl groups. The composition and methods of the invention typically employ medium chain carboxylic acids containing, for example, 6 to 12 carbon atoms. For example, medium chain carboxylic acids can have the formula R—COOH in which R can be a $C_5$-$C_{11}$ alkyl group, a $C_5$-$C_{11}$ cycloalkyl group, a $C_5$-$C_{11}$ arylalkyl group, $C_5$-$C_{11}$ aryl group, or a $C_5$-$C_{11}$ heterocyclic group.

Suitable medium chain carboxylic acids include pentanoic, hexanoic, heptanoic, octanoic, nonanoic, decanoic, undecanoic, dodecanoic, ascorbic, citric, adipic, pimelic, and suberic acid. The alkyl backbones of these medium chain carboxylic acids can be straight chain, branched, or a mixture thereof. Carboxylic acids which are generally useful are those having one or two carboxyl groups where the R group is a primary alkyl chain having a length of $C_4$ to $C_{11}$. The primary alkyl chain is that carbon chain of the molecule having the greatest length of carbon atoms and directly appending carboxyl functional groups.

Although not limiting to the present invention, it is believed that branched chain medium chain carboxylic acid can contribute to defoaming the composition. Branched chain carboxylic acids useful in the compositions and methods of the present invention include isopentanoic, isohexanoic, isoheptanoic, isooctanoic, isononanoic, isodecanoic, isoundecanoic, isododecanoic, neopentanoic, neohexanoic, neoheptanoic, neooctanoic, neononanoic, neodecanoic, neoundecanoic, neododecanoic, mixtures thereof, or the like. Suitable branched chain medium chain carboxylic acids include isononanoic acid.

The present compositions and methods include a medium chain peroxycarboxylic acid. The medium chain peroxycarboxylic acid can include or be a C6 to C12 peroxycarboxylic acid. The C6 to C12 peroxycarboxylic acid can include or be peroxyhexanoic acid, peroxyheptanoic acid, peroxyoctanoic acid, peroxynonanoic acid, peroxyisononanoic acid, peroxydecanoic acid, peroxyundecanoic acid, peroxydodecanoic acid, or mixture thereof. The medium chain peroxycarboxylic acid can include or be a C7 to C12 peroxycarboxylic acid. The C7 to C12 peroxycarboxylic acid can include or be peroxyheptanoic acid, peroxyoctanoic acid, peroxynonanoic acid, peroxyisononanoic acid, peroxydecanoic acid, peroxyundecanoic acid, peroxydodecanoic acid, or mixture thereof. The medium chain peroxycarboxylic acid can include or be a C6 to C10 peroxycarboxylic acid. The C6 to C10 peroxycarboxylic acid can include or be peroxyhexanoic acid, peroxyheptanoic acid, peroxyoctanoic acid, peroxynonanoic acid, peroxyisononanoic acid, peroxydecanoic acid, or mixture thereof. The medium chain peroxycarboxylic acid can include or be a C8 to C10 peroxycarboxylic acid. The C8 to C10 peroxycarboxylic acid can include or be peroxyoctanoic acid, peroxynonanoic acid, peroxyisononanoic acid, peroxydecanoic acid, or mixture thereof. In certain embodiments, the medium chain peroxyoctanoic acid includes or is peroxyoctanoic acid, peroxydecanoic acid, or mixture thereof. In an embodiment, the medium chain peroxycarboxylic acid includes or is peroxyoctanoic acid.

In certain embodiments, the present composition includes about 0.0005 to about 5 wt-% medium chain peroxycarboxylic acid, about 0.3 to about 7 wt-% medium chain peroxycarboxylic acid, about 0.5 to about 5 wt-% medium chain peroxycarboxylic acid, about 0.5 to about 4 wt-% medium chain peroxycarboxylic acid, about 0.8 to about 3 wt-% medium chain peroxycarboxylic acid, about 1 to about 3 wt-% medium chain peroxycarboxylic acid, or about 1 to about 2 wt-% medium chain peroxycarboxylic acid. The composition can include any of these ranges or amounts not modified by about.

In an embodiment, the present compositions and methods include a medium chain carboxylic acid. The medium chain carboxylic acid can include or be a C6 to C12 carboxylic acid. The C6 to C12 carboxylic acid can include or be hexanoic acid, heptanoic acid, octanoic acid, nonanoic acid, isononanoic acid, decanoic acid, undecanoic acid, dodecanoic acid, or mixture thereof. The medium chain carboxylic acid can include or be a C7 to C12 carboxylic acid. The C7 to C12 carboxylic acid can include or be heptanoic acid, octanoic acid, nonanoic acid, isononanoic acid, decanoic acid, undecanoic acid, dodecanoic acid, or mixture thereof. The medium chain peroxycarboxylic acid can include or be a C6 to C10 carboxylic acid. The C6 to C10 carboxylic acid can include or be hexanoic acid, heptanoic acid, octanoic acid, nonanoic acid, isononanoic acid, decanoic acid, or mixture thereof. The medium chain carboxylic acid can include or be a C8 to C10 carboxylic acid. The C8 to C10 carboxylic acid can include or be octanoic acid, nonanoic acid, isononanoic acid, decanoic acid, or mixture thereof. In certain embodiments, the medium chain carboxylic acid includes or is octanoic acid, decanoic acid, or mixture thereof. In an embodiment, the medium chain carboxylic acid includes or is octanoic acid.

In certain embodiments, the present composition includes about 0.001 to about 8 wt-% medium chain carboxylic acid, about 1 to about 10 wt-% medium chain carboxylic acid, about 1 to about 8 wt-% medium chain carboxylic acid, about 1.5 to about 6 wt-% medium chain carboxylic acid, about 2 to about 8 wt-% medium chain carboxylic acid, about 2 to about 6 wt-% medium chain carboxylic acid, about 2 to about 4 wt-% medium chain carboxylic acid, about 2.5 to about 5 wt-% medium chain carboxylic acid, about 3 to about 6 wt-% medium chain carboxylic acid, or about 3 to about 5 wt-% medium chain carboxylic acid. The composition can include any of these ranges or amounts not modified by about.

In an embodiment, the compositions and methods include a medium chain peroxycarboxylic acid and the corresponding medium chain carboxylic acid.

In an embodiment, the present composition includes an amount of medium chain peroxycarboxylic acid effective for killing one or more (e.g., at least one) of the food-borne pathogenic bacteria associated with a food product, such as *Salmonella typhimurium, Salmonella javiana, Campylobacter jejuni, Listeria monocytogenes*, and *Escherichia coli* O157:H7, yeast, mold, and the like. In an embodiment, the present composition includes an amount of medium chain peroxycarboxylic acid effective for killing one or more (e.g., at least one) of the pathogenic bacteria associated with a health care surfaces and environments, such as *Salmonella typhimurium, Staphylococcus aureus, Salmonella choleraesurus, Pseudomonas aeruginosa, Escherichia coli*, mycobacteria, yeast, mold, and the like. The compositions and methods of the present invention have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

Embodiments of the present invention include medium chain carboxylic acid and medium chain peroxycarboxylic acid, and certain embodiments specifically exclude short chain peroxycarboxylic acid, short chain carboxylic acid, or mixture thereof. Nonetheless embodiments of the present compositions can include short chain peroxycarboxylic acid, short chain carboxylic acid, or mixture thereof. It is not intended that addition of short chain peroxycarboxylic acid, short chain carboxylic acid, or mixture thereof to a composition should necessarily take a composition outside the spirit and scope of the present invention.

Solubilizers

The present compositions can include a solubilizer. The present invention relates to solubilizers for medium chain carboxylic acids and medium chain peroxycarboxylic acids. In an embodiment, the solubilizer can increase or maintain the solubility in the composition of the medium chain peroxycarboxylic acid or the medium chain carboxylic acid. The present compositions and methods can include any of a variety of suitable solubilizers. For example, the solubilizer can include a solvent, a surfactant, or a mixture thereof. In an embodiment, the surfactant can be employed as a solvent. In an embodiment, the surfactant can form a microemulsion. In an embodiment, the composition including the present solubilizer takes the form of a viscoelastic gel or liquid. In an embodiment, the solubilizer is effective to dissolve octanoic acid at a concentration of 5 wt-% in water. In an embodiment, the solubilizer is effective to dissolve octanoic acid at a concentration of 4 wt-% in water. In an embodiment, the solubilizer is effective to dissolve octanoic acid at a concentration of 3 wt-% in water. In an embodiment, the solubilizer is effective to dissolve octanoic acid at a concentration of 2 wt-% in water.

In certain embodiments, the present composition includes about 0.001 to about 80 wt-% solubilizer, about 0.001 to about 60 wt-% solubilizer, about 1 to about 80 wt-% solubilizer, about 1 to about 25 wt-% solubilizer, about 1 to about 20 wt-% solubilizer, about 2 to about 70 wt-% solubilizer, about 2 to about 60 wt-% solubilizer, about 2 to about 20 wt-% solubilizer, about 3 to about 65 wt-% solubilizer, about 3 to about 15 wt-% solubilizer, about 4 to about 10 wt-% solubilizer, about 4 to about 20 wt-% solubilizer, about 5 to about 70 wt-% solubilizer, about 5 to about 60 wt-% solubilizer, about 5 to about 20 wt-% solubilizer, about 10 to about 70 wt-% solubilizer, about 10 to about 65 wt-% solubilizer, about 10 to about 20 wt-% solubilizer, about 20 to about 60 wt-% solubilizer, or about 40 to about 60 wt-% solubilizer. The composition can include any of these ranges or amounts not modified by about.

Solvent Solubilizers and Compositions Including Them

In an embodiment, the present compositions and methods can include as solubilizer one or more (e.g., at least one) solvents. Suitable solvents include any of a variety of solvents that solubilize but do not significantly degrade the medium chain peroxycarboxylic acid. Suitable solvents include polyalkylene oxide, capped polyalkylene oxide, glycol ether, nonionic surfactant, mixtures thereof, or the like.

In an embodiment, the present composition includes medium chain peroxycarboxylic acid; medium chain carboxylic acid; carrier; and polyalkylene oxide, capped polyalkylene oxide, nonionic surfactant, or mixture thereof. For example, the present composition can include about 0.5 to about 5 wt-% medium chain peroxycarboxylic acid; about 1 to about 10 wt-% medium chain carboxylic acid; about 1 to about 98 wt-% carrier; and about 1 to about 80 wt-% polyalkylene oxide, capped polyalkylene oxide, nonionic surfactant, or mixture thereof. For example, the present composition can include about 0.5 to about 5 wt-% medium chain peroxycarboxylic acid; about 1 to about 10 wt-% medium chain carboxylic acid; about 5 to about 35 wt-% carrier; and about 20 to about 65 wt-% polyalkylene oxide, capped polyalkylene oxide, nonionic surfactant, or mixture thereof. For example, the present composition can include about 0.5 to about 5 wt-% medium chain peroxycarboxylic acid; about 1 to about 10 wt-% medium chain carboxylic acid; about 10 to about 35 wt-% carrier; and about 40 to about 60 wt-% polyalkylene oxide, capped polyalkylene oxide, nonionic surfactant, or mixture thereof. In an embodiment, the present composition includes solvent solubilizer and less than or equal to 35 wt-% carrier (e.g., water). The composition can include any of these ranges or amounts not modified by about.

In an embodiment, the present composition includes C8 peroxycarboxylic acid; C8 carboxylic acid; water; and polyalkylene oxide, capped polyalkylene oxide, nonionic surfactant, or mixture thereof. For example, the present composition can include about 0.5 to about 5 wt-% C8 peroxycarboxylic acid; about 1 to about 10 wt-% C8 carboxylic acid; about 1 to about 98 wt-% water; and about 1 to about 80 wt-% polyalkylene oxide, capped polyalkylene oxide, nonionic surfactant, or mixture thereof. For example, the present composition can include about 0.5 to about 5 wt-% C8 peroxycarboxylic acid; about 1 to about 10 wt-% C8 carboxylic acid; about 5 to about 35 wt-% water; and about 20 to about 65 wt-% polyalkylene oxide, capped polyalkylene oxide, nonionic surfactant, or mixture thereof. For example, the present composition can include about 0.5 to about 5 wt-% C8 peroxycarboxylic acid; about 1 to about 10 wt-% C8 carboxylic acid; about 10 to about 35 wt-% water; and about 40 to about 60 wt-% polyalkylene oxide, capped polyalkylene oxide, nonionic surfactant, or mixture thereof. The composition can include any of these ranges or amounts not modified by about.

In certain embodiments, the present composition includes about 0.001 to about 80 wt-% solvent as solubilizer, about 0.001 to about 60 wt-% solvent as solubilizer, about 1 to about 80 wt-% solvent as solubilizer, about 5 to about 70 wt-% solvent as solubilizer, about 10 to about 65 wt-% solvent as solubilizer, or about 20 to about 60 wt-% solvent as solubilizer. The composition can include any of these ranges or amounts not modified by about.

In an embodiment, when the present compositions and methods include a solvent as solubilizer, they need not include a significant amount, or even any, of a short chain peroxycarboxylic acid, a short chain carboxylic acid, or a mixture thereof. Examples of short chain carboxylic acids include formic acid, acetic acid, propionic acid, and butanoic acid. Short chain carboxylic acids and peroxycarboxylic acids include those with 4 or fewer carbon atoms. In an embodiment, the present compositions and methods including a solvent solubilizer need not include substantial amounts of short chain peroxycarboxylic acid. In an embodiment, the present compositions and methods including a solvent solubilizer can be free of added short chain peroxycarboxylic acid.

In an embodiment, the present compositions and methods including a solvent solubilizer can include medium chain peroxycarboxylic acid in greater proportion compared to the short chain peroxycarboxylic acid than found in conventional compositions. For example, the present compositions and methods can include solvent solubilizer and about 1 or more parts of medium chain peroxycarboxylic acid for each 8 parts of short chain carboxylic acid, short chain peroxycarboxylic acid, or mixture thereof. For example, the present compositions and methods can include solvent solubilizer and short chain carboxylic acid, short chain peroxycarboxylic acid, or mixture thereof at a level insufficient to cause odor offensive to a typical person.

Polyalkylene Oxide Solubilizers

Suitable polyalkylene oxides include polyethylene glycol, polypropylene glycol, polybutylene glycol, mixtures thereof, or the like. Suitable capped polyalkylene oxides include mono-alkyl and di-alkyl ethers of the respective polyalkylene oxides, such as mono- and di-methyl ethers of polyalkylene glycol, mono- and di-ethyl ethers of polyalkylene glycol, mono- and di-propyl ethers of polyalkylene glycol, mono- and di-butyl ethers of polyalkylene glycol, mixtures thereof, or the like. Suitable capped polyalkylene oxides include methyl polyethylene glycol (e.g., the monomethyl ether of polyethylene glycol), dimethyl polyethylene glycol (e.g., the dimethyl ether of polyethylene glycol), mixtures thereof, or the like.

Glycol Ether Solubilizers

Suitable solvent solubilizers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

Nonionic Surfactants

Suitable nonionic surfactants for use as solvents include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Dehypon LT 054 (C12-C18 5EO butyl capped alcohol ethoxylate), Plurafac LF221, and Tegoten EC11; mixtures thereof, or the like. When employed as a solvent a surfactant, such as a nonionic surfactant, can be at concentrations higher than those conventionally employed as surfactant.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

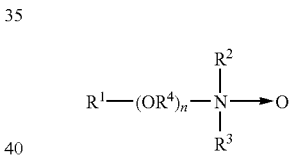

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, isododecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Surfactant Solubilizers and Compositions Including Them

In an embodiment, the present compositions and methods can include as solubilizer one or more (e.g., at least one) surfactants, e.g., a microemulsion forming surfactant. Suitable surfactants include anionic surfactant, cationic surfactant, amphoteric surfactant, zwitterionic surfactant, mixtures thereof, or the like. Suitable microemulsion forming surfactants include anionic surfactant, cationic surfactant, amphoteric surfactant, zwitterionic surfactant, mixtures thereof, or the like. Suitable microemulsion forming surfactants include anionic surfactant. A microemulsion forming surfactant can form a microemulsion in a composition including a medium chain peroxycarboxylic acid, a medium chain carboxylic acid, or a mixture thereof. In an embodiment, the present composition includes a micro emulsion.

In an embodiment, the present composition can be determined to be a microemulsion by testing the composition for being a shear thinning viscoelastic gel or liquid that has a blue tyndall appearance. Although not limiting to the present invention, blue tyndall appearance is believed to indicate a heterogeneous system of a small, suspended dispersion (e.g., a microemulsion), which is effective in scattering blue light.

In an embodiment, the present composition can be determined to be a microemulsion by testing the ability to form a physically stable composition at different concentrations of surfactant solubilizer. A microemulsion can yield a curve with a maximum of physical stability at a concentration with unstable compositions at higher and lower concentrations. Typically, mixtures of solvents and surfactants (e.g., acetic acid and surfactant) do not form microemulsions.

In an embodiment, the composition including surfactant solubilizer takes the form of a viscoelastic gel or liquid. Increasing the concentration of the medium chain carboxylic acid, medium chain peroxycarboxylic acid, or mixture thereof can increase the degree to which the composition is a viscoelastic gel or liquid. Increasing the concentration of the surfactant solubilizer can increase the degree to which the composition is a viscoelastic gel or liquid. In an embodiment, the gel can be sufficiently viscoelastic to hold its molded shape. Alkyl benzene sulfonate surfactant (e.g., LAS) can be employed to form a viscoelastic gel or liquid that can hold its molded shape. In an embodiment, the alkyl benzene sulfonate surfactant containing viscoelastic gel can hold its shape even at 60° C.

Although not limiting to the present invention, the present compositions may include medium chain peroxycarboxylic acid sequestered in the surfactant of the microemulsion. This can stabilize the peroxycarboxylic acid by keeping it away from impurities or reducing agents in the bulk water. This can increase the production of peroxycarboxylic acid by pulling it out of solution. Although not limiting to the present invention, it is believed that one explanation for the viscoelastic properties of gels of the present compositions is that they are due to repulsive forces between the dispersions/droplets that are stabilized by the microemulsion-forming surfactant. Surfactants that are charged may increase the electrostatic repulsion. Suitable charged surfactants include anionic surfactants.

In an embodiment, the present composition includes anionic surfactant and another surfactant or surfactants. For example, the present compositions can include anionic surfactant and nonionic surfactant or semi-polar nonionic surfactant. For example, the present compositions can include anionic surfactant and alkyl amine oxide or alkyl dimethyl amine.

In an embodiment, the present composition includes medium chain peroxycarboxylic acid; medium chain carboxylic acid; carrier; and one or more (e.g., at least one) surfactants, e.g., microemulsion forming surfactants. For example, the present composition can include about 0.5 to about 5 wt-% medium chain peroxycarboxylic acid; about 1 to about 10 wt-% medium chain carboxylic acid; about 5 to about 97 wt-% carrier; and about 1 to about 20 wt-% surfactant, e.g., microemulsion forming surfactant. For example, the present composition can include about 0.5 to about 5 wt-% medium chain peroxycarboxylic acid; about 1 to about 10 wt-% medium chain carboxylic acid; about 15 to about 80 wt-% carrier; and about 1 to about 20 wt-% surfactant, e.g., microemulsion forming surfactant. For example, the present composition can include about 0.5 to about 5 wt-% medium chain peroxycarboxylic acid; about 1 to about 10 wt-% medium chain carboxylic acid; about 30 to about 70 wt-% carrier; and about 2 to about 20 wt-% surfactant, e.g., microemulsion forming surfactant. In an embodiment, the present composition includes surfactant or microemulsion former solubilizer and greater than or equal to 35 wt-% carrier (e.g., water). The composition can include any of these ranges or amounts not modified by about.

In an embodiment, the present composition includes C8 peroxycarboxylic acid; C8 carboxylic acid; water; and one or more (e.g., at least one) surfactants, e.g., microemulsion forming surfactants. For example, the present composition can include about 0.5 to about 5 wt-% C8 peroxycarboxylic acid; about 1 to about 10 wt-% C8 carboxylic acid; about 5 to about 97 wt-% water; and about 1 to about 20 wt-% surfactant, e.g., microemulsion forming surfactant. For example, the present composition can include about 0.5 to about 5 wt-% C8 peroxycarboxylic acid; about 1 to about 10 wt-% C8 carboxylic acid; about 15 to about 80 wt-% water; and about 1 to about 20 wt-% surfactant, e.g., microemulsion forming surfactant. For example, the present composition can include about 0.5 to about 5 wt-% C8 peroxycarboxylic acid; about 1 to about 10 wt-% C8 carboxylic acid; about 30 to about 70 wt-% water; and about 2 to about 20 wt-% surfactant, e.g., microemulsion forming surfactant. The composition can include any of these ranges or amounts not modified by about.

In certain embodiments, the present composition includes about 0.001 to about 60 wt-% surfactant, e.g., microemulsion forming surfactant, as solubilizer, about 1 to about 25 wt-% surfactant, e.g., microemulsion forming surfactant, as solubilizer, about 1 to about 20 wt-% surfactant, e.g., microemulsion forming surfactant, as solubilizer, about 2 to about 20 wt-% surfactant, e.g., microemulsion forming surfactant, as solubilizer, about 3 to about 15 wt-% surfactant, e.g., microemulsion forming surfactant, as solubilizer, about 4 to about 20 wt-% surfactant, e.g., microemulsion forming surfactant, as solubilizer, about 4 to about 10 wt-% surfactant, e.g., microemulsion forming surfactant, as solubilizer, about 5 to about 20 wt-% surfactant, e.g., microemulsion forming surfactant, as solubilizer, or about 10 to about 20 wt-% surfactant, e.g., microemulsion forming surfactant, as solubilizer. The composition can include any of these ranges or amounts not modified by about.

Anionic Surfactants

The present composition can include an anionic surfactant as solubilizer. Suitable anionic surfactants include organic sulfonate surfactant, organic sulfate surfactant, phosphate ester surfactant, carboxylate surfactant, mixtures thereof, or the like. In an embodiment, the anionic surfactant includes alkyl sulfonate, alkylaryl sulfonate, alkylated diphenyl oxide disulfonate, alkylated naphthalene sulfonate, alcohol alkoxylate carboxylate, sarcosinate, taurate, acyl amino acid, alkanoic ester, phosphate ester, sulfuric acid ester, salt or acid form thereof, or mixture thereof. The particular salts will be suitably selected depending upon the particular formulation and the needs therein.

Suitable anionic surfactants include sulfonic acids (and salts), such as isethionates (e.g. acyl isethionates), alkylaryl sulfonic acids and salts thereof, alkyl sulfonates, secondary alkane sulfonates, and the like.

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives or their free acids. Suitable sulfonates include olefin sulfonates, such as long chain alkene sulfonates, long chain hydroxyalkane sulfonates or mixtures of alkenesulfonates and hydroxyalkanesulfonates. Suitable sulfonates include secondary alkane sulfonates.

In certain embodiments, the present compositions including an anionic surfactant, such as a normal C8 sulfonate, can be non-foam or low foam compositions. Such compositions can be advantageous for applications such as clean in place, machine warewashing, destaining, and sanitizing, laundry washing, destaining, and sanitizing, etc.

For applications in which foaming is desirable, a foaming agent can be added as part of the present composition or separately. In a two-step offering, a foaming agent can be combined with a dilution of the non-foam or low foam composition to form a foaming use solution. In a one-step offering, the foaming agent can be incorporated into the concentrated composition. One suitable foaming agent is LAS acid. LAS acid can form a microemulsion in the present compositions. LAS acid can form a viscoelastic gel or liquid in the present compositions. Additional suitable foaming agents include secondary alkane sulfonate, alkylated diphenyl oxide disulfonate (e.g., C12 alkyl diphenyl oxide disulfonate), alkyl ether sulfate (e.g., with n=1-3) (e.g., sodium laureth sulfate (with n=1, 2, or 3)), sodium lauryl sulfate, or the like.

In an embodiment, such foaming agents provide a foaming composition with one or more desirable foaming characteristics. Desirable foaming characteristics include, for example, foam being visible for about 5 min after forming the foam; foam with continuous and good drainage (e.g., when applied to a vertical surface); foam that dries to a clear appearance, e.g., that leaves no visible residue on a stainless steel surface; and/or foam that can be applied with a moderate or low odor compared to a conventional foam containing peroxyacetic acid.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of Formula 3:

$$R—O—(CH_2CH_2O)_n(CH_2)_m—CO_2X \qquad (3)$$

in which R is a $C_8$ to $C_{22}$ alkyl group or

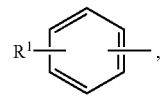

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In an embodiment, in Formula 3, n is an integer of 4 to 10 and m is 1. In an embodiment, in Formula 3, R is a $C_8$-$C_{16}$ alkyl group. In an embodiment, in Formula 3, R is a $C_{12}$-$C_{14}$ alkyl group, n is 4, and m is 1.

In an embodiment, in Formula 3, R is

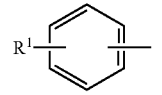

and $R^1$ is a $C_6$-$C_{12}$ alkyl group. In an embodiment, in Formula 3, $R^1$ is a $C_9$ alkyl group, n is 10 and m is 1.

Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazoline derivatives having application in the present invention generally have the general formula:

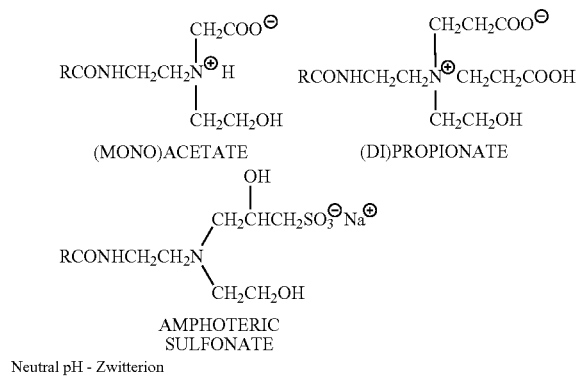

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-$C(O)$—NH—$CH_2$—$CH_2$—$N^+(CH_2$—$CH_2$—$CO_2Na)_2$—$CH_2$—$CH_2$—OH or $C_{12}$-alkyl-$C(O)$—$N(H)$—$CH_2$—$CH_2$—$N^+(CH_2$—$CO_2Na)_2$—$CH_2$—$CH_2$—OH.

Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

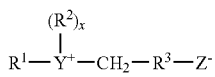

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

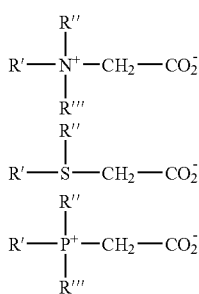

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12\text{-}14}$ acylamidopropylbetaine; $C_{8\text{-}14}$ acylamidohexyldiethyl betaine; 4-$C_{14\text{-}16}$ acylmethylamidodiethylammonio-1-carboxybutane; $C_{16}$-18 acylamidodimethylbetaine; $C_{12}$-16 acylamidopentanediethylbetaine; and $C_{12}$-16 acylmethylamidodimethylbetaine.

Sultaines useful in the present invention include those compounds having the formula $(R(R^1)_2N^+R^2SO_3^-)$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the composition of the present invention includes a betaine. For example, the composition can include cocoamidopropyl betaine.

Embodiments of Compositions

Some examples of representative constituent concentrations for embodiments of the present compositions can be found in Tables A-C, in which the values are given in wt-% of the ingredients in reference to the total composition weight. In certain embodiments, the proportions and amounts in Tables A-C can be modified by "about".

TABLE A

| Ingredient | wt-% | wt-% | wt-% | wt-% |
| --- | --- | --- | --- | --- |
| medium chain peroxycarboxylic acid | 0.3-7 | 0.5-5 | 0.5-4 | 1-3 |
| medium chain carboxylic acid | 1-10 | 2-8 | 2-6 | 2.5-5 |
| solubilizer | 1-80 | 2-70 | 3-65 | 5-60 |
| carrier | 0-98 | 5-90 | 10-80 | 20-70 |

TABLE B

| Ingredient | wt-% | wt-% | wt-% | wt-% |
| --- | --- | --- | --- | --- |
| medium chain peroxycarboxylic acid | 0.3-7 | 0.5-5 | 0.5-4 | 1-3 |
| medium chain carboxylic acid | 1-10 | 2-8 | 3-6 | 3-5 |
| solubilizer | 1-80 | 5-70 | 10-65 | 20-60 |
| carrier | 0-98 | 0.2-60 | 5-20 | 20-40 |

TABLE C

| Ingredient | wt-% | wt-% | wt-% | wt-% |
| --- | --- | --- | --- | --- |
| medium chain peroxycarboxylic acid | 0.3-7 | 0.5-5 | 0.5-4 | 1-2 |
| medium chain carboxylic acid | 1-10 | 1-8 | 1.5-6 | 2-4 |
| solubilizer | 1-25 | 2-20 | 3-15 | 4-10 |
| carrier | 5-97 | 10-90 | 15-70 | 30-75 |

Some examples of representative constituent concentrations for additional embodiments of the present compositions can be found in Tables D-F, in which the values are given in wt-% of the ingredients in reference to the total composition weight. In certain embodiments, the proportions and amounts in Tables D-F can be modified by "about".

TABLE D

| Ingredient | wt-% | wt-% | wt-% | wt-% | wt-% | wt-% |
|---|---|---|---|---|---|---|
| medium chain peroxycarboxylic acid | 0.3-7 | 0.3-7 | 0.3-7 | 0.5-5 | 0.5-4 | 1-3 |
| medium chain carboxylic acid | 1-10 | 1-10 | 1-10 | 2-8 | 2-6 | 2.5-5 |
| solubilizer | 1-80 | 1-80 | 1-80 | 2-70 | 3-65 | 5-60 |
| carrier | 0-98 | 0-98 | 0-98 | 5-90 | 10-80 | 20-70 |
| oxidizing agent | 2-70 | 2-50 | 2-40 | 2-25 | 4-20 | 6-10 |
| acidulant | 1-50 | 1-50 | 1-50 | 2-40 | 3-40 | 5-40 |
| stabilizing agent | 1-50 | 1-50 | 1-50 | 1-10 | 1-5 | 1-3 |
| optional defoamer | 0-50 | 0.1-20 | 0.1-10 | 0.3-3 | 0.5-2 | 0.5-1.5 |

TABLE E

| Ingredient | wt-% | wt-% | wt-% | wt-% | wt-% | wt-% |
|---|---|---|---|---|---|---|
| medium chain peroxycarboxylic acid | 0.3-7 | 0.3-7 | 0.3-7 | 0.5-5 | 0.5-4 | 1-3 |
| medium chain carboxylic acid | 1-10 | 1-10 | 1-10 | 2-8 | 3-6 | 3-5 |
| solubilizer | 1-80 | 1-80 | 1-80 | 5-70 | 10-65 | 20-60 |
| carrier | 0-98 | 0-98 | 0-98 | 0.2-60 | 5-20 | 20-40 |
| oxidizing agent | 2-70 | 2-50 | 2-40 | 2-25 | 4-20 | 6-10 |
| acidulant | 1-50 | 1-50 | 1-50 | 2-40 | 3-40 | 5-40 |
| stabilizing agent | 1-50 | 1-50 | 1-50 | 1-10 | 1-5 | 1-3 |
| optional defoamer | 0-50 | 0.1-20 | 0.1-10 | 0.3-3 | 0.5-2 | 0.5-1.5 |

TABLE F

| Ingredient | wt-% | wt-% | wt-% | wt-% | wt-% | wt-% |
|---|---|---|---|---|---|---|
| medium chain peroxycarboxylic acid | 0.3-7 | 0.3-7 | 0.3-7 | 0.5-5 | 0.5-4 | 1-2 |
| medium chain carboxylic acid | 1-10 | 1-10 | 1-10 | 1-8 | 1.5-6 | 2-4 |
| solubilizer | 1-25 | 1-25 | 1-25 | 2-20 | 3-15 | 4-10 |
| carrier | 5-97 | 5-97 | 5-97 | 10-90 | 15-70 | 30-75 |
| oxidizing agent | 2-70 | 2-50 | 2-30 | 2-25 | 4-20 | 6-10 |
| acidulant | 1-50 | 1-50 | 1-50 | 2-40 | 3-35 | 5-30 |
| stabilizing agent | 1-50 | 1-50 | 1-50 | 1-15 | 1-5 | 1-3 |
| optional defoamer | 0-50 | 0.1-20 | 0.1-10 | 0.3-3 | 0.5-2 | 0.5-1.5 |

In an embodiment, the compositions of the present invention include only ingredients that can be employed in food products or in food wash, handling, or processing, for example, according to government (e.g. FDA or USDA) rules and regulations, 21 CFR §170-178. In an embodiment, the compositions of the present invention can include only ingredients at the concentrations approved for incidental food contact by the USEPA, 40 CFR §180.940.

The present compositions can take the form of a liquid, solid, gel, paste, unit dose, gel pack, or the like. The present compositions can be supplied in any of a variety of containers or media, such as in a 2 compartment dispenser or as a pre-moistened wipe, towelette, or sponge.

Carrier

The composition of the invention can also include a carrier. The carrier provides a medium which dissolves, suspends, or carries the other components of the composition. For example, the carrier can provide a medium for solubilization, suspension, or production of peroxycarboxylic acid and for forming an equilibrium mixture. The carrier can also function to deliver and wet the antimicrobial composition of the invention on an object. To this end, the carrier can contain any component or components that can facilitate these functions.

In certain embodiments, the carrier includes primarily water which can promote solubility and work as a medium for reaction and equilibrium. The carrier can include or be primarily an organic solvent, such as simple alkyl alcohols, e.g., ethanol, isopropanol, n-propanol, and the like. Polyols are also useful carriers, including glycerol, sorbitol, and the like.

Suitable carriers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

In certain embodiments, the carrier makes up a large portion of the composition of the invention and may be the balance of the composition apart from the active antimicrobial components, solubilizer, oxidizing agent, adjuvants, and the like. Here again, the carrier concentration and type will depend upon the nature of the composition as a whole, the environmental storage, and method of application including concentration of the medium chain peroxycarboxylic acid, among other factors. Notably the carrier should be chosen and used at a concentration which does not inhibit the antimicrobial efficacy of the medium chain peroxycarboxylic acid in the composition of the invention.

In certain embodiments, the present composition includes about 0 to about 98 wt-% carrier, about 0.001 to about 99.99 wt-% carrier, about 0.2 to about 60 wt-% carrier, about 1 to about 98 wt-% carrier, about 5 to about 99.99 wt-% carrier, about 5 to about 97 wt-% carrier, about 5 to about 90 wt-% carrier, about 5 to about 70 wt-% carrier, about 5 to about 20 wt-% carrier, about 10 to about 90 wt-% carrier, about 10 to about 80 wt-% carrier, about 10 to about 50 wt-% carrier, about 10 to about 20 wt-% carrier, about 15 to about 70 wt-% carrier, about 15 to about 80 wt-% carrier, about 20 to about 70 wt-% carrier, about 20 to about 50 wt-% carrier, about 20 to about 40 wt-% carrier, about 20 to about 30 wt-% carrier, about 30 to about 75 wt-% carrier, about 30 to about 70 wt-% carrier, about 40 to about 99.99 wt-% carrier, about 40 to about 90 wt-% carrier, or about 60 to about 70 wt-% carrier. The composition can include any of these ranges or amounts not modified by about.

Oxidizing Agent

The present compositions and methods can include any of a variety of oxidizing agents. The oxidizing agent can be used for maintaining or generating peroxycarboxylic acids.

Examples of inorganic oxidizing agents include the following types of compounds or sources of these compounds, or alkali metal salts including these types of compounds, or forming an adduct therewith:

hydrogen peroxide;

group 1 (IA) oxidizing agents, for example lithium peroxide, sodium peroxide, and the like;

group 2 (IIA) oxidizing agents, for example magnesium peroxide, calcium peroxide, strontium peroxide, barium peroxide, and the like;

group 12 (IIB) oxidizing agents, for example zinc peroxide, and the like;

group 13 (IIIA) oxidizing agents, for example boron compounds, such as perborates, for example sodium perborate hexahydrate of the formula $Na_2[B_2(O_2)_2(OH)_4].6H_2O$ (also called sodium perborate tetrahydrate and formerly written as $NaBO_3.4H_2O$); sodium peroxyborate tetrahydrate of the formula $Na_2Br_2(O_2)_2[(OH)_4].4H_2O$ (also called sodium perborate trihydrate, and formerly written as $NaBO_3.3H_2O$); sodium peroxyborate of the formula $Na_2[B_2(O_2)_2(OH)_4]$ (also called sodium perborate monohydrate and formerly written as $NaBO_3.H_2O$); and the like; in an embodiment, perborate;

group 14 (IVA) oxidizing agents, for example persilicates and peroxycarbonates, which are also called percarbonates, such as persilicates or peroxycarbonates of alkali metals; and the like; in an embodiment, percarbonate; in an embodiment, persilicate;

group 15 (VA) oxidizing agents, for example peroxynitrous acid and its salts; peroxyphosphoric acids and their salts, for example, perphosphates; and the like; in an embodiment, perphosphate;

group 16 (VIA) oxidizing agents, for example peroxysulfuric acids and their salts, such as peroxymonosulfuric and peroxydisulfuric acids, and their salts, such as persulfates, for example, sodium persulfate; and the like; in an embodiment, persulfate;

group VIIa oxidizing agents such as sodium periodate, potassium perchlorate and the like.

Other active inorganic oxygen compounds can include transition metal peroxides; and other such peroxygen compounds, and mixtures thereof.

In an embodiment, the compositions and methods of the present invention employ one or more (e.g., at least one) of the inorganic oxidizing agents listed above. Suitable inorganic oxidizing agents include ozone, hydrogen peroxide, hydrogen peroxide adduct, group IIIA oxidizing agent, group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

Hydrogen peroxide presents one suitable example of an inorganic oxidizing agent. Hydrogen peroxide can be provided as a mixture of hydrogen peroxide and water, e.g., as liquid hydrogen peroxide in an aqueous solution. Hydrogen peroxide is commercially available at concentrations of 35%, 50%, 70%, and 90% in water. For safety, the 35% is commonly used. The present compositions can include, for example, about 2 to about 30 wt-% or about 5 to about 20 wt-% hydrogen peroxide.

In an embodiment, the inorganic oxidizing agent includes hydrogen peroxide adduct. For example, the inorganic oxidizing agent can include hydrogen peroxide, hydrogen peroxide adduct, or mixtures thereof. Any of a variety of hydrogen peroxide adducts are suitable for use in the present compositions and methods. For example, suitable hydrogen peroxide adducts include percarbonate salt, urea peroxide, peracetyl borate, an adduct of $H_2O_2$ and polyvinyl pyrrolidone, sodium percarbonate, potassium percarbonate, mixtures thereof, or the like. Suitable hydrogen peroxide adducts include percarbonate salt, urea peroxide, peracetyl borate, an adduct of $H_2O_2$ and polyvinyl pyrrolidone, or mixtures thereof. Suitable hydrogen peroxide adducts include sodium percarbonate, potassium percarbonate, or mixtures thereof, for example sodium percarbonate.

In an embodiment, the present compositions and methods can include hydrogen peroxide as oxidizing agent. Hydrogen peroxide in combination with the percarboxylic acid can provide certain antimicrobial action against microorganisms. Additionally, hydrogen peroxide can provide an effervescent action which can irrigate any surface to which it is applied. Hydrogen peroxide can work with a mechanical flushing action once applied which further cleans the surface of an object. An additional advantage of hydrogen peroxide is the food compatibility of this composition upon use and decomposition.

In certain embodiments, the present composition includes about 0.001 to about 30 wt-% oxidizing agent, about 0.001 to about 10 wt-% oxidizing agent, 0.002 to about 10 wt-% oxidizing agent, about 2 to about 70 wt-% oxidizing agent, about 2 to about 60 wt-% oxidizing agent, about 2 to about 50 wt-% oxidizing agent, about 2 to about 40 wt-% oxidizing agent, about 2 to about 30 wt-% oxidizing agent, about 2 to about 25 wt-% oxidizing agent, about 2 to about 20 wt-% oxidizing agent, about 4 to about 20 wt-% oxidizing agent, about 5 to about 10 wt-% oxidizing agent, or about 6 to about 10 wt-% oxidizing agent. The composition can include any of these ranges or amounts not modified by about.

Acidulant

In an embodiment, the present composition can include an acidulant. The acidulant can act as a catalyst for conversion of carboxylic acid to peroxycarboxylic acid. The acidulant can be effective to form a concentrate composition with pH of about 1 or less. The acidulant can be effective to form a use composition with pH of about 5, about 5 or less, about 4, about 4 or less, about 3, about 3 or less, about 2, about 2 or less, or the like. In an embodiment, the acidulant includes an inorganic acid. Suitable inorganic acids include sulfuric acid, phosphoric acid, nitric acid, hydrochloric acid, methane sulfonic acid, ethane sulfonic acid, propane sulfonic acid, butane sulfonic acid, xylene sulfonic acid, benzene sulfonic acid, mixtures thereof, or the like.

In an embodiment, the acidulant includes a carboxylic acid with $pK_a$ less than 4. Suitable carboxylic acids with $pK_a$ less than 4 include hydroxyacetic acid, hydroxypropionic acid, other hydroxycarboxylic acids, mixtures thereof, or the like. Such an acidulant is present at a concentration where it does not act as a solubilizer.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

Stabilizing Agent

One or more stabilizing agents can be added to the composition of the invention, for example, to stabilize the peracid and hydrogen peroxide and prevent the premature oxidation of this constituent within the composition of the invention.

Suitable stabilizing agents include chelating agents or sequestrants. Suitable sequestrants include organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, or aminocarboxylic acids.

The sequestrant can be or include phosphonic acid or phosphonate salt. Suitable phosphonic acids and phosphonate salts include 1-hydroxy ethylidene-1,1-diphosphonic acid ($CH_3C(PO_3H_2)_2OH$) (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetraethanolamine salts; or mixtures thereof.

Suitable organic phosphonates include HEDP.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), ($N[CH_2PO_3H_2]_3$), available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N, N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0.5 to about 50 wt-% sequestrant, about 1 to about 50 wt-% sequestrant, about 1 to about 30 wt-% sequestrant, about 1 to about 15 wt-% sequestrant, about 1 to about 5 wt-% sequestrant, about 1 to about 4 wt-% sequestrant, about 2 to about 10 wt-% sequestrant, about 2 to about 5 wt-% sequestrant, or about 5 to about 15 wt-% sequestrant. The composition can include any of these ranges or amounts not modified by about.

In certain embodiments, the present composition includes about 0.001 to about 50 wt-% stabilizing agent, about 0.001 to about 5 wt-% stabilizing agent, about 0.5 to about 50 wt-% stabilizing agent, about 1 to about 50 wt-% stabilizing agent, about 1 to about 30 wt-% stabilizing agent, about 1 to about 10 wt-% stabilizing agent, about 1 to about 5 wt-% stabilizing agent, about 1 to about 3 wt-% stabilizing agent, about 2 to about 10 wt-% stabilizing agent, about 2 to about 5 wt-% stabilizing agent, or about 5 to about 15 wt-% stabilizing agent. The composition can include any of these ranges or amounts not modified by about.

Adjuvants

The antimicrobial composition of the invention can also include any number of adjuvants. Specifically, the composition of the invention can include antimicrobial solvent, antimicrobial agent, wetting agent, defoaming agent, thickener, a surfactant, foaming agent, solidification agent, aesthetic enhancing agent (i.e., colorant (e.g., pigment), odorant, or perfume), catalyst, among any number of constituents which can be added to the composition. A catalyst such as a metal ion (e.g., Mo or Fe ion) or halogen (e.g., iodine) can increase the rate at which hydrogen peroxide degrades. An enzyme such as catalase can be employed as catalyst.

Such adjuvants can be preformulated with the antimicrobial composition of the invention or added to the system simultaneously, or even after, the addition of the antimicrobial composition. The composition of the invention can also contain any number of other constituents as necessitated by the application, which are known and which can facilitate the activity of the present invention.

Antimicrobial Solvent

Any of a variety of solvents can be useful as antimicrobial solvents in the present compositions. Antimicrobial solvent can be added to use compositions before use. Suitable antimicrobial solvents include acetamidophenol; acetanilide; acetophenone; 2-acetyl-1-methylpyrrole; benzyl acetate; benzyl alcohol; benzyl benzoate; benzyloxyethanol; essential oils (e.g., benzaldehyde, pinenes, terpineols, terpinenes, carvone, cinnamealdehyde, borneol and its esters, citrals, ionenes, jasmine oil, limonene, dipentene, linalool and its esters); diester dicarboxylates (e.g., dibasic esters) such as dimethyl adipate, dimethyl succinate, dimethyl glutarate (including products available under the trade designations DBE, DBE-3, DBE-4, DBE-5, DBE-6, DBE-9, DBE-IB, and DBE-ME from DuPont Nylon), dimethyl malonate, diethyl adipate, diethyl succinate, diethyl glutarate, dibutyl succinate, and dibutyl glutarate; dimethyl sebacate, dimethyl pimelate, dimethyl suberate; dialkyl carbonates such as dimethyl carbonate, diethyl carbonate, dipropyl carbonate, diisopropyl carbonate, and dibutyl carbonate; organo-nitriles such as acetonitrile and benzonitrile; and phthalate esters such as dibutyl phthalate, diethylhexyl phthalate, and diethyl phthalate. Mixtures of antimicrobial solvents can be used if desired.

The antimicrobial solvent can be selected based upon the characteristics of the surface and microbes to which the antimicrobial composition will be applied and upon the nature of any coating, soil or other material that will be contacted by the antimicrobial composition and optionally removed from the surface. Polar solvents, and solvents that are capable of hydrogen bonding typically will perform well on a variety of surfaces and microbes and thus, for such applications, can be selected. In certain applications, the antimicrobial solvent can be selected for a high flashpoint (e.g., greater than about 30° C., greater than about 50° C., or greater than about 100° C.), low odor, and low human and animal toxicity.

In an embodiment, the antimicrobial solvent is compatible as an indirect or direct food additive or substance; especially those described in the Code of Federal Regulations (CFR), Title 21—Food and Drugs, parts 170 to 186. The compositions of the invention should contain sufficient antimicrobial solvent to provide the desired rate and type of microbial reduction.

The present composition can include an effective amount of antimicrobial solvent, such as about 0.01 wt-% to about 60 wt-% antimicrobial solvent, about 0.05 wt-% to about 15 wt-% antimicrobial solvent, or about 0.08 wt-% to about 5 wt-% antimicrobial solvent.

Additional Antimicrobial Agent

The antimicrobial compositions of the invention can contain an additional antimicrobial agent. Additional antimicrobial agent can be added to use compositions before use. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection.

The present composition can include an effective amount of additional antimicrobial agent, such as about 0.001 wt-% to about 60 wt-% antimicrobial agent, about 0.01 wt-% to about 15 wt-% antimicrobial agent, or about 0.08 wt-% to about 2.5 wt-% antimicrobial agent.

Wetting or Defoaming Agents

Also useful in the composition of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Suitable defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; capped nonionic surfactants; fatty acid soaps such as alkali metal or alkaline earth metal soaps; and phosphates and phosphate esters such as alkyl and alkaline diphosphates, and tributyl phosphates among others; and mixtures thereof.

In an embodiment, the present compositions can include antifoaming agents or defoamers (antifoaming and defoaming are used interchangeably herein) which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, from about 0.01 wt-% to 2 wt-%, or from about 0.01 wt-% to about 1 wt-%.

Thickening or Gelling Agents

The present compositions can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, from about 0.1 wt-% to about 1.0 wt-%, or from about 0.1 wt-% to about 0.5 wt-%.

Solidification Agent

The present compositions can include a solidification agent, which can participate in maintaining the compositions in a solid form. Suitable solidification agents include a solid polyethylene glycol (PEG), a solid EO/PO block copolymer, and the like; an amide, such as stearic monoethanolamide, lauric diethanolamide, an alkylamide, or the like; starches that have been made water-soluble through an acid or alkaline treatment process; celluloses that have been made water-soluble; an inorganic agent, or the like; poly(maleic anhydride/methyl vinyl ether); polymethacrylic acid; other generally functional or inert materials with high melting points; and the like.

In certain embodiments, the solidification agent includes solid PEG, for example PEG 1500 up to PEG 20,000. In certain embodiments, the PEG includes PEG 1450, PEG 3350, PEG 4500, PEG 8000, PEG 20,000, and the like. Additional suitable solidification agents include EO/PO block copolymers such as those sold under the tradenames Pluronic 108, Pluronic F68; amides such as lauric diethanolamide or cocodiethylene amide; and the like. In certain embodiments, the solidification agent includes a combination of solidification agents, such as combination of PEG and an EO/PO block copolymer (such as a Pluronic) and combination of PEG and an amide (such as lauric diethanolamide amide or stearic monoethanol amide).

Fragrance

In an embodiment, the present composition includes a fragrance. The fragrance can be selected to avoid undesirable effects on the stability or efficacy of the composition. Suitable fragrances include amyl acetate, iso-bornyl acetate, and alkyl salicylates, such as methyl salicylate. In an embodiment, the fragrance can include an alkylsalicylate.

Additional Embodiments of the Medium Chain Peroxycarboxylic Acid Compositions The present invention relates to compositions including medium chain peroxycarboxylic acid, methods for making these compositions, and methods for reducing the population of a microorganism. In certain embodiments, the compositions can include advantageously high levels of the medium chain peroxycarboxylic acid, can be readily made, and/or can exhibit reduced odor.

In an embodiment, the present compositions can include medium chain peroxycarboxylic acid, medium chain carboxylic acid, carrier, and solubilizer. In certain embodiments, the present compositions include about 2 or more parts of medium chain peroxycarboxylic acid for each 7 parts of medium chain carboxylic acid; about 2 or more parts of medium chain peroxycarboxylic acid for each 5 parts of medium chain carboxylic acid; about 2 or more parts of medium chain peroxycarboxylic acid for each 4 parts of medium chain carboxylic acid; or about 2 parts of medium chain peroxycarboxylic acid for each 3 parts of medium chain carboxylic acid.

In an embodiment, the solubilizer includes solvent, surfactant, or mixture thereof. In an embodiment, the surfactant solubilizer includes a microemulsion forming surfactant, e.g., an anionic surfactant. In an embodiment, the composition includes a microemulsion. In an embodiment, the solubilizer includes polyalkylene oxide, capped polyalkylene oxide, nonionic surfactant, anionic surfactant, or mixture thereof. In an embodiment, the solvent solubilizer includes polyalkylene oxide, capped polyalkylene oxide, nonionic surfactant, or mixture thereof.

In an embodiment, the present compositions include no, only insignificant, or relatively small amounts of short chain peroxycarboxylic acid, short chain carboxylic acid, or mixture thereof. For example, in an embodiment, the composition can be substantially free of added short chain carboxylic acid, short chain peroxycarboxylic acid, or mixture thereof. For example, in an embodiment, the composition can include short chain carboxylic acid, short chain peroxycarboxylic acid, or mixture thereof at a level insufficient to solubilize medium chain peroxycarboxylic acid. For example, in an embodiment, the composition can include short chain carboxylic acid, short chain peroxycarboxylic acid, or mixture thereof at a level insufficient to cause objectionable odor. For example, in an embodiment, the composition can include about 1 or more parts of medium chain peroxycarboxylic acid for each 8 parts of short chain carboxylic acid, short chain peroxycarboxylic acid, or mixture thereof.

In an embodiment, the composition also includes oxidizing agent, inorganic acid, stabilizing agent, another adjuvant or additive, or mixture thereof.

In an embodiment, the present invention includes a method of making a medium chain peroxycarboxylic acid composition. The method can include reacting medium chain carboxylic acid and oxidizing agent in the presence of carrier, solubilizer, acidulant, stabilizing agent, or mixture thereof. The method can form advantageously high levels of medium chain peroxycarboxylic acids in advantageously short times. For example, in an embodiment, the present method includes converting 20% or more of the medium chain carboxylic acid to medium chain peroxycarboxylic acid in about 24 or fewer hours. For example, in an embodiment, the present method includes converting about 25% or more of the medium chain carboxylic acid to medium chain peroxycarboxylic acid in about 24 or fewer hours. For example, in an embodiment, the present method includes converting about 30% or more of the medium chain carboxylic acid to medium chain peroxycarboxylic acid in about 24 or fewer hours. For example, in an embodiment, the present method includes converting about 35% or more of the medium chain carboxylic acid to medium chain peroxycarboxylic acid in about 24 or fewer hours. For example, in an embodiment, the present method includes converting about 40% of the medium chain carboxylic acid to medium chain peroxycarboxylic acid in about 24 or fewer hours.

In an embodiment, the present invention includes a method of using a medium chain peroxycarboxylic acid composition. The method can include contacting an object with the present composition (e.g., a use composition) and can result in reducing the population of one or more microorganisms on the object.

Use Compositions

The present compositions include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the medium chain peroxycarboxylic acid compound. Generally, a dilution of about 1 fluid ounce to about 20 gallons of water to about 5 fluid ounces to about 1 gallon of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water.

For example, a use composition can include about 0.01 to about 4 wt-% of a concentrate composition and about 96 to about 99.99 wt-% diluent; about 0.5 to about 4 wt-% of a concentrate composition and about 96 to about 99.5 wt-% diluent; about 0.5, about 1, about 1.5, about 2, about 2.5, about 3, about 3.5, or about 4 wt-% of a concentrate composition; about 0.01 to about 0.1 wt-% of a concentrate composition; or about 0.01, about 0.02, about 0.03, about 0.04, about 0.05, about 0.06, about 0.07, about 0.08, about 0.09, or about 0.1 wt-% of a concentrate composition. Amounts of an ingredient in a use composition can be calculated from the amounts listed above for concentrate compositions and these dilution factors.

The present methods can employ medium chain peroxycarboxylic acid at a concentration effective for reducing the population of one or more microorganisms. Such effective concentrations include about 2 to about 500 ppm medium chain peroxycarboxylic acid, about 2 to about 300 ppm medium chain peroxycarboxylic acid, about 5 to about 100 ppm medium chain peroxycarboxylic acid, about 5 to about 60 ppm medium chain peroxycarboxylic acid, about 5 to about 45 ppm medium chain peroxycarboxylic acid, about 5 to about 35 ppm medium chain peroxycarboxylic acid, about 5 to about 25 ppm medium chain peroxycarboxylic acid, about 8 to about 50 ppm medium chain peroxycarboxylic acid, about 10 to about 500 ppm medium chain peroxycarboxylic acid, about 10 to about 50 ppm medium chain peroxycarboxylic acid, about 40 to about 140 ppm medium chain peroxycarboxylic acid, about 100 to about 250 ppm medium chain peroxycarboxylic acid, or about 200 to about 300 ppm medium chain peroxycarboxylic acid. In an embodiment, the use composition can include about 2 to about 500 ppm medium chain peroxycarboxylic acid, about 5 to about 2000 ppm medium chain carboxylic acid, about 95 to about 99.99 wt-% carrier and/or diluent (e.g., water); and about 2 to about 23,000 ppm polyalkylene oxide, capped polyalkylene oxide, alkoxylated surfactant, anionic surfactant, or mixture thereof.

The level of reactive species, such as peroxycarboxylic acids and/or hydrogen peroxide, in a use composition can be affected, typically diminished, by organic matter that is found in or added to the use composition. For example, when the use composition is a bath or spray used for washing an object, soil on the object can consume peroxy acid and peroxide. Thus, the present amounts of ingredients in the use compositions refer to the composition before or early in use, with the understanding that the amounts will diminish as organic matter is added to the use composition.

In an embodiment, the present use composition can be made more acidic by passing the concentrate through an acidifying column, or by adding additional acidulant to the use composition.

Other Fluid Compositions

The present and compositions can include a critical, near critical, or supercritical (densified) fluid and an antimicrobial agent or a gaseous composition of an antimicrobial agent. The densified fluid can be a near critical, critical, supercritical fluid, or another type of fluid with properties of a supercritical fluid. Fluids suitable for densification include carbon dioxide, nitrous oxide, ammonia, xenon, krypton, methane, ethane, ethylene, propane, certain fluoroalkanes (e.g., chlorotrifluoromethane and monofluoromethane), and the like, or mixtures thereof. Suitable fluids include carbon dioxide.

In an embodiment, the present compositions or methods include densified carbon dioxide, medium chain peroxycarboxylic acid, and medium chain carboxylic acid. Such a composition can be referred to as a densified fluid medium chain peroxycarboxylic acid composition. In another embodiment, the antimicrobial composition includes the fluid, an antimicrobial agent, and any of the optional or added ingredients, but is in the form of a gas.

Densified fluid antimicrobial compositions can be applied by any of several methods known to those of skill in the art. Such methods include venting at an object a vessel containing densified fluid and antimicrobial agent. The aqueous phase, which includes hydrogen peroxide, is advantageously retained in the device. The vented gas includes an effective amount of antimicrobial agent making the densified fluid peroxycarboxylic acid compositions effective antimicrobial agents.

Because of the high pressure nature of the densified fluid compositions of the invention, these compositions are typically applied by venting a vessel containing the composition through a pressure relief device that is designed to promote rapid efficient coverage of an object. Devices including such a pressure relief device include sprayers, foggers, foamers, foam pad applicators, brush applicators or any other device that can permit the expansion of the fluid materials from high pressure to ambient pressure while applying the material to an object. The densified fluid peroxycarboxylic acid composition can also be applied to an object by any of a variety of methods known for applying gaseous agents to an object.

Densified fluid antimicrobial compositions can be made by reacting an oxidizable substrate with an oxidizing agent in a medium comprising a densified fluid to form an antimicrobial composition. This reaction is typically carried out in a vessel suitable for containing a densified fluid. Reacting can include adding to the vessel the oxidizable substrate and the oxidizing agent, and adding fluid to the vessel to form the densified fluid. In an embodiment, the reaction is between a medium chain carboxylic acid and hydrogen peroxide to form the corresponding peroxycarboxylic acid. The hydrogen peroxide is commonly supplied in the form of an aqueous solution of hydrogen peroxide.

Supercritical, subcritical, near supercritical, and other dense fluids and solvents that can be employed with such fluids are disclosed in U.S. Pat. No. 5,306,350, issued Apr. 26, 1994 to Hoy et al., which is incorporated by reference herein for such disclosure. Supercritical and other dense forms of carbon dioxide, and cosolvents, co-surfactants, and other additives that can be employed with these forms of carbon dioxide are disclosed in U.S. Pat. No. 5,866,005, issued Feb.

2, 1999 to DeSimone et al., which is incorporated by reference herein for such disclosure.

Making Medium Chain Peroxycarboxylic Acid Compositions

The compositions of or used in the methods of the invention can be made by combining or reacting the medium chain carboxylic acid and the oxidizing agent, such as hydrogen peroxide. Combining or reacting medium chain carboxylic acid and oxidizing agent results in production of medium chain peroxycarboxylic acid. In an embodiment, combining includes mixing. The formulation combined for making the present compositions can also include the solubilizer, the acidulant, the carrier, stabilizing agent, mixtures thereof, or the like. In an embodiment, the formulation includes solubilizer. Alternatively, one or more (e.g., at least one) of the solubilizer, the acidulant, the carrier, or mixtures thereof, can be added after production of some or all of the peroxycarboxylic acid.

In an embodiment, the present invention includes a method of making a medium chain peroxycarboxylic acid. The method can include combining or reacting medium chain carboxylic acid, carrier (e.g., water), oxidizing agent (e.g., hydrogen peroxide), solubilizer, acidulant, and stabilizing agent. The method can include mixing the ingredients at concentrations of about 1 to about 10 wt-% medium chain carboxylic acid, about 0 to about 98 wt-% carrier, about 2 to about 70 wt-% oxidizing agent, about 1 to about 80 wt-% solubilizer, about 1 to about 50 wt-% acidulant, and about 0.5 to about 50 wt-% stabilizing agent. The method can include mixing the ingredients at concentrations about 1 to about 10 wt-% medium chain carboxylic acid, about 5 to about 97 wt-% carrier, about 2 to about 70 wt-% oxidizing agent, about 1 to about 20 wt-% solubilizer (e.g., microemulsion forming surfactant), about 1 to about 50 wt-% acidulant, and about 0.5 to about 50 wt-% stabilizing agent. The present compositions also include compositions in which these combinations of ingredients have come to equilibrium forming medium chain peroxycarboxylic acid.

In an embodiment, the present method produces advantageously high levels of medium chain peroxycarboxylic acid in advantageously short times. Advantageously short times include, for example, about 24 or fewer hours, about 6 or fewer hours, about 3 or fewer hours, or about 0.5 hr. In an embodiment, high levels of medium chain peroxycarboxylic acid can be achieved nearly instantaneously. High levels of medium chain peroxycarboxylic acid be achieved by converting 20% or more, 25% or more, 30% or more, 35% or more, or 40% of the medium chain carboxylic acid to medium chain peroxycarboxylic acid. Such conversions can be achieved at room temperature or in a reaction started at room temperature and warmed by an exotherm. Lower temperatures can require a longer time to reach the same amount of conversion. The amount of time is typically measured from the time that the carboxylic acid, oxidizing agent, solubilizer, and acidulant are combined or reacted.

For example, in an embodiment, the present method can convert 20% or more of the medium chain carboxylic acid to medium chain peroxycarboxylic acid in about 24 or fewer hours. For example, in an embodiment, the present method can convert about 25% or more of the medium chain carboxylic acid to medium chain peroxycarboxylic acid in about 24 or fewer hours. For example, in an embodiment, the present method can convert about 30% or more of the medium chain carboxylic acid to medium chain peroxycarboxylic acid in about 24 or fewer hours. For example, in an embodiment, the present method can convert about 35% or more of the medium chain carboxylic acid to medium chain peroxycarboxylic acid in about 24 or fewer hours. For example, in an embodiment, the present method can convert about 40% of the medium chain carboxylic acid to medium chain peroxycarboxylic acid in about 24 or fewer hours.

In an embodiment, making the present compositions includes forming a microemulsion. A microemulsion can be formed by mixing the desired ingredients including a microemulsion forming surfactant. The method can include combining or mixing the ingredients at concentration of about 1 to about 10 wt-% medium chain carboxylic acid, about 5 to about 97 wt-% carrier (e.g., water), about 2 to about 70 wt-% oxidizing agent, about 1 to about 20 wt-% microemulsion forming surfactant, and about 1 to about 50 wt-% stabilizer. The present compositions also include compositions in which these combinations of ingredients have come to equilibrium forming medium chain peroxycarboxylic acid. The components can be added in any of a variety of orders. In an embodiment, formation of the medium chain peroxy carboxylic acid can proceed rapidly after the addition of the microemulsion forming surfactant. Although not limiting to the present invention, it is believed that the formation of the microemulsion can significantly increase the effective surface area of the medium chain carboxylic acid (as micro-droplets) for reaction.

The present compositions can be made in a plant as a concentrate and shipped to an end user who need only dilute the concentrate to form a use composition. The present medium chain peroxycarboxylic acid compositions can also be made at the site of use. For example, the product can be shipped as a two or more part composition or as a kit. The user can then combine the two or more compositions or components of the kit to produce the present medium chain peroxycarboxylic acid compositions. Alternatively, a system of formulating equipment and containers of raw materials can be provided at the site of use, and programmed or operated to mix and disperse the present medium chain peroxycarboxylic acid compositions.

In an embodiment, the product can be supplied as a two or more part composition. In certain embodiments, one composition can include carboxylic acid and one or more (e.g., at least one) of solubilizer, acidulant, carrier, stabilizing agent, mixtures thereof, or the like. The second composition can include oxidizing agent and one or more (e.g., at least one) of solubilizer, acidulant, carrier, stabilizing agent, mixtures thereof, or the like. Alternatively, the solubilizer, acidulant, carrier, stabilizing agent mixtures thereof, or the like can be supplied as additional composition(s). In certain embodiments, one composition can include carboxylic acid and at least one of oxidizing agent, solubilizer, acidulant, carrier, stabilizing agent, mixtures thereof, and the like. The second composition can include at least one of fragrance, odor counteractant, emollient, other incompatible ingredient, oxidizing agent, solubilizer, acidulant, carrier, stabilizing agent, mixtures thereof, and the like.

In certain embodiments, one composition can include carboxylic acid and at least one of peroxycarboxylic acid, oxidizing agent, solubilizer, acidulant, carrier, stabilizing agent, mixtures thereof, and the like. The second composition can include at least buffer or alkalinity source, defoamer, foamer, glycols, polyol (e.g., polyhydroxy liquid, glycerine, or the like), solvent, mixtures thereof, and the like. In an embodiment, the defoamer can be added as a third composition.

In an embodiment, the pH of a concentrate composition can be less than about 1 or about 2. In an embodiment, the pH of a 1% or 1.5% solution of the mixture in water is about 1 or 2 to about 7, depending on the other components of the 1% solution. In an embodiment, the pH of a use composition can be from about 2 to about 7 depending on the other components.

Some examples of representative concentrations of ingredients useful in the present methods of making medium chain peroxycarboxylic acid compositions can be found in Tables G and H, in which the values are given in wt-% of the ingredients in reference to the total composition weight. In certain embodiments, the proportions and amounts in Tables G-H can be modified by "about". The present compositions also include compositions in which these combinations of ingredients have come to equilibrium forming medium chain peroxycarboxylic acid.

TABLE G

| Ingredient | wt-% | wt-% | wt-% | wt-% | wt-% | wt-% | wt-% | wt-% |
|---|---|---|---|---|---|---|---|---|
| medium chain carboxylic acid | 1-10 | 3-8 | 4-6 | 2-8 | 3-6 | 1-10 | 3-8 | 3-6 |
| solubilizer | 1-80 | 2-70 | 3-65 | 5-70 | 10-65 | 1-25 | 3-15 | 4-10 |
| carrier | 0-98 | 5-90 | 10-80 | 0.2-60 | 5-20 | 5-97 | 15-70 | 30-75 |

TABLE H

| Ingredient | wt-% | wt-% | wt-% | wt-% | wt-% | wt-% | wt-% | wt-% |
|---|---|---|---|---|---|---|---|---|
| medium chain carboxylic acid | 1-10 | 3-8 | 4-6 | 2-8 | 3-6 | 1-10 | 3-8 | 3-6 |
| solubilizer | 1-80 | 2-70 | 3-65 | 5-70 | 10-65 | 1-25 | 3-15 | 4-10 |
| carrier | 0-98 | 5-90 | 10-80 | 0.2-60 | 5-20 | 5-97 | 15-70 | 30-75 |
| oxidizing agent | 2-30 | 2-25 | 4-20 | 2-25 | 4-20 | 2-30 | 4-20 | 6-10 |
| acidulant | 1-50 | 2-40 | 3-40 | 2-40 | 3-40 | 1-50 | 3-35 | 5-30 |
| stabilizing agent | 1-50 | 1-10 | 1-5 | 1-10 | 1-5 | 1-50 | 1-5 | 1-3 |
| defoamer | 0-50 | 0.1-20 | 0.1-10 | 0.3-3 | 0.5-2 | 0.5-1.5 | 0.3-3 | 0.3-3 |

TABLE I

| Ingredient | wt-% | wt-% | wt-% | wt-% | wt-% | wt-% |
|---|---|---|---|---|---|---|
| medium chain carboxylic acid | 1-10 | 1-10 | 1-10 | 1-10 | 1-10 | 1-10 |
| solubilizer | 1-80 | 1-80 | 1-80 | 1-25 | 1-25 | 1-25 |
| carrier | 0-98 | 0-98 | 0-98 | 5-97 | 5-97 | 5-97 |
| oxidizing agent | 2-70 | 2-50 | 2-40 | 2-60 | 2-50 | 2-30 |
| acidulant | 1-50 | 1-50 | 1-50 | 1-50 | 1-50 | 1-50 |
| stabilizing agent | 1-50 | 1-50 | 1-50 | 1-50 | 1-50 | 1-50 |
| optional defoamer | 0-20 | 0.1-10 | 0.3-3 | 0.1-20 | 0.1-10 | 0.3-3 |

The present invention may be better understood with reference to the following examples. These examples are intended to be representative of specific embodiments of the invention, and are not intended as limiting the scope of the invention.

EXAMPLES

Example 1

The Present Neutral or Alkaline Medium Chain Peroxycarboxylic Acid Compositions Effectively Clean Milk Soil from an Evaporator Tube Compositions according to the present invention were evaluated and demonstrated to provide advantageous cleaning.

Materials and Methods

A lab-scale evaporator tube apparatus was developed for evaluating the present compositions for cleaning of soil in an apparatus such as an evaporator tube. FIG. 1 schematically illustrates the test apparatus.

The evaporator tube was soiled with milk soil. 2000 g of milk was added to the reservoir. The steam was turned on and the pump was started. The stream of milk touched all sides of the tube. The evaporator ran for 10 hours (7-8 one day and 2-3 the next). During evaporation 2000 g volume of milk was maintained by adding more when needed and checking that the skin on the top of the milk in the reservoir was removed. Then the tubing and reservoir were rinsed.

The evaporator tube was cleaned with a clean-in-place program. The rinse cycle (~10-45 min) employed 2000 g of tap water in the reservoir. The pre-wash cycle (~10-30 min) employed 1.5-2.5% active NaOH or KOH in tap water (2000 g). This models the alkalinity that remains in the collected wash cycle from a previous CIP program. The rinse second rinse Cycle (~30 min) employs 2000 g of tap water, which swelled the soil. The wash Cycle (30-120 min) employed 1-2.8% of the present peroxycarboxylic acid compositions in 2000 g tap water and neutralized to desired pH with appropriate amount of NaOH, KOH, or other alkalis.

In some of the procedures, the alkaline source was added to the test composition less than 5 minutes before placing it in the reservoir and starting the wash cycle. When an intermediate pH (e.g., 8.8) was employed, the wash cycle ran until no more soil removal was observed. Then more source of alkalinity was added to the reservoir. In other procedures, the acidified form of the peroxycarboxylic acid was circulated in the evaporator for 5 min prior to adding an alkaline source in which the alkaline source was added slowly at one time unit per wt-% instead of per unit of pH. All of these methods had pH of 13 during the wash cycles.

Soil removal was observed by stopping the pump and steam every 15 minutes long enough to look down the evaporator tube. It was very apparent when the wash was removing soil. The wash cycle was continued until all soil is removed (usually 30-70 min) or for 120 min. Then the tubing and reservoir were rinsed.

Test composition KK was evaluated for soil removal in an experiment that employed the following pre-wash and wash conditions. The pre-wash included 2.5% active alkalinity (5.0% of 50% NaOH or 5.55% of 45% KOH). One wash cycle included 2.25% composition KK at pH 8.5 then brought up to 11.75 by "fly" dosing after 15 min of circulation in the hot evaporator. Another wash cycle included 2.25% composition KK at pH 13.

A control composition included commercial alkaline cleaning products. The pre-wash cycle included an alkaline commercial product yielding 5 wt-% active NaOH. The wash cycle included the alkaline commercial product to provide 4 wt-% active NaOH and a commercial chelator product, which provided 0.2 wt-% chelating agent.

Another control composition included a second commercial alkaline cleaning product to provide in the pre-wash cycle 4 wt-% active KOH. The wash cycle included 4 wt-% active KOH and 0.2 wt-% chelating agent.

Results

Tables 1-13 include data showing that the present medium chain peroxycarboxylic acid compositions effectively cleaned milk soil from a model evaporator tube. The present compositions cleaned more quickly and thoroughly than conventional compositions.

The results shown in Table 1 indicate that the present neutral or alkaline medium chain peroxycarboxylic acid composition with pH at about 9 cleaned nearly as well as the same composition at pH 13. Cleaning occurred slightly faster at the higher pH. Cleaning was advantageously rapid in both situations. Increasing the pH of a composition in the soiled apparatus from about 9 to about 12 provided additional cleaning. The results shown in Table 2 confirm these results employing a slightly different protocol for increasing pH.

The results shown in Tables 3 and 4 indicate that potassium hydroxide was an effective source of alkalinity and that the present compositions were more effective than conventional alkaline and chelating cleaning compositions. The results shown in Table 5 indicate that an amine, specifically an alkanol amine, was an effective source of alkalinity. The results shown in Tables 6 and 7 indicate that acid salt from neutralized acidulant provided effective cleaning. The composition employed for Table 7 included increased hydrogen peroxide, which increased the level of medium chain peroxycarboxylic acid. Thus, this cleaner was effective at a reduced concentration in the use composition.

The results shown in Tables 8 and 9 indicate that peroxydecanoic acid compositions provided effective cleaning. These peroxydecanoic acid compositions included defoamer and were at pH above 13.

The results shown in Table 10 and 11 indicate that peroxynonanoic acid compositions provided effective cleaning. The results shown in Table 11 indicate that peroxyisononanoic acid compositions provided effective cleaning. The compositions including peroxyisononanoic acid and nonanoic acid also exhibited reduced foam.

The results shown in Tables 12 and 13 indicate that compositions including defoamer cleaned as effectively as compositions lacking defoamer and that the composition including defoamer was more effective than conventional alkaline and chelating cleaning compositions. These compositions were at pH above 13.

A hydrogen peroxide composition also cleaned well (Table 5). This suggests that hydrogen peroxide aids in cleaning by the medium chain peroxycarboxylic acid compositions. The hydrogen peroxide may perform as a cleaner when added to penetrate a soil for a predetermined time and then placed under alkaline conditions.

TABLE 1

Cleaning of Milk Soil by Neutral or Alkaline Medium Chain Peroxycarboxylic Acid Composition.

| | | Appearance of Evaporator Tube on Visual Inspection | |
| --- | --- | --- | --- |
| STEP | Time (min) | 2.3 wt-% Composition KK at pH 13 | 2.3 wt-% Composition KK at pH 8.7 then pH 11.8 |
| Rinse | 45 | tube soiled | tube soiled |
| Pre-Wash | 10 | tube soiled | tube soiled |
| Rinse | 35 | soil swelled (Temp 57° C.) | soil swelled greatly (Temp 65° C.) |
| Wash | 15 | 90% soil removal (start pH 13) | 85% soil removal (start pH 8.6) |
| | 30 | clean tube (end pH 12.8) | 85% removal (NaOH added) |
| | 50 | | clean tube (end pH 11.6) |

TABLE 2

Cleaning of Milk Soil by Neutral or Alkaline Medium Chain Peroxycarboxylic Acid Composition.

| STEP | Time (min) | Composition KK at pH 8 then up to 12 (NaOH) |
| --- | --- | --- |
| Rinse | 45 | tube soiled |
| Pre-Wash | 10 | tube soiled |
| Rinse | 35 | soil swelled, particles in water |
| Wash | 15 | 80% soil removal (pH ramped from 2 to 6, to 8, and to 10 over first ten min) |
| | 30 | 97% soil removal, one clump (pH brought up to 12.0) |
| | 45 | 99% soil removal, two small specks |
| | 60 | clean tube |

TABLE 3

Cleaning of Milk Soil by Neutral or Alkaline Medium Chain Peroxycarboxylic Acid Composition Compared to Conventional Products.

| | | Appearance of Evaporator Tube on Visual Inspection | |
| --- | --- | --- | --- |
| STEP | Time (min) | Conventional Products | 2.3 wt-% Composition KK at pH 13 (KOH) |
| Rinse | 55 | tube soiled, thin layer | tube soiled |
| Pre-Wash | 10 | tube soiled, thin layer | tube soiled |
| Rinse | 30 | soil swelled, particles in water | soil swelled greatly |
| Wash | 15 | soil swelled more, 25% soil removal | 40% removal, intake tube out of solution. |
| | 30 | 30% soil removal (temp 68° C.) | 90% soil removal (temp 65° C.) |
| | 40 | no change | two small clumps |

TABLE 3-continued

Cleaning of Milk Soil by Neutral or Alkaline Medium Chain Peroxycarboxylic Acid Composition Compared to Conventional Products.

| STEP | Time (min) | Appearance of Evaporator Tube on Visual Inspection | |
|---|---|---|---|
| | | Conventional Products | 2.3 wt-% Composition KK at pH 13 (KOH) |
| | 45 | 40% soil removal | one small speck |
| | 50 | 50% soil removal | clean tube |
| | 60 | 65% soil removal | |
| | 75 | 93% soil removal (many tiny specks) | |
| | 85 | clean tube | |

TABLE 4

Cleaning of Milk Soil by Neutral or Alkaline Medium Chain Peroxycarboxylic Acid Composition.

| STEP | Time (min) | 2.3 wt-% Composition KK at pH 13 (KOH) |
|---|---|---|
| Rinse | 70 | tube soiled |
| Pre-Wash | 12 | tube soiled |
| Rinse | 42 | soil swelled |
| Wash | 15 | soil swelled more (temp 51° C., pH 13) |
| | 35 | 20% soil removal (temp 65° C.) |
| | 45 | 80% soil removal (temp 71° C.) |
| | 60 | clean tube (temp 75° C.) |

TABLE 5

Cleaning of Milk Soil by Hydrogen Peroxide.

| STEP | Time (min) | Hydrogen Peroxide With NaOH and Monoethanol Amine* |
|---|---|---|
| Rinse | 45 | tube soiled |
| Pre-Wash | 10 | tube soiled |
| Rinse | 42 | soil swelled, particles in water |
| Wash | 15 | soil swelled (steam not on) |
| | 30 | 87% soil removal (temp 60° C.) |
| | 45 | 95% soil removal (temp 65° C.) |
| | 60 | one small speck (temp 72° C.) |
| | 75 | clean tube |

*start with 0.5% H2O2; then 5.25% NaOH (50%) and 0.5% MEA were added at 5 min.

TABLE 6

Cleaning of Milk Soil by Neutral or Alkaline Medium Chain Peroxycarboxylic Acid Composition.

| STEP | Time (min) | 3.3 wt-% Composition BR at pH 13 (KOH) |
|---|---|---|
| Rinse | 45 | tube soiled (temp 101° F.) |
| Pre-Wash | 10 | tube soiled |
| Rinse | 38 | soil swelled slightly |
| Wash | 15 | tube soiled (temp 124° F.) |

TABLE 6-continued

Cleaning of Milk Soil by Neutral or Alkaline Medium Chain Peroxycarboxylic Acid Composition.

| STEP | Time (min) | 3.3 wt-% Composition BR at pH 13 (KOH) |
|---|---|---|
| | 45 | one small clump (temp 164° F.) |
| | 55 | clean tube (temp 166° F.) |

TABLE 7

Cleaning of Milk Soil by Neutral or Alkaline Medium Chain Peroxycarboxylic Acid Composition.

| STEP | Time (min) | 1.3 wt-% Composition BQ at pH 12.5 (KOH) |
|---|---|---|
| Rinse | 45 | tube soiled (temp 101° F.) |
| Pre-Wash | 10 | tube soiled |
| Rinse | 38 | soil swelled |
| Wash | 15 | soil swelled |
| | 30 | 50% soil removal (temp 150° F.) |
| | 45 | 90% soil removal |
| | 60 | 99% soil removal (temp 158° F.) |
| | 67 | clean tube (temp 165° F.) |

TABLE 8

Cleaning of Milk Soil by Neutral or Alkaline Medium Chain Peroxycarboxylic Acid Composition.

| STEP | Time (min) | Appearance of Evaporator Tube on Visual Inspection | |
|---|---|---|---|
| | | 1.5% Composition BT (1.7% KOH) | 1.7% Composition KK (1.8% KOH) |
| Rinse | 15 | tube soiled | tube soiled |
| Pre-Wash | 11 | tube soiled | tube soiled |
| Rinse | 35 | soil swelled (Temp 130° F.) | soil swelled (Temp 126° F.) |
| Wash | 22 | 25% soil removal (Temp 158° F.) | 15% soil removal (Temp 158° F.) |
| | 30 | 80% soil removal (Temp 170° F.) | 50% soil removal (Temp 167° F.) |
| | 37 | clean tube (Temp 175° F.) | 90% soil removal (Temp 169° F.) |
| | 48 | | clean tube (Temp 171° F.) |

TABLE 9

Cleaning of Milk Soil by Neutral or Alkaline Medium Chain Peroxycarboxylic Acid Composition.

| STEP | Time (min) | Appearance of Evaporator Tube on Visual Inspection | |
|---|---|---|---|
| | | 1.5% Composition BT (1.7% KOH) | 2% Composition BV (1.2% KOH) |
| Rinse | 13 | tube soiled | tube soiled |
| Pre-Wash | 11 | tube soiled | tube soiled |
| Rinse | 30 | soil swelled greatly | soil swelled greatly |
| Wash | 15 | tube soiled (Temp 143° F.) | soil slightly thinner (Temp 156° F.) |

TABLE 9-continued

Cleaning of Milk Soil by Neutral or Alkaline Medium
Chain Peroxycarboxylic Acid Composition.

| | | Appearance of Evaporator Tube on Visual Inspection | |
|---|---|---|---|
| STEP | Time (min) | 1.5% Composition BT (1.7% KOH) | 2% Composition BV (1.2% KOH) |
| | 33 | 90% soil removal (Temp 170° F.) | clean tube, foam (Temp 177° F.) |
| | 44 | clean tube (Temp 169° F.) | |

TABLE 10

Cleaning of Milk Soil by Neutral or Alkaline Medium Chain
Peroxycarboxylic Acid Composition Including Peroxynonanoic Acid.

| STEP | Time (min) | 2.5 wt-% Composition BP at pH 12 (NaOH) |
|---|---|---|
| Rinse | 45 | tube soiled (temp 101° F.) |
| Pre-Wash | 10 | tube soiled |
| Rinse | 42 | soil swelled, particles in water (temp 115° F.) |
| Wash | 15 | 25% soil removal, slight foam (temp 125° F.) |
| | 30 | few tiny specks |
| | 40 | clean tube |

TABLE 11

Cleaning of Milk Soil by Neutral or Alkaline Medium
Chain Peroxycarboxylic Acid Composition.

| | | Appearance of Evaporator Tube on Visual Inspection | |
|---|---|---|---|
| STEP | Time (min) | 1.7% Composition BS (1.7% KOH) | 1.5% Composition CB (1.8% KOH) |
| Rinse | 11 | tube soiled | tube soiled |
| Pre-Wash | 10 | tube soiled | tube soiled |
| Rinse | 35 | soil swelled (Temp 115° F.) | soil swelled (Temp 120° F.) |
| Wash | 22 | tube soiled (Temp 132° F.) | tube soiled (Temp 130° F.) |
| | 44 | clean tube, minimal foam (Temp 157° F.) | 15% soil removal (Temp 160° F.) |
| | 55 | | clean tube (Temp 170° F.) |

TABLE 12

Cleaning of Milk Soil by Neutral or Alkaline Medium
Chain Peroxycarboxylic Acid Composition.

| | | Appearance of Evaporator Tube on Visual Inspection | |
|---|---|---|---|
| STEP | Time (min) | 1.5% Composition KK" (1.7% KOH) | Conventional Products |
| Rinse | 10 | tube soiled | tube soiled |
| Pre-Wash | 17 | tube soiled | tube soiled |
| Rinse | 35 | soil swelled greatly | soil swelled greatly |
| Wash | 22 | 20% soil removal | 20% soil removal |
| | 42 | 70% soil removal (Temp 163° F.) | 40% soil removal (Temp 160° F.) |
| | 58 | few tiny specks | 80% soil removal (Temp 162° F.) |

TABLE 12-continued

Cleaning of Milk Soil by Neutral or Alkaline Medium
Chain Peroxycarboxylic Acid Composition.

| | | Appearance of Evaporator Tube on Visual Inspection | |
|---|---|---|---|
| STEP | Time (min) | 1.5% Composition KK" (1.7% KOH) | Conventional Products |
| | 62 | clean tube (Temp 163° F.) | |
| | 80 | | clean tube (Temp 160° F.) |

TABLE 13

Cleaning of Milk Soil by Neutral or Alkaline Medium
Chain Peroxycarboxylic Acid Composition.

| | | Appearance of Evaporator Tube on Visual Inspection | |
|---|---|---|---|
| STEP | Time (min) | 1.5% Composition KK (1.7% KOH) | 1.5% Composition KK" (1.7% KOH) |
| Rinse | 10 | tube soiled | tube soiled |
| Pre-Wash | 13 | tube soiled | tube soiled |
| Rinse | 31 | soil swelled (Temp 135° F.) | soil swelled (Temp 127° F.) |
| Wash | 31 | 25% soil removal (Temp 140° F.) | tube soiled (Temp 137° F.) |
| | 52 | 90% soil removal (Temp 168° F.) | 85% soil removal (Temp 167° F.) |
| | 58 | few tiny specks (Temp 170° F.) | clean tube |
| | 62 | clean tube (Temp 170° F.) | |

Example 2

The Present Neutral or Alkaline Medium Chain
Peroxycarboxylic Acid Compositions Effectively
Clean Milk Soil from a Heat Exchanger Compositions according to the present invention were evaluated and demonstrated to provide advantageous cleaning.

Materials and Methods

Figure 2:
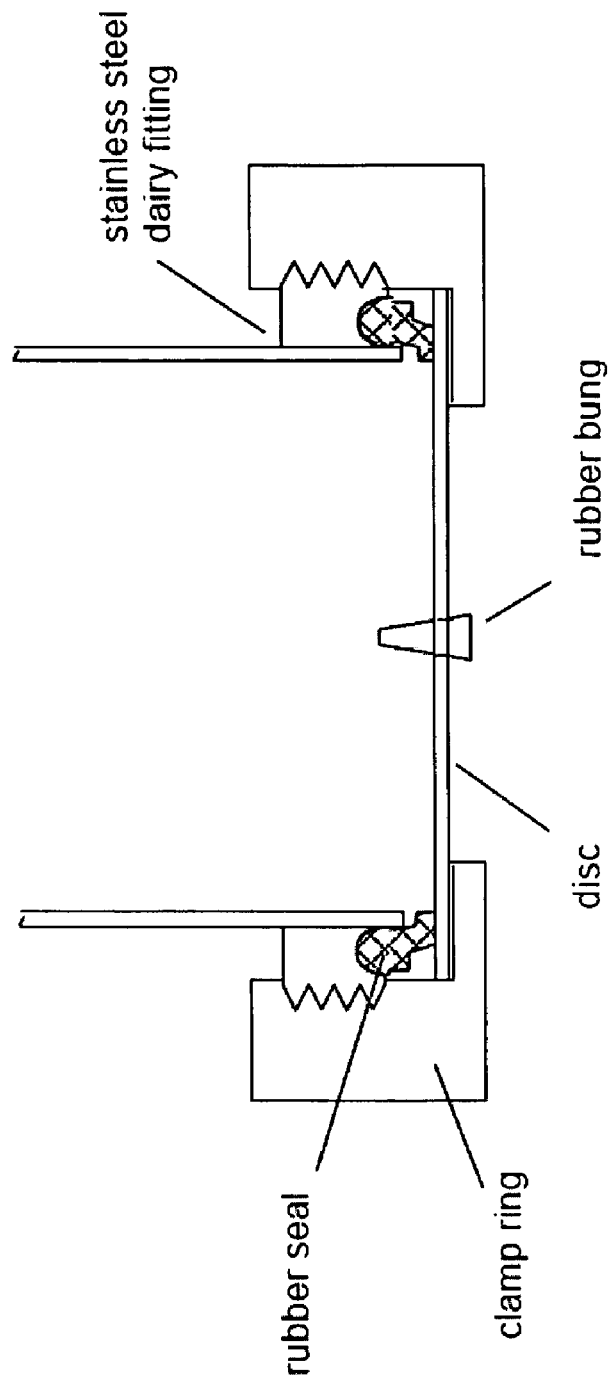
FIG. 2 schematically illustrates a lab-scale heat exchanger apparatus employed for evaluating the present compositions for cleaning of soil in an apparatus such as a heat exchanger.

A lab-scale heat exchanger apparatus was developed for evaluating the present compositions for cleaning of soil in an apparatus such as a heat exchanger. FIG. 2 schematically illustrates the test apparatus. The test apparatus included disks 88.5 mm in diameter and 1.5 mm thick with a central 4.8 mm diameter hole cut from a 316 stainless steel sheet. These were mounted in a standard 3" stainless steel bezel seat fitting as shown in FIG. 2. A 82 mm bezel seated EPDM rubber ring was used to give a clean-edged seal. The diameter of the area available for fouling was 80 mm. The discs were prepared for fouling by rinsing at room temperature in 2% NaOH, then 5% $HNO_3$, and finally in distilled water.

Figure 3:
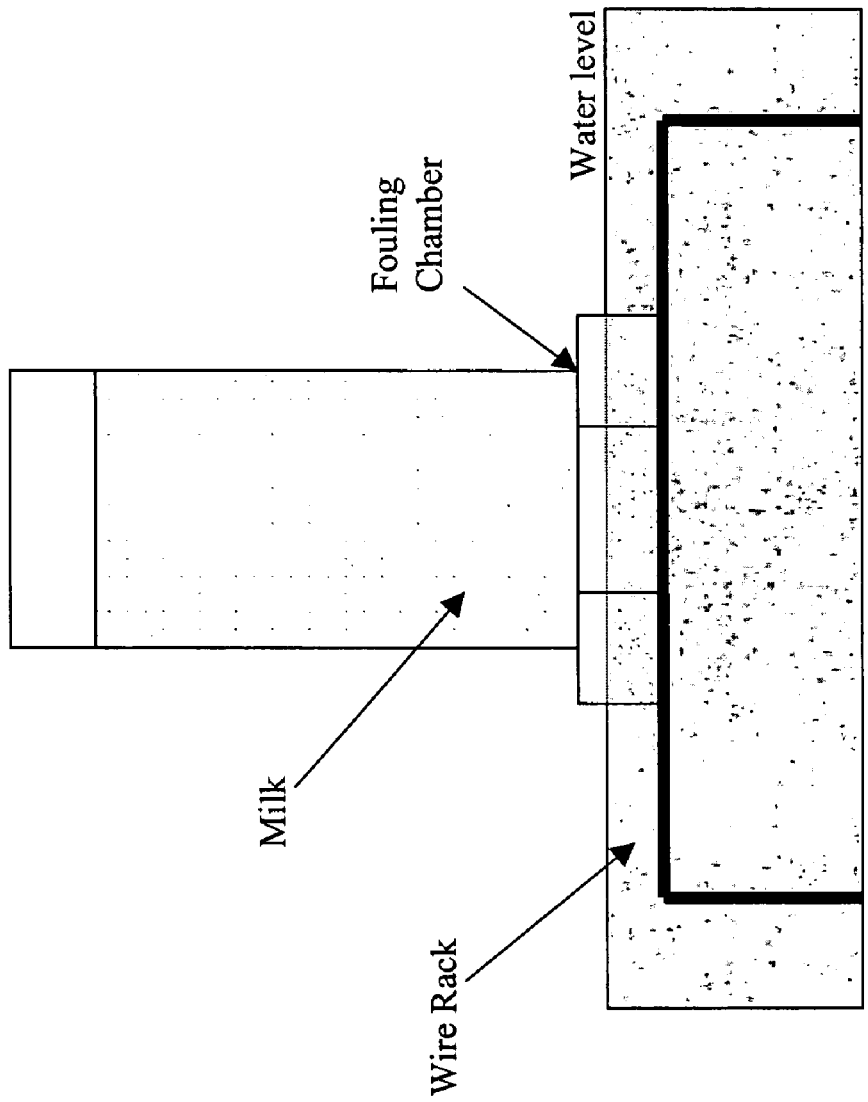
FIG. 3 schematically illustrates the apparatus used for soiling the apparatus of FIG. 2 with milk.

The heat exchanger was soiled with milk. Prepared disks were fitted into fouling chambers in triplicate and fouled with ⅓ gallon whole milk each (initially at 40°) for 4.5 hours in a water bath at 96° C. with no agitation. The chamber was covered with aluminum foil to minimize evaporative moisture loss. During the fouling period a 6 mL plastic syringe with a U-tube was used to extract any gases that collected beneath the disc. The water bath was covered with plastic wrap to prevent evaporation and contain heat. FIG. 3 schematically illustrates the apparatus used for soiling with milk.

After fouling, the disc was removed from the fouling assembly and rinsed by spinning at 60 rpm in 1 L of distilled water at ambient temperatures for 1 minute. The purpose of this was to remove any residual milk present in the deposit so it would not affect the results of the analytical measurements.

Figure 4:
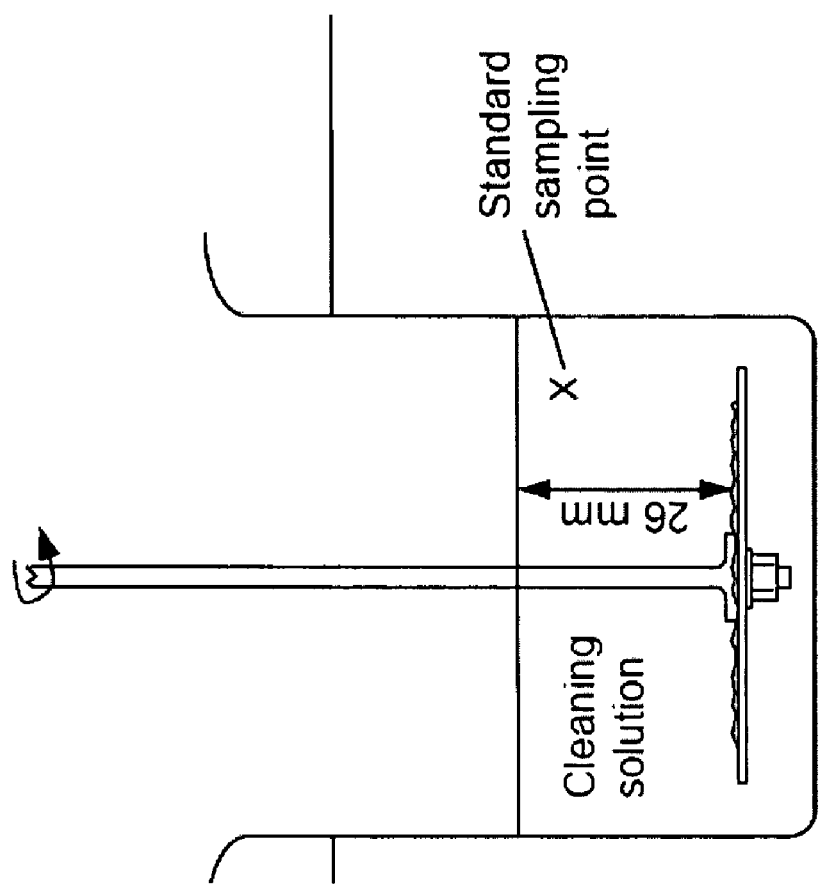
FIG. 4 schematically illustrates the arrangement of the disk in the apparatus of FIG. 2 for the cleaning measurements.

FIG. 4 schematically illustrates the arrangement of the disk for the cleaning measurements. The disc was mounted on a mixing bit with a screw and fastened to an overhead mixer, which allowed variable speed control. The upper limit of Reynolds number in the laminar flow regime for spinning disks is not well defined, but has been estimated to be of the order of $10^4$ to $10^5$ depending on the condition of the surface and balance of the disc. In this work a maximum disc speed of 60 rpm was used, which corresponds to a Reynolds number of ~68000 at 80° C.

The mounted disc was lowered into a 100 mm ID 1 L beaker containing 1 L of cleaning solution which was maintained at 80° C. on a stirring hot plate. The depth of the disk below the liquid surface was 26 mm. Once the spinning disc was submerged, 3 mL samples were extracted at various intervals from the point marked in FIG. 4, using a syringe. After 15 minutes the disc was removed from the beaker. The cleaning solution was then mixed thoroughly and a final, mixed sample taken. The area of deposit exposed to the cleaning solution was 50 cm².

The absorbance of the samples collected during cleaning were measured at 280 nm using a UV Spectrophotometer. This was calibrated to an absorbance of zero for each pure cleaning solution used.

Panels were weighed before soiling, after soiling, and after cleaning on an analytical balance to a precision of +/−0.0001 g. All measurements were taken after the soil was dry to ambient conditions.

This method was adapted from Morison, K. R., 2003, "Spinning Disc Measurement of Enhanced Cleaning of Milk Protein Deposits", *Heat Exchanger Fouling and Cleaning: Fundamentals and Applications*, Paper #383

Results

Burned-on milk soil disks were cleaned using compositions and methods according to the present invention and control compositions.

Experiment 1

Figure 5:
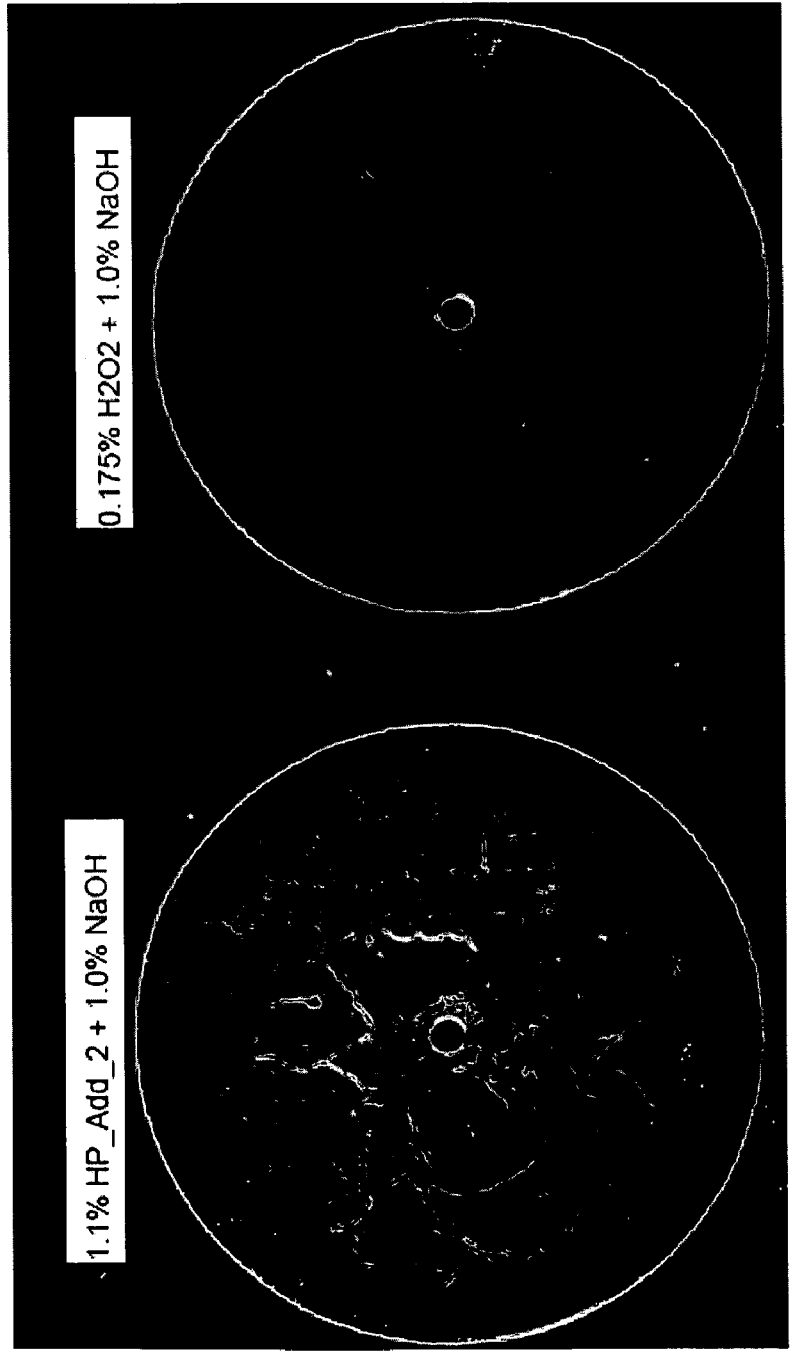
FIG. 5 presents a photograph of results obtained in Experiment 1 of Example 2.

In experiment 1, the test composition included 1.1% Composition BL plus 1% NaOH and the control composition included 0.175% $H_2O_2$ plus 1.0% NaOH. The pH of the test composition was less than the pH of the control composition. Composition BL disrupted the soil more than the control composition. Composition BL plus NaOH caused fractures and reduced adhesion to the disk. These results are shown in the photographs in FIG. 5.

Experiment 2

Figure 6:
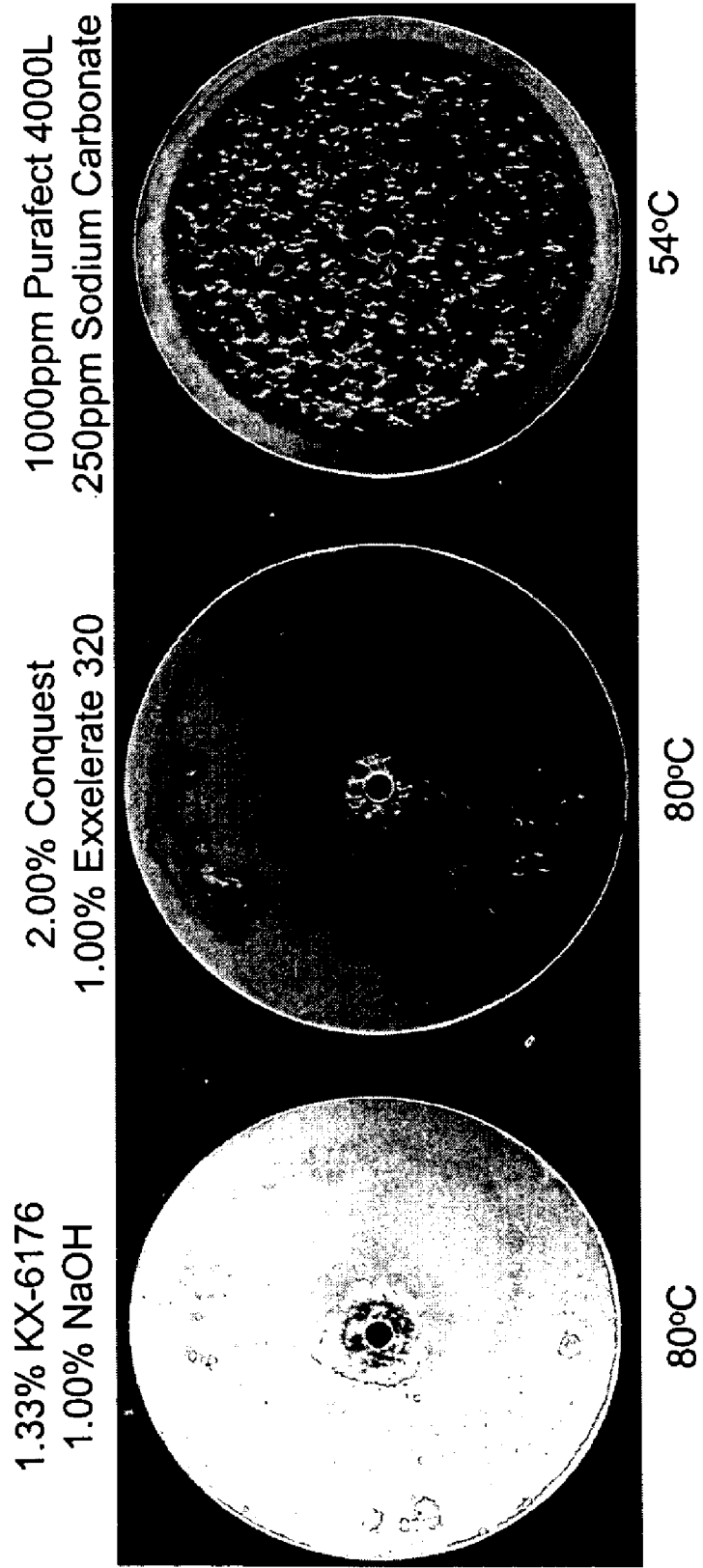
FIG. 6 presents a photograph of results obtained in Experiment 2 of Example 2.

In experiment 2, the test composition included 1.33% Composition KK plus 1% NaOH. The first control composition included commercial alkaline and chelator products, which yielded a composition including 0.6 wt-% active NaOH and 0.7 wt-% active chelating agent blend. The pH of the test composition was less than the pH of the first control composition. The second control composition included 40 ppm subtilisin protease plus 250 ppm sodium carbonate and was cleaned at a lower temperature suitable for enzyme activ- ity. The disks were cleaned for 30 min. Composition KK plus NaOH disrupted the soil more than the control compositions. The results are summarized in Table 14 and illustrated in FIG. 6.

TABLE 14

Cleaning of Milk Soil by Neutral or Alkaline Medium Chain Peroxycarboxylic Acid Composition Compared to Conventional Products.

| Composition | % Soil Remaining |
|---|---|
| Test - KK plus NaOH | 2 |
| First Control | 15 |
| Second Control | 59 |

Experiment 3

In experiment 3, the first test composition included 1.3% Composition BP plus 0.8% NaOH. The second test composition included 1.3% Composition BM plus 0.9% NaOH. The control composition included commercial alkaline and chelator products, which yielded a composition including 0.6 wt-% active NaOH and 0.7 wt-% active chelating agent blend. The test composition pH was less than the pH of the control composition. The disks were cleaned for 15 min at 85° C.

Composition BP plus NaOH removed 95% of the mass of the soil. Composition BM plus NaOH removed 96% of the mass of the soil. The control composition removed 83% of the mass of the soil. The present compositions outperformed the conventional caustic/chelator system for soil removal. Photos of the soil removal and analysis of the bleaching were obtained (not shown).

Experiment 4

In experiment 4, the first test composition included 1.3% Composition BO in deionized water at 180° F. This composition was titrated to determine that it included 1400 ppm $H_2O_2$ and 570 ppm peroxynonanoic acid (PONA). In the cleaning apparatus, the pH of the composition was increased to 8.7 by addition of NaOH. After 15 min, a sample of the cleaning composition was taken for titration. The pH of the cleaning composition was raised to 11.4 with NaOH and cleaning continued for an additional 15 min of cleaning.

After 15 min of cleaning at pH 8.7, the composition was titrated to determine that it included 1400 ppm $H_2O_2$ and 70 ppm PONA. The concentration of PONA had decreased, but not the concentration of hydrogen peroxide. After 15 min of cleaning at pH 11.4, the composition was titrated to determine that it included 300 ppm $H_2O_2$ and no PONA. The concentration of hydrogen peroxide had decreased, as did the concentration of PONA.

The test composition thoroughly cleaned the disk. Photos of the soil removal were obtained (not shown).

Example 3

The Present Neutral or Alkaline Medium Chain Peroxycarboxylic Acid Compositions Effectively Clean Whey and Milk Soil from a Pasteurizer Compositions according to the present invention were evaluated and demonstrated to provide advantageous cleaning.

Materials and Methods

Cleaning Whey Soil

Pre-pasteurized whey (~6.2% Brix) was obtained from a commercial source. The whey was used to soil APV Model Jr. high temperature short time pasteurizer (HTST). Ten gallons of whey were added to the HTST and allowed to recirculate for 11 hours at a flow rate of ~0.7 gpm with the heating section set at 209° F. The temperature at the end of the hold tube was 182° F. After 11 hours, the whey was drained and the other 10 gallons were added and recirculated for 11 more hours.

After 22 hours of soiling, the heating section was removed and inspected. Very heavy organic soil was present on each plate. This level of soiling caused the pressure to rise from 11.8 psi at the beginning of the soiling to 41.5 psi at the end of the soiling. Every other plate was paired with a clean plate and reinserted into the heating section. The remaining half of the plates were placed in a sealed plastic container with wetted sponges to slow the dehydration of the soil.

The soiled plates that remained in the HTST were cleaned with a conventional cleaning program described in Table 15.

TABLE 15

Conventional Cleaning Program for Whey Soil

|  | Concentration | Temp | Time |
| --- | --- | --- | --- |
| Pre-rinse |  |  | 10 min |
| Caustic Wash | 30,000 ppm (1.5% NaOH) | 185° F. (172° F. Hold Tube) | 45 min. |
| Rinse |  |  | 10 min |
| Acid Wash | 10,000 ppm | 160° F. (149° F. Hold Tube) | 30 min. |
| Post Rinse |  |  | 10 min |

After the conventional cleaning process, the soiled plates that had been removed from the HTST were reinserted in the heating section of the apparatus and cleaned according to the following program with present composition BW.

TABLE 16

Cleaning Program for Whey Soil Employing a Composition of the Present Invention

|  | Concentration | Temp | Time |
| --- | --- | --- | --- |
| Pre-rinse |  |  | 10 min |
| Pretreat with composition BW | 7,500 ppm | 190° F. (172° F. Hold Tube) | 5 min |
| Caustic Wash | 12,400 ppm (1.5% NaOH) |  | 40 min. |
| Rinse |  |  | 10 min |
| Acid Wash | 10,000 ppm | 160° F. (148° F. Hold Tube) | 30 min. |
| Post Rinse |  |  | 10 min |

A brief pressure rise in the system of about 5 psi was observed approximately 2 minutes after the caustic override of the medium chain peroxycarboxylic acid composition. The pressure rise lasted a few seconds. There was no evidence of pump cavitation throughout the cleaning steps. A small (~0.5") foam layer was present in the constant level tank during the caustic wash.

Cleaning Milk Soil

Initially 9 gallons of raw milk were added to the HTST system and allowed to recirculate for 12 hours at a flow rate of ~0.7 gpm, with the heating section set at 209° F. The temperature at the end of the hold tube was 182° F. After 12 hours, the milk was drained and another 9 gallons were added and recirculated for 12 more hours.

After 24 hours of soiling, the heating section was removed and inspected. The pressure during the raw milk soiling was relatively constant raising from 9 to 11 psi at the end of the soiling process. Heavy burnt on organic soil was present on the plates where the raw milk entered the heating section from the regeneration section. There was some light organic soil and mineral soil on the other plates. Every other soiled plate was paired with a clean plate and reinserted into the heating section. The remaining half of the plates were placed in a sealed plastic container with wetted sponges to slow soil dehydration.

The soiled plates that remained in the HTST were cleaned with a conventional cleaning program described in Table 17.

TABLE 17

Conventional Cleaning Program for Milk Soil

|  | Concentration | Temp | Time |
| --- | --- | --- | --- |
| Pre-rinse |  | ~130° F. | 10 min |
| Wash with Caustic and Chelator | 5,400 ppm caustic 7,000 ppm chelator | 190° F. (172° F. Hold Tube) | 60 min |
| Post Rinse |  |  | 10 min |

After the conventional cleaning process, the soiled plates that had been removed from the HTST were reinserted in the heating section of the apparatus and cleaned according to the following program with present composition BW.

TABLE 18

Cleaning Program for Milk Soil Employing the a Composition of the Present Invention

|  | Concentration | Temp | Time |
| --- | --- | --- | --- |
| Pre-rinse |  | ~130° F. | 10 min |
| Wash with Composition BW plus Caustic | 7,000 ppm peroxycarboxylic acid 5,700 ppm caustic | 190° F. (175° F. Hold Tube) | 5 min 55 min |
| Post Rinse |  |  | 10 min |

Results

The results are summarized below in Tables 19 and 20.

Whey Soil

Some burned on soil remained after the conventional washing program.

After washing according to the present method and employing a composition according to the present invention, the plates were immediately removed and inspected. There was no evidence of any remaining soil on any of the plates. Photos of the soil removal were obtained (not shown).

TABLE 19

Whey HTST Cleaning Results

|  | Conventional Program | Inventive Program |
| --- | --- | --- |
| Cleanliness | Burnt on protein residues | Completely visually clean |
| Sodium Concentration | 8622 ppm | 3639 ppm (~60% reduction) |
| Electrical Conductivity | 77.1 mS/cm | 23.8 mS/cm (~70% reduction) |

Milk Soil

Some burned on soil remained on the heavily soiled plates after the conventional washing program. The composition of the remaining soil had FTIR peaks consistent with amide protein, alkyl, and ester compounds. Elemental analysis confirmed that the soil was mainly organic, with inorganic elemental ratios of 41% sodium, 40% sulfur, and 19% calcium—consistent with a proteinaceous soil.

After washing according to the present method and employing a composition according to the present invention, all of the burnt-on proteinaceous soil was removed. There was some calcium phosphate residues remaining on a few of the plates. Analysis of the remaining soil revealed FTIR peaks consistent with an inorganic soil. Elemental analysis confirmed that the soil was mainly inorganic, with inorganic elemental ratios of 22% phosphorous and 78% calcium—consistent with a calcium phosphate soil. It is expected that an acid cleaning step or addition of chelator would have removed the calcium phosphate soil. Photos of the soil removal were obtained (not shown).

TABLE 20

Raw Milk HTST Cleaning Results

|  | Conventional Program | Inventive Program |
| --- | --- | --- |
| Cleanliness | Burnt on protein residues | Some calcium phosphate residues |
| Sodium Concentration | 3525 ppm | 3421 ppm (~3% reduction) |
| Electrical Conductivity | 30.0 mS/cm | 22.1 mS/cm (~16% reduction) |

The inventive cleaning programs have substantially lower sodium levels compared to conventional cleaning programs, and moderately lower electrical conductivity levels compared to a conventional low alkalinity HTST cleaning program.

Example 4

The Present Neutral or Alkaline Medium Chain Peroxycarboxylic Acid Compositions Effectively Remove Biofilm Compositions according to the present invention were evaluated and demonstrated to provide advantageous removal of biofilm.

Materials and Methods

Biofilm was grown on a stainless steel coupon. The biofilm formed from *Pseudomonas aeruginosa* grown for 14-days on the coupon at ambient temp with high sheer conditions. High sheer conditions were produced by continuous stirring of the growth medium inside the vessel containing the stainless steel coupons. As the microorganisms grow and attach to the surface of the stainless steel there is a constant sheer force on the surface of the growing biofilm. The test compositions listed in Table 21 were made up in synthetic hard water (500 ppm hardness). The biofilm was contacted with the test composition for a total of 3 and 6 minutes (Table 21) at 160° F. After this time, cleaning was stopped by rinsing the biofilm with the neutralizer D/E broth. The remaining biofilm was stained for visualization by fluorescence imaging with acridine orange stain under 40× magnification, one frame left of center.

TABLE 21

Cleaning Programs Employed in the Present Example

| 1 | | 2 | | 3 | |
| --- | --- | --- | --- | --- | --- |
| A | B | A | B | A | B |
| 0.53% KK (1 min) | 0.53% KK (1 min) | 0.53% HP add 12 (1 min) | 0.53% HP add 12 (1 min) | 3% of 50% NaOH (3 min) | 3% of 50% NaOH (6 min) |
| Add 1.5% of 50% NaOH (2 min) | Add 1.51% of 50% NaOH (5 min) | Add 1.23% of 50% NaOH (2 min) | Add 1.23% of 50% NaOH (5 min) | — | — |

Results

Figure 7:
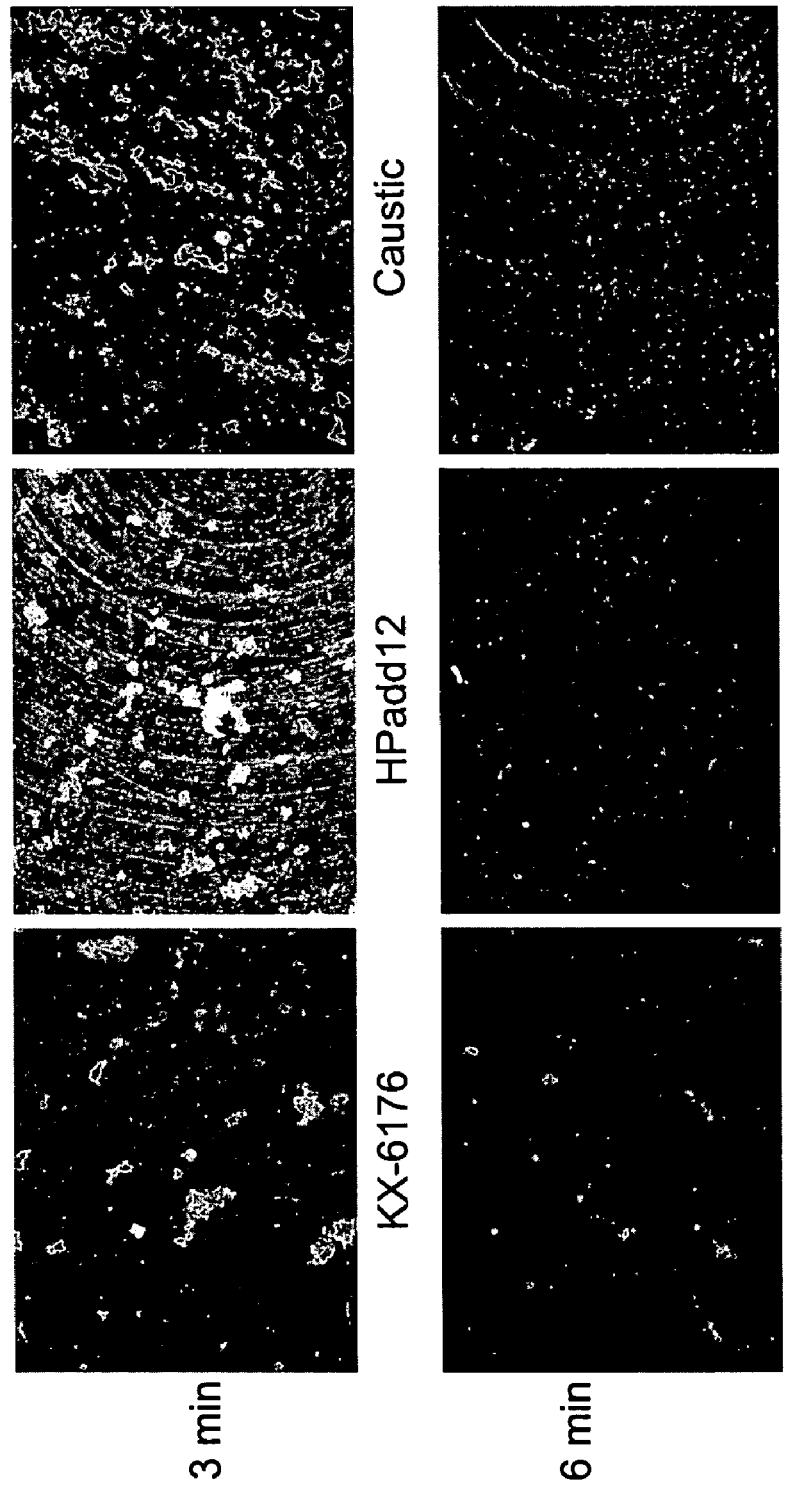
FIG. 7 presents a photograph of results for biofilm removal obtained in Example 4.

After three minutes, composition KK outperformed both composition BW and the caustic cleaning programs. After 6 minutes, composition BW showed the greatest cleaning performance followed closely by KX-6176 and lastly by caustic. Effervescence was observed in the composition KK flasks earlier in the time point than the composition BW flasks. These results are illustrated in FIG. 7.

There were no recoverable viable microorganisms from any of the coupons tested. However, enrichment of treated coupons revealed survivors on one of two coupons treated with caustic for 3 min. The fact that all of the microorganisms can be killed without removing all of the cellular debris is useful for measuring cleaning performance because the "footprint" of the biofilm that is left behind could serve as a location for new biofilm to attach.

Example 5

The Present Neutral or Alkaline Medium Chain Peroxycarboxylic Acid Compositions Effectively Remove Food Soil from Tile Compositions according to the present invention were evaluated and demonstrated to provide advantageous removal of food soil from tile.

Materials and Methods

New 3"×3" white vinyl tiles were weighed, soiled, and reweighed after drying for 24 hours. The chosen soil was the "Hot Point Soil." This was a lab prepared food soil. It was applied using a 1" paint brush (~1.5 g of soil is smeared on the rough side of the white vinyl tile). After drying 24 hours, the tile was weighed to determine the initial amount of dry soil present on the tile.

The test composition was 1.30% Composition BP in city water. A soiled tile was placed in the test composition. The pH of the test composition was then raised to 11.6 by drop-wise addition of NaOH. Cleaning was observed as the pH was increased.

Results

The tile was exposed to composition BP at pH 2.8 for 10 minutes. No soil removal was noticed. The test was observed at the pH was increased to 8.7 by adding NaOH (to 0.084% NaOH). Not much soil removal was seen at this point. Soil was noted coming off the tile between pH 9.5 and 10. At pH 10.5 most of the soil was removed from the vinyl tile. The pH was increased up to 11.6, at which time the experiment was stopped.

After letting the tile dry overnight, its appearance the was mostly white, with only a few areas of noticeable soil/stain remaining. Significant amount of soil removal was obtained.

Changing the order of addition of the present composition and the source of alkalinity indicated that very little cleaning occurred when the source of alkalinity was added first. This indicates that one method for cleaning with the present compositions is to first apply the present medium chain peroxycarboxylic acid composition and then to apply a source of alkalinity.

Example 6

Antimicrobial Efficacy of the Neutral or Alkaline Medium Chain Peroxycarboxylic Acid Compositions Compositions according to the present invention were evaluated and demonstrated advantageous antimicrobial activity against microbes such as gram negative bacteria, gram positive bacteria, fungi, spores, viruses, and mycobacteria.

Materials and Methods

Antimicrobial activity was determined according to three well established methods. Activity against *Mycobacterium bovis* was evaluated using a Quantitative Tuberculocidal (QTB) test adapted from U.S. EPA, Data Call-In Notice for Tuberculocidal Effectiveness Data for All Antimicrobial Pesticides with tuberculocidal claims. Composition KK was adjusted to several pH levels in synthetic hard water (400 ppm hardness) and tested for activity in the presence of a 5% organic soil load. The test determined the tuberculocidal effectiveness of a disinfectant following the EPA guidelines for the quantitative tuberculocidal procedure. Tuberculocidal activity of the present compositions was determined by exposing a one mL aliquot containing *Mycobacterium* to 9.0 mL of the desired concentration of the test substance at the desired temperature. After the specified contact time, one mL of the test solution containing the microorganism was neutralized and enumerated for survivors.

Activity against spores of *Clostridium sporogenes* ATCC 3584 was evaluated using the Sporicidal Activity of Disinfectants, Official Methods of Analysis of the Association of Official Analytical Chemists, 17$^{th}$ Edition, AOAC Official Method 966.04, Chapter 6, pages 12-14. Composition KK was adjusted to pH 6.5 in synthetic hard water (400 ppm hardness) and tested for activity in the presence of a 5% organic soil load. Spores of *Clostridium sporogenes* ATCC 3584 were dried on porcelain penicylinders. The penicylinders were individually exposed to 10 mL of the test substance at the desired concentration, temperature and for the desired contact time. After which each penicylinder was removed aseptically and transferred to a neutralizing subculture medium. A peroxyacetic acid composition was also tested by this procedure.

Activity against fungus, *Trichophyton mentagrophytes* ATCC 9533, was evaluated using the Fungicidal Activity of Disinfectants using *Trichophyton mentagrophytes*, Official Methods of Analysis of the Association of Official Analytical Chemists, paragraph 955.17. Composition KK was adjusted to pH 6.5 in synthetic hard water (400 ppm hardness) and tested for activity in the presence of a 5% organic soil load. Antimicrobial efficacy was determined by exposing stainless steel penicyclinders containing dried *Trichophyton mentagrophytes* to 10 mL of the test substance at the desired concentration, temperature and for the desired contact time. After which each penicylinder was removed aseptically and transferred to a neutralizing subculture medium. A peroxyacetic acid composition was also tested by this procedure.

Results

Tables 22-24 include data showing that the present medium chain peroxycarboxylic acid compositions had antimicrobial activity when tested against bacteria, fungi, and spores in several different types of tests.

The data presented in Table 22 demonstrate that the present compositions exhibited effective antimicrobial activity against *Mycobacterium bovis*. The present composition (KK) provided greater than 5 log reduction of *M. bovis* BCG at concentrations of medium chain peroxycarboxylic acid of 200 ppm and greater at pH of about 6 to about 9 in times as short as 5 or 10 min. These results indicate that the compositions of the present invention can be employed as a tuberculocidal agent. By way of comparison, a peroxyacetic acid composition was as effective only at concentrations of peroxyacetic acid at or exceeding 1250 ppm (data not shown).

The data presented in Table 23 demonstrate that the neutral or alkaline medium chain peroxycarboxylic acid compositions exhibited superior antimicrobial activity against bacterial spores compared to conventional short chain peroxycarboxylic acid antimicrobials. Bacterial spores are difficult to kill. The neutral or alkaline medium chain peroxycarboxylic acid composition at 400 ppm peroxycarboxylic acid and pH 6.5 achieved sterilant efficacy within 10 hrs at ambient temperature. The present composition resulted in greater kill at equal or lower concentrations of antimicrobial active. These results indicate that the present compositions exhibited superior antimicrobial activity compared to conventional antimicrobials.

The data presented in Table 24 demonstrate that the present compositions exhibited significant antimicrobial activity against fungus. The present compositions exhibited antifungal activity at low levels of medium chain peroxycarboxylic acid. The present composition at 400 ppm was as effective as peroxyacetic acid at 1000 ppm.

TABLE 22

Antimicrobial Activity of Neutral or Alkaline Medium Chain Peroxycarboxylic Acid Composition Against Mycobacteria at Several pH.

| [POOA] (ppm) | pH of Composition | Log Reduction (5 min) | Log Reduction (10 min) |
| --- | --- | --- | --- |
| 100 | 6.1 | 4.7 | 4.8 |
| 100 | 7.2 | 4.5 | 4.7 |
| 200 | 6.1 | >6 | >6 |
| 200 | 7.1 | 5.0 | 5.2 |
| 300 | 6.0 | 5.7 | >6 |
| 300 | 7.0 | 5.4 | 6.0 |
| 400 | 6.1 | >5.8 | >5.8 |
| 400 | 7.1 | >6.6 | >6.6 |
| 400 | 8.7 | >6.6 | >6.6 |
| 600 | 6.0 | >5.8 | >5.8 |
| 600 | 7.1 | >6.6 | >6.6 |

TABLE 22-continued

Antimicrobial Activity of Neutral or Alkaline Medium Chain
Peroxycarboxylic Acid Composition Against Mycobacteria at Several pH.

| [POOA] (ppm) | pH of Composition | Log Reduction (5 min) | Log Reduction (10 min) |
|---|---|---|---|
| 600 | 8.0 | >6.6 | >6.6 |
| 800 | 6.1 | >5.8 | >5.8 |
| 800 | 7.0 | >6.6 | >6.6 |
| 800 | 8.0 | >6.6 | >6.6 |

TABLE 23

Antimicrobial Activity of Neutral or Alkaline Medium Chain
Peroxycarboxylic Acid Composition Against Bacterial Spores.

| Peroxycarboxylic Acid | pH | ppm | Exposure Time | Exposure Temp | # Negative Tubes/ # Tubes Tested |
|---|---|---|---|---|---|
| Peroxyoctanoic Acid | 6.5 | 400 | 10 hrs | Ambient | 60/60 |
| Peroxyacetic Acid | 6.5 | 1000 | 10 hrs | Ambient | 59/60 |

TABLE 24

Antimicrobial Activity of Neutral or Alkaline Medium Chain
Peroxycarboxylic Acid Composition Against Fungus.

| Peroxycarboxylic Acid | pH | ppm | Exposure Time | Exposure Temp | # Negative Tubes/ # Tubes Tested |
|---|---|---|---|---|---|
| Peroxyoctanoic Acid | 6.5 | 400 | 5 min | Ambient | 10/10 |
| Peroxyacetic Acid | 6.5 | 1000 | 5 min | Ambient | 10/10 |

Example 7

Stability of Neutral or Alkaline Compositions of Medium Chain Peroxycarboxylic Acid Compositions according to the present invention were evaluated and demonstrated sufficient stability of the medium chain peroxycarboxylic acid at neutral and alkaline pH.

Materials and Methods

Composition KK (Table 26, Example 9) was used in this example. Composition KK was diluted with water to 4, 6, or 8 wt-% of composition KK. An alkaline composition (e.g., 50% NaOH) was added to bring the pH of the diluted composition to 6.5. At this pH, the neutralized phosphoric acid from composition KK can buffer the pH. From pH 6.5, 50% NaOH was added until the pH was about 6, about 7, or about 8.

TABLE 25

Stability of Medium Chain Peroxycarboxylic Acid in Diluted
Compositions at pH 6 to 8

| KK (wt-%) | pH | Time (hrs) | [POOA] (ppm) |
|---|---|---|---|
| 400 | 6.06 | 0 | 327 |
|  |  | 5 | 322 |
|  |  | 23 | 196 |

TABLE 25-continued

Stability of Medium Chain Peroxycarboxylic Acid in Diluted
Compositions at pH 6 to 8

| KK (wt-%) | pH | Time (hrs) | [POOA] (ppm) |
|---|---|---|---|
| 400 | 7.05 | 0.7 | 238 |
|  |  | 2.7 | 201 |
|  |  | 5.7 | 129 |
| 400 | 8.67 | 0.85 | 241 |
|  |  | 2.85 | 173 |
|  |  | 5.85 | 84 |
| 600 | 6.03 | 0 | 542 |
|  |  | 2 | 494 |
|  |  | 4 | 442 |
|  |  | 6 | 338 |
|  |  | 23 | 125 |
| 600 | 7.09 | 0.75 | 374 |
|  |  | 2.75 | 263 |
|  |  | 5.75 | 184 |
| 600 | 7.97 | 1.0 | 322 |
|  |  | 3.0 | 281 |
|  |  | 6.0 | 168 |
| 800 | 6.09 | 0 | 686 |
|  |  | 23 | 144 |
| 800 | 7.04 | 0.8 | 598 |
|  |  | 2.8 | 495 |
|  |  | 5.8 | 231 |
| 800 | 7.94 | 1.0 | 494 |
|  |  | 3.0 | 142 |
|  |  | 6.0 | 131 |

Results and Conclusions

The present neutral or alkaline medium chain peroxycarboxylic acid compositions were demonstrated to be sufficiently stable at neutral pH to have effective antimicrobial action (e.g., to disinfect) even though the peroxycarboxylic acid can degrade at neutral pH. For example, the present compositions were sufficiently stable to use for a day.

Example 8

Reduced Corrosion by Neutral or Alkaline Compositions of Medium Chain Peroxycarboxylic Acid Compositions according to the present invention were evaluated and demonstrated to exhibit significantly reduced corrosion at neutral and alkaline pH.

Materials and Methods

Composition KK (Table 26, Example 9) was used in this example. Composition KK was diluted with water to 4 or 8 wt-% of composition KK. The acid pH composition was tested. In addition, for others an alkaline composition (e.g., 50% NaOH) was added to bring the pH of the diluted composition to 6.

Results

The results of the corrosion tests are shown in Table 25. The present compositions at neutral pH exhibit radically reduced the corrosion of aluminum.

TABLE 25

Reduced Corrosion by Medium Chain Peroxycarboxylic Acid in Diluted Compositions at pH 6.

| | | Milli-inches per year (mpy) of corrosion | | |
|---|---|---|---|---|
| Composition | wt-% | aluminum | brass | 316 SS |
| Peroxyacetic Acid, pH 6.5 | 4.5 | 71.94 | 9.136 | 0.00628 |
| | 4.5 | 77.30 | 9.798 | −0.01245 |
| | 6.8 | 77.00 | 12.16 | 0.00942 |
| | 6.8 | 70.47 | 11.59 | 0.00624 |
| KK, acid pH | 0.95 | 62.90 | 6.911 | −0.00630 |
| | 0.95 | 57.80 | 7.049 | −0.00938 |
| KK, pH 6 | 4 | 7.005 | 11.92 | −0.00938 |
| | 4 | 7.117 | 11.66 | 0.00938 |
| | 8 | 10.93 | 17.77 | 0.00000 |
| | 8 | 9.905 | 17.61 | 0.01880 | mpy = (534,000 * (weight loss − control weight loss))/(Area * Time * Density)

Example 9

Compositions Including Medium Chain Peroxycarboxylic Acid and Solubilizer

Table 26 presents illustrative examples of the present compositions including medium chain peroxycarboxylic acid and anionic surfactant solubilizer. Quantities in the tables are in wt-%.

In each of compositions KK and BL-CB: the carrier was water; the oxidizing agent was hydrogen peroxide (supplied as 35% hydrogen peroxide in water); the stabilizing agent was HEDP (supplied as Dequest 2010, which includes 60 wt-% HEDP); and the solubilizer included 1-octane sulfonate (e.g., NAS-FAL).

The medium chain peroxycarboxylic acid and medium chain carboxylic acid were varied among these compositions. In each of compositions KK, BQ, and BR the medium chain peroxycarboxylic acid was peroxyoctanoic acid and the medium chain carboxylic acid was octanoic acid. In compositions BL and CB, the medium chain peroxycarboxylic acid was peroxyisononanoic acid and the medium chain carboxylic acid was isononanoic acid. In each of compositions BM, BN, BO, and BP the medium chain peroxycarboxylic acid was peroxynonanoic acid and the medium chain carboxylic acid was nonanoic acid. In each of compositions BS, BT, BU, and BV the medium chain peroxycarboxylic acid was peroxydecanoic acid and the medium chain carboxylic acid was decanoic acid.

The acidulant was varied among these compositions. In each of compositions KK, BL, BM, BO, BP, BQ, BR, BS, BT, BU, BV, BW, BX, BY, BX, CA, and CB the acidulant was phosphoric acid (supplied as 75% phosphoric acid). In composition BN the acidulant was methanesulfonic acid (supplied as 70% methanesulfonic acid). Composition BR included a reduced level of acidulant, and BQ an even further reduced level.

The solubilizer was varied among these compositions. In each of compositions KK, KK', BL, BM, BP, BQ, BR, BS, BW, BX, BY, BZ, CA, and CB the solubilizer was 1-octane sulfonate (e.g., NAS-FAL). In composition KK" the solubilizer included defoamer and was 1-octane sulfonate (4.2 wt-%) (e.g., NAS-FAL) plus C12-18 5EO butyl capped alcohol ethoxylate (1 wt-%) (supplied as Dehypon LT054, which includes 100% active). In composition BN the solubilizer included defoamer and was 1-octane sulfonate (2 wt-%) (NAS-FAL), cumene sulfonate (8 wt-%) plus C12-18 5EO butyl capped alcohol ethoxylate

TABLE 26

Examples of Compositions Including Anionic Surfactant Solubilizer

| Ingredient | KK | KK' | KK" | BL | BM | BN | BO | BP | BQ | BR |
|---|---|---|---|---|---|---|---|---|---|---|
| Medium Chain Peroxycarboxylic Acid | 1.3 | 0.94 | 0.8 | 0.8 | 1.4 | 1.7 | 3.6 | 3.3 | 3.4 | 0.64 |
| Medium Chain Carboxylic Acid | 2.6 | 2.7 | 3.0 | 3.0 | 2.8 | 2.5 | 7.9 | 3.7 | 3.7 | 3.2 |
| Solubilizer and optional defoamer | 4 | 4.3 | 5.2 | 7.9 | 4 | 11 | 4.6 | 6 | 6 | 4.0 |
| Carrier | 55 | 56 | 55 | 56 | 52 | 55 | 59 | 56 | 56 | 68 |
| Oxidizing Agent | 8.1 | 7.5 | 8.1 | 7.0 | 13 | 26 | 9.3 | 24 | 24 | 7.9 |
| Acidulant | 27 | 27 | 26 | 24 | 15 | 1.5 | 13 | 3.8 | 3.8 | 15 |
| Stabilizing Agent | 2 | 2 | 2 | 1.8 | 2.1 | 2.1 | 10 | 3 | 3 | 1.2 |

| Ingredient | BS | BT | BU | BV | BW | BX | BY | BZ | CA | CB |
|---|---|---|---|---|---|---|---|---|---|---|
| Medium Chain Peroxycarboxylic Acid | 1.3 | 1.3 | 1.8 | 1.9 | 1.5 | 2.7 | 5.1 | 5.0 | 4.4 | 1.2 |
| Medium Chain Carboxylic Acid | 2.5 | 2.5 | 1.9 | 1.8 | 2.1 | 3.3 | 1.9 | 2.1 | 2.6 | 2.6 |
| Solubilizer | 5.2 | 6.2 | 12 | 13 | 7 | 5.1 | 6 | 4.2 | 6 | 5.6 |
| Carrier | 57 | 57 | 60 | 60 | 60 | 56 | 46 | 44 | 47 | 53 |
| Oxidizing Agent | 8.1 | 8.3 | 19 | 20 | 26 | 24 | 34 | 33 | 37 | 8.6 |
| Acidulant | 24 | 24 | 3.2 | 3.2 | 2.1 | 3.8 | 3.8 | 9.8 | 1.9 | 27 |
| Stabilizing Agent | 2 | 2 | 2.5 | 2.5 | 2.1 | 4.9 | 3 | 3 | 1.5 | 2 |

(1 wt-%) (supplied as Dehypon LT054, which includes 100% active). In composition BO the solubilizer was 1-octane sulfonate (4.6 wt-%) (NAS-FAL) and secondary alkane sulfonate (secondary n-alkane (C13/C17) sulphonate sodium salt, sold, for example, under the trade name Hostapur SAS93, 60% active) (15 wt-%). In composition BT the solubilizer included defoamer and was 1-octane sulfonate (5.2 wt-%) (e.g., NAS-FAL) plus C12-18 5EO butyl capped alcohol ethoxylate (1 wt-%) (supplied as Dehypon LT054, which includes 100% active). In composition BU the solubilizer was 1-octane sulfonate (6 wt-%) (e.g., NAS-FAL) plus sodium xylene sulfonate (6 wt-%) (supplied as SXS, which includes 40% active). In composition BV the solubilizer included defoamer and was 1-octane sulfonate (5.6 wt-%) (e.g., NAS-FAL), sodium xylene sulfonate (6 wt-%) (supplied as SXS, which includes 40% active) plus C12-18 5EO butyl capped alcohol ethoxylate (1 wt-%) (supplied as Dehypon LT054, which includes 100% active).

The quantities of medium chain peroxycarboxylic acid were determined in compositions KK (current) and BL-BQ after 1-3 days at room temperature.

Example 10

Compositions Including Medium Chain Peroxycarboxylic Acid and Solubilizer

Tables 27-31 present illustrative examples of the present compositions including medium chain peroxycarboxylic acid and solubilizer. Quantities in the tables are in wt-%.

TABLE 27

Examples of Compositions Including Solvent Solubilizer

| Ingredient | A | B | C | D | E |
|---|---|---|---|---|---|
| Medium Chain Peroxycarboxylic Acid | 1.8 | 1.6 | 1.4 | 1.6 | 2.9 |
| Medium Chain Carboxylic Acid | 3.4 | 3.6 | 3.7 | 3.6 | 2.4 |
| Solubilizer | 60 | 40 | 60 | 60 | 40 |
| Carrier | 25 | 22 | 25 | 22 | 22 |
| Oxidizing Agent | 7.0 | 6.6 | 7.0 | 6.9 | 6.9 |
| Acidulant | 2 | 25 | 2 | 5 | 25 |
| Stabilizing Agent | 1.2 | 1.2 | 1.2 | 1.2 | 1.2 |

In each of compositions A-Q: the medium chain peroxycarboxylic acid was peroxyoctanoic acid; the medium chain carboxylic acid was octanoic acid; the carrier was water; the oxidizing agent was hydrogen peroxide (supplied from a 35% solution); and the stabilizing agent was HEDP (supplied as Dequest 2010 which includes 60 wt-% HEDP).

In each of compositions A-L, O, P, and Q: the acidulant was concentrated sulfuric acid. In compositions M and N, the acidulant was phosphoric acid (supplied as 85% and 75% phosphoric acid, respectively).

The solubilizer was varied among these compositions. In compositions A and B, the solubilizer was polyethyleneglycol 300. In compositions C, D, and E, the solubilizer was monomethyl ether of polyethyleneglycol (MPEG 550). In composition F, the solubilizer was nonionic surfactant, specifically Pluronic 17R4 an $(PO)_x(EO)_y(PO)_x$ reverse triblock copolymer with 40% EO and 60% PO. In composition G, the solubilizer was polyethyleneglycol 300 plus LAS acid (98% linear dodecylbenzene sulfonic acid). In composition H, the solubilizer was polyethyleneglycol 300 plus 1-octane sulfonate (supplied under the tradename NAS-FAL as 38% active). In composition I, the solubilizer was polyethyleneglycol 300 plus Dowfax Hydrotrope acid ($C_6$ alkylated diphenyl oxide disulfonic acid). In composition J, the solubilizer was dimethyl ether of polyethyleneglycol (PolyDME250) and LAS acid. In composition K, the solubilizer was dimethyl ether of polyethyleneglycol (PolyDME250) and NAS-FAL. In composition L, the solubilizer was dimethyl ether of polyethyleneglycol (PolyDME250) and Dowfax Hydrotrope acid. In compositions M, N, O and P, the solubilizer was dimethyl ether of polyethyleneglycol (PolyDME250) and NAS-FAL.

In composition Q, the solubilizer was dimethyl ether of polyethyleneglycol (PolyDME250) and NAS acid (supplied as 93% 1-octane sulfonic acid).

These compositions were made from a composition including 5 wt-% medium chain carboxylic acid.

In each of compositions R-Z: the medium chain peroxycarboxylic acid was peroxyoctanoic acid; the medium chain carboxylic acid was octanoic acid; the carrier was water; the oxidizing agent was hydrogen peroxide (supplied from a 35% solution); and the stabilizing agent was HEDP (supplied as Dequest 2010 which includes 60 wt-% HEDP). In compositions R and S, the acidulant was phosphoric acid (supplied as 75% phosphoric acid). In each of compositions T, U, and V, the acidulant was reagent grade, 98%, concentrated sulfuric acid (15 wt-%) and phosphoric acid (23 wt-%) (supplied as 75% phosphoric acid). In compositions W, X, Y, and Z, the acidulant was concentrated sulfuric acid (25 wt-%) and phosphoric acid (14 wt-%) (supplied as 75% phosphoric acid).

The solubilizer was varied among these compositions. In composition R, the solubilizer was 1-octane sulfonate (1.9 wt-%) and Tegotens EC-11 (a butoxy capped alcohol ethoxylate, a fast wetting surfactant) (15 wt-%). In compositions S, T, and W the solubilizer was Tegotens EC-11. In compositions U and Y, the solubilizer was Dehypon LS-54 $(R(EO)_5(PO)_4$, a fast wetting surfactant). In compositions V and Z, the solubilizer was Dehypon LT-104 (a butyl capped alcohol ethoxylate). In composition X, the solubilizer was LF-221 (a butoxy capped alcohol ethoxylate).

In each of compositions AA-VV: the medium chain peroxycarboxylic acid was peroxyoctanoic acid; the medium chain carboxylic acid was octanoic acid; the carrier was water; the oxidizing agent was hydrogen peroxide (supplied as 35% hydrogen peroxide in water); and the stabilizing agent was HEDP (supplied as Dequest 2010, which includes 60 wt-% HEDP).

In each of compositions AA, AA-O, DD, EE, GG, KK, LL, MM, NN, OO, PP, QQ, RR, SS, TT, UU, and VV the acidulant was phosphoric acid (supplied as 75% phosphoric acid). In composition BB, HH the acidulant was concentrated sulfuric acid (reagent grade, 98%). In composition CC, the acidulant was methane sulfonic acid (99.5%+Aldrich). In composition FF, the acidulant was nitric acid (supplied as 70% nitric acid). In composition II, the acidulant was concentrated sulfuric acid (technical grade, 93%). In composition JJ, the acidulant was sulfuric acid (supplied as 50% sulfuric acid).

The solubilizer was varied among these compositions. In compositions AA, AA-O, BB, CC, DD, FF, LL, HH, II, and JJ, the solubilizer was 1-octane sulfonate. In compositions EE and GG, the solubilizer was 1-octane sulfonate (3.8 wt-%) and Dehypon LS-54 (0.2 wt-%). In composition KK, the solubilizer was 1-octane sulfonate (NAS-FAL). In composition MM, the solubilizer was 1-octane sulfonate (3.8 wt-%) and Barlox 12 (dodecyldimethyl amine oxide, 30% active) (0.25 wt-%). In composition NN, the solubilizer was 1-octane sulfonate (3.8 wt-%) and Barlox 12 (0.5 wt-%). In composition OO, the solubilizer was 1-octane sulfonate (3.8 wt-%) and Barlox 12 (1 wt-%). In compositions PP, QQ, RR, and SS, the solubilizer was LAS-acid. In composition TT, the solubilizer was disodium cocoampho

TABLE 28

Examples of Compositions Including Solvent Solubilizer and Surfactant Solubilizer

| Ingredient | F | G | H | I | J | K | L | M | N | O | P | Q |
|---|---|---|---|---|---|---|---|---|---|---|---|---|
| Medium Chain Peroxycarboxylic Acid | 0.8 | 0.7 | 1.1 | 1.1 | 0.9 | 2.1 | 1.6 | 0.7 | 0.9 | 5.0 | not measured | 5.0 |
| Medium Chain Carboxylic Acid | 4.3 | 4.4 | 4.0 | 4.0 | 4.2 | 4.2 | 3.1 | 4.4 | 4.2 | 0.2 | <5 | 0.2 |
| Solvent Solubilizer | 0 | 40 | 40 | 40 | 42 | 44 | 42 | 34 | 29 | 28 | 28 | 28 |
| Surfactant Solubilizer | 45 | 5 | 2 | 5 | 8 | 6 | 7 | 6 | 4 | 6 | 6 | 10 |
| Carrier | 37 | 30 | 33 | 30 | 29 | 21 | 24 | 26 | 28 | 28 | 26 | 24 |
| Oxidizing Agent | 7.0 | 6.9 | 6.8 | 6.9 | 6.1 | 6.4 | 6.5 | 6.7 | 6.5 | 6.9 | 8.7 | 6.9 |
| Acidulant | 5 | 7 | 7 | 7 | 8 | 15 | 15 | 21 | 26 | 25 | 25 | 25 |
| Stabilizing Agent | 1.2 | 6 | 6 | 6 | 1.2 | 1.2 | 1.2 | 1.2 | 1.2 | 1.2 | 1.2 | 1.2 |

TABLE 29

Examples of Compositions Including Surfactant Solubilizer

| Ingredient | R | S | T | U | V | W | X | Y | Z |
|---|---|---|---|---|---|---|---|---|---|
| Medium Chain Peroxycarboxylic Acid | 0.5 | 0.4 | 1.0 | 1.0 | 0.7 | 3.8 | 3.7 | 3.8 | 3.5 |
| Medium Chain Carboxylic Acid | 4.6 | 4.6 | 3.1 | 3.1 | 3.4 | 2.6 | 2.7 | 2.6 | 2.9 |
| Surfactant Solubilizer | 17 | 20 | 20 | 20 | 20 | 20 | 20 | 20 | 20 |
| Carrier | 32 | 29 | 27 | 27 | 27 | 24 | 24 | 24 | 24 |
| Oxidizing Agent | 8.0 | 8.3 | 9.2 | 9.2 | 9.3 | 8.6 | 8.7 | 8.6 | 8.7 |
| Acidulant | 36 | 36 | 38 | 38 | 38 | 39 | 39 | 39 | 39 |
| Stabilizing Agent | 2.4 | 2.4 | 2.4 | 2.4 | 2.4 | 2.4 | 2.4 | 2.4 | 2.4 |

TABLE 30

Examples of Compositions Including Anionic Surfactant and/or Microemulsion Solubilizer

| Ingredient | AA | AA-O | BB | CC | DD | EE | FF | GG | HH | II | JJ | KK |
|---|---|---|---|---|---|---|---|---|---|---|---|---|
| Medium Chain Peroxycarboxylic Acid | 1.5 | 2.0 | 1.2 | 1.4 | 1.3 | 1.4 | 1.1 | 1.0 | 1.2 | 1.0 | 1.1 | 1.3 |
| Medium Chain Carboxylic Acid | 3.6 | 2.7 | 2.9 | 2.5 | 2.6 | 2.5 | 2.8 | 2.9 | 2.9 | 3.1 | 3.0 | 2.6 |
| Solubilizer | 8 | 5 | 5 | 9 | 4 | 4 | 6 | 4 | 5 | 5 | 5 | 4 |
| Carrier | 41 | 45 | 69 | 52 | 59 | 60 | 62 | 56 | 67 | 67 | 67 | 55 |
| Oxidizing Agent | 7.7 | 7.4 | 6.3 | 7.8 | 8.0 | 7.6 | 7.9 | 8.0 | 7.8 | 7.3 | 7.8 | 8.1 |
| Acidulant | 36 | 36 | 14 | 25 | 23 | 23 | 18 | 26 | 14 | 15 | 14 | 27 |
| Stabilizing Agent | 2.4 | 2.4 | 1.8 | 2.3 | 2.3 | 2.3 | 2.3 | 2.3 | 1.8 | 1.8 | 1.8 | 2.0 |

| Ingredient | LL | MM | NN | OO | PP | QQ | RR | SS | TT | UU | VV |
|---|---|---|---|---|---|---|---|---|---|---|---|
| Medium Chain Peroxycarboxylic Acid | 1.4 | 1.1 | 1.5 | not determined | 0.9 | 0.5 | 0.54 | 3.4 | 0.2 | 1.0 | 0.4 |
| Medium Chain Carboxylic Acid | 2.5 | 2.7 | 2.3 | <3.8 | 3.1 | 3.3 | 3.3 | 0.5 | 3.6 | 2.8 | 3.4 |
| Solubilizer | 4 | 4 | 4 | 5 | 1 | 2 | 4 | 10 | 6 | 10 | 22 |
| Carrier | 56 | 57 | 57 | 40-50 | 60 | 59 | 58 | 53 | 54 | 51 | 39 |
| Oxidizing Agent | 7.8 | 6.9 | 6.5 | <8 | 7.1 | 7.5 | 7.5 | 5.6 | 7.8 | 8.0 | 7.7 |
| Acidulant | 26 | 26 | 26 | 26 | 26 | 26 | 26 | 26 | 1.8 | 1.8 | 1.8 |
| Stabilizing Agent | 2.3 | 2.3 | 2.3 | 2.3 | 2.3 | 2.3 | 2.3 | 2.3 | 27 | 27 | 27 | dipropionate (supplied under the tradename Miranol® FBS, which includes 39% solids). In composition UU, the solubilizer was an aminoproprionate betaine (supplied under the tradename Mirataine® JC-HA, which includes 42% solids). In composition VV, the solubilizer C12-13 alcohol 4 mole EO carboxylic acid (supplied under the tradename Neodox 23-4, which includes 90% active).

The quantities of medium chain peroxycarboxylic acid were determined in compositions PP, QQ, RR, and SS after 7.5 days at 60° C.

In each of compositions WW, XX, YY, ZZ, and BA: the medium chain peroxycarboxylic acid was peroxyoctanoic acid; the medium chain carboxylic acid was octanoic acid; the carrier was water; the oxidizing agent was hydrogen peroxide (supplied as 35% hydrogen peroxide in water); the stabilizing agent was HEDP (supplied as Dequest 2010, which includes 60 wt-% HEDP); and the solubilizer was NAS-FAL.

The acidulant was varied among these compositions. In composition WW, the acidulant was hydroxyacetic acid (supplied as 75% hydroxyacetic acid) (19 wt-%) and sulfuric acid (reagent grade, 98%) (5 wt-%). In composition XX, the acidulant was hydroxyacetic acid (supplied as 75% hydroxyacetic acid) (19 wt-%) and methane sulfonic acid (99.5%+Aldrich) (5 wt-%). In composition YY, the acidulant was hydroxyacetic acid (supplied as 75% hydroxyacetic acid). In composition ZZ, the acidulant was purified hydroxyacetic acid. In composition BA, the acidulant was hydroxypropionic acid (supplied as 22% 3-hydroxypropionic acid).

In these compositions the hydroxycarboxylic acids contributed virtually no solubilization of the medium chain carboxylic acid. The compositions required solubilizer.

TABLE 31

Examples of Compositions Including Anionic Surfactant and/or Microemulsion Solubilizer plus Strong Organic Acidulant

| Ingredient | WW | XX | YY | ZZ | BA |
|---|---|---|---|---|---|
| Medium Chain Peroxycarboxylic Acid | 1.5 | 1.3 | 0.5 | 0.5 | 0.8 |
| Medium Chain Carboxylic Acid | 2.5 | 2.7 | 3.5 | 3.5 | 3.2 |
| Solubilizer | 4 | 4 | 4 | 4 | 4 |
| Carrier | 58 | 58 | 56 | 57 | 71 |
| Oxidizing Agent | 7.7 | 7.6 | 7.7 | 8.1 | 8.2 |
| Acidulant | 24 | 24 | 26 | 25 | 11 |
| Stabilizing Agent | 1.8 | 1.8 | 1.8 | 1.8 | 1.8 |

Making Exemplified Compositions

Table 32 shows the rapid generation of peroxyoctanoic acid achieved in making composition KK.

TABLE 32

Generation of Peroxyoctanoic Acid with Time at Room Temperature and at 120° F. (Composition KK)

| Minutes at RT | [POOA] wt-% | Minutes at 120° F. | [POOA] wt-% |
|---|---|---|---|
| 11 | 0.61 | 30 | 1.46 |
| 53 | 1.09 | 45 | 1.38 |
| 97 | 1.11 | 60 | 1.23 |
| 130 | 1.1 | 90 | 1.47 |
| 235 | 1.24 | 120 | 1.31 |
| 293 | 1.27 | | |
| 330 | 1.46 | | |
| 366 | 1.39 | | |
| 395 | 1.5 | | |

When a high level of sulfuric acid was used as the acidulant (Examples include B, E, O, and Q), a strong exotherm was obtained, and the medium chain peroxy carboxylic acid was generated rapidly, for example, virtually instantaneously. For some of these compositions, the sulfuric acid needed to be added slowly and with cooling to keep the temperature below 170° F. or below 120° F. Such formulas that can generate medium chain peroxy carboxylic acids, rapidly or almost instantaneously can be employed for on site generation at the use location.

The concentrations of peroxyoctanoic acid reported in the present examples were determined by a well established and standardized titration protocol. First, hydrogen peroxide content was determined by an oxidation-reduction titration with ceric sulfate. After the endpoint of this titration was reached, an excess of potassium iodide was added to the solution. The potassium iodide reacts with peroxycarboxylic acids to liberate iodine. The liberated iodine was titrated with a standard solution of sodium thiosulfate to yield the concentration of peroxycarboxylic acid. The remaining level of carboxylic acid can be calculated.

The octanoic acid employed in the present examples was obtained from sources including Procter & Gamble Chemicals and includes a minimum of 95% octanoic acid with minor amounts of hexanoic acid (ca. 2%), decanoic acid (ca. 2%), and dodecanoic acid (<0.5%).

Example 11

Shear Thinning Viscosity of Compositions Including Medium Chain Peroxycarboxylic Acid and Solubilizer Compositions according to the present invention were evaluated and demonstrated to have advantageous shear thinning viscosity, which is characteristic of microemulsions.

Materials and Methods

Several of the present medium chain peroxycarboxylic acid compositions were evaluated for viscosity as a function of rate of spindle rotation using an LVT viscometer and an N2 spindle. The temperature of the compositions was room temperature (about 75° F.).

Results

The results obtained for determinations of viscosity of the present compositions are reported below in Table 33. Decreasing viscosity with increasing spindle rotation rate indicates shear thinning, which is characteristic of a microemulsion. Each of the compositions tested showed shear thinning viscosity.

TABLE 33

Shear Thinning Viscosity of Composition LL

| rpm | Viscosity (cp) | rpm | Viscosity (cp) |
|---|---|---|---|
| 0.6 | 3875 | 2 | 2260 |
| 1.5 | 2600 | 2.5 | 1952 |
| 3 | 1700 | 4 | 1380 |
| 6 | 1300 | 5 | 1208 |
| 12 | 863 | 10 | 736 |
| 30 | 483 | 20 | 468 |
| 60 | 308 | 50 | 280 |
| | | 100 | 204 |

TABLE 34

Shear Thinning Viscosity of Composition HH

| rpm | Viscosity (cp) | rpm | Viscosity (cp) |
|---|---|---|---|
| 0.6 | 7000 | 2 | 3500 |
| 1.5 | 3500 | 2.5 | 2848 |
| 3 | 2200 | 4 | 1950 |
| 6 | 1500 | 5 | 1648 |
| 12 | 950 | 10 | 976 |
| 30 | 515 | 20 | 600 |
| 60 | 315 | 50 | 324 |
| | | 100 | 212 |

TABLE 35

Shear Thinning Viscosity of Composition KK

| rpm | Viscosity (cp) |
|---|---|
| 0.5 | 4080 |
| 1 | 3120 |

TABLE 35-continued

Shear Thinning Viscosity of Composition KK

| rpm | Viscosity (cp) |
|---|---|
| 2 | 2240 |
| 2.5 | 2016 |
| 4 | 1570 |
| 5 | 1344 |
| 10 | 820 |
| 20 | 520 |
| 50 | 320 |
| 100 | 218 |

Conclusions

The shear thinning viscosity of the present compositions is characteristic of a structured composition, such as a microemulsion.

Example 12

Compositions Including Medium Chain Peroxycarboxylic Acid and Solubilizer

Table 36 presents additional illustrative examples of the present compositions including medium chain peroxycarboxylic acid and solubilizer. Quantities in the tables are in wt-%.

In each of compositions AB-AQ: the medium chain peroxycarboxylic acid was peroxyoctanoic acid; the medium chain carboxylic acid was octanoic acid; the carrier was water; the oxidizing agent was hydrogen peroxide (supplied from a 35% solution); the stabilizing agent was HEDP (supplied as Dequest 2010 which includes 60 wt-% HEDP); and the acidulant was phosphoric acid (supplied as 75% phosphoric acid). Composition AC included fragrance (1 wt-%), specifically a mint apple fragrance.

The solubilizer was varied among these compositions. In each of compositions AB-AD, AH, AI, AN, the solubilizer was LAS acid. In compositions AE and AJ, the solubilizer was LAS acid plus C8 amine oxide. In composition AF, the solubilizer was LAS acid plus n-octyl amine. In composition AG, the solubilizer was LAS acid plus C8-dimethyl amine. In composition AK, the solubilizer was LAS acid plus alkylated diphenyl oxide disulfonate (acid form). In composition AL, the solubilizer was alkylated diphenyl oxide disulfonate (acid form). In composition AM, the solubilizer was LAS acid plus alkylated diphenyl oxide disulfonate (acid form) and C8 amine oxide. In composition AO, the solubilizer was sodium laureth sulfate; suitable sodium laureth sulfates tested include those with n=1 and 3. In composition AP, the solubilizer was alkylated diphenyl oxide disulfonate (salt form). In composition AQ, the solubilizer was alkylated diphenyl oxide disulfonate (salt form) plus NAS-FAL.

In each of compositions AR-AW: the carrier was water; the oxidizing agent was hydrogen peroxide (supplied from a 35% solution); the stabilizing agent was HEDP (supplied as Dequest 2010 which includes 60 wt-% HEDP); the acidulant was phosphoric acid (supplied as 75% phosphoric acid), and the solubilizer was LAS acid.

The medium chain peroxycarboxylic acid and medium chain carboxylic acid were varied among these compositions. In composition AR, the medium chain peroxycarboxylic acid was peroxynonanoic acid and the medium chain carboxylic acid was nonanoic acid (straight chain nonanoic acid). In compositions AS-AW, the medium chain peroxycarboxylic acid was peroxyoctanoic acid and peroxynonanoic acid and the medium chain carboxylic acid was octanoic acid and nonanoic acid; nonanoic acid (as isononanoic acid (which is believed to be a 6 carbon main chain with three pendant methyl groups)) was present at 0.5, 1, 0.1, 0.2, and 0.3 wt-% for AS-AW, respectively.

In each of compositions AX-AZ and BC-BF: the medium chain peroxycarboxylic acid was peroxyoctanoic acid; the medium chain carboxylic acid was octanoic acid; the carrier was water; the oxidizing agent was hydrogen peroxide (supplied from a 35% solution); the stabilizing agent was HEDP (supplied as Dequest 2010 which includes 60 wt-% HEDP); and the acidulant was phosphoric acid (supplied as 75% phosphoric acid).

The solubilizer was varied among these compositions. In composition AX, the solubilizer was LAS acid plus sodium lauryl sulfate. In composition AY, the solubilizer was LAS acid plus sodium lauryl sulfate and C8 dimethyl amine. In compositions AZ and BC-BF, the solubilizer was secondary alkane sulfonate (a mixture of sulfonated paraffins sold under the tradename Hostapur SAS).

TABLE 36

Examples of Compositions Including Surfactant Solubilizer (quantities in wt-%)

| Ingredient | AB | AC | AD | AE | AF | AG | AH | AI | AJ | AK | AL | AM | AN |
|---|---|---|---|---|---|---|---|---|---|---|---|---|---|
| Medium Chain Peroxycarboxylic Acid | 1.0 | 1.1 | 3.1 | 1.2 | 1.5 | 0.9 | 1.2 | 1.1 | nd | 0.9 | 0.9 | nd | 0.9 |
| Medium Chain Carboxylic Acid | 2.8 | 2.7 | 2.0 | 2.6 | 2.3 | 2.9 | 2.6 | 2.7 | <3.8 | 2.9 | 2.9 | <3.8 | 2.6 |
| Solubilizer | 7.8 | 9.7 | 11 | 8.2 | 7.9 | 7.9 | 7 | 6.5 | 8-12 | 5.7 | 6.3 | 8.6 | 7.8 |
| Carrier | 52 | 51 | 34 | 52 | 52 | 52 | 53 | 53 | 48-52 | 54 | 54 | 52 | 52 |
| Oxidizing Agent | 8.0 | 8.1 | 11 | 8.1 | 8.2 | 8.1 | 8.0 | 8.1 | 8 | 8.1 | 8.1 | 8 | 7.9 |
| Acidulant | 27 | 27 | 36 | 27 | 27 | 27 | 27 | 27 | 27 | 27 | 27 | 27 | 27 |
| Stabilizing Agent | 2.0 | 2.0 | 2.7 | 2.0 | 2.0 | 2.0 | 2.0 | 2.0 | 2.0 | 2.0 | 2.0 | 2.0 | 2.0 |

| Ingredient | AO | AP | AQ | AR | AS | AT | AU | AV | AW | AX | AY | AZ | BC |
|---|---|---|---|---|---|---|---|---|---|---|---|---|---|
| Medium Chain Peroxycarboxylic Acid | 1.0 | 0.9 | 0.9 | 1.0 | nd | nd | 1.0 | 1.0 | nd | nd | nd | 0.7 | 0.7 |
| Medium Chain Carboxylic Acid | 2.8 | 2.9 | 2.9 | 2.8 | <4.3 | <4.8 | 2.9 | 3.0 | <3.8 | <3.8 | <3.8 | 3.1 | 3.1 |
| Solubilizer | 8-9 | 4.5 | 4.3 | 7.8 | 7.8 | 7.8 | 7.8 | 7.8 | 8 | 8.3 | 8.6 | 7.4 | 7.8 |
| Carrier | 52 | 56 | 56 | 52 | 52 | 52 | 52 | 52 | 52 | 52 | 52 | 53 | 52 |
| Oxidizing Agent | 8.1 | 8.2 | 8.2 | 8.0 | 8 | 8 | 8.2 | 8.2 | 8 | 8 | 8 | 8.2 | 8.2 |

TABLE 36-continued

Examples of Compositions Including Surfactant Solubilizer (quantities in wt-%)

| Acidulant | 27 | 27 | 27 | 27 | 27 | 27 | 27 | 27 | 27 | 27 | 27 | 27 | 27 |
|---|---|---|---|---|---|---|---|---|---|---|---|---|---|
| Stabilizing Agent | 2.0 | 2.0 | 2.0 | 2.0 | 2.0 | 2.0 | 2.0 | 2.0 | 2.0 | 2.0 | 2.0 | 2.0 | 2.0 |

| Ingredient | BD | BE | BF | BG | BH | BI | BJ | BK |
|---|---|---|---|---|---|---|---|---|
| Medium Chain Peroxycarboxylic Acid | 1.0 | 1.0 | 1.0 | 0.9 | 0.9 | 1.0 | 1.0 | 1.1 |
| Medium Chain Carboxylic Acid | 2.8 | 2.8 | 2.9 | 2.9 | 2.9 | 2.8 | 2.8 | 2.7 |
| Solubilizer | 12 | 10 | 9 | 10 | 13 | 15 | 14 | 16 |
| Carrier | 48 | 50 | 51 | 50 | 47 | 45 | 46 | 44 |
| Oxidizing Agent | 7.8 | 8.2 | 7.6 | 8.3 | 8.3 | 8.3 | 8.2 | 8.1 |
| Acidulant | 27 | 27 | 27 | 14 | 14 | 14 | 14 | 14 |
| Stabilizing Agent | 2.0 | 2.0 | 2.0 | 2.0 | 2.0 | 2.0 | 2.0 | 2.0 |

In each of compositions BG-BK: the medium chain peroxycarboxylic acid was peroxyoctanoic acid; the medium chain carboxylic acid was octanoic acid; the carrier was water; the oxidizing agent was hydrogen peroxide (supplied from a 35% solution); the stabilizing agent was HEDP (supplied as Dequest 2010 which includes 60 wt-% HEDP); the solubilizer was secondary alkane sulfonate (a mixture of sulfonated paraffins sold under the tradename Hostapur SAS) plus NAS-FAL; and the acidulant was sulfuric acid.

The compositions that included LAS, secondary alkane sulfonate, alkylated diphenyl oxide disulfonate, or sodium lauryl sulfate as solubilizer were foaming compositions. Specifically, compositions AB and AC are foaming compositions Most of the compositions were phase stable. In particular: Compositions AX and AY were determined to be phase stable at 60° C. The phase stable compositions including anionic surfactant (e.g., foaming compositions) exhibited blue tyndall appearance and viscoelasticity. They were microemulsions. In fact, only the compositions for which the wt-% of medium chain peroxycarboxylic acid was not determined (nd) were not phase stable. That is, they separated into more than one phase after a predetermined time at one or more (e.g., at least one) of 40° F., room temperature, 100° F., or 140° F. (60° C.).

The concentrations of peroxyoctanoic acid reported in the present examples were determined by a well established and standardized titration protocol. First, hydrogen peroxide content was determined by an oxidation-reduction titration with potassium permanganate. After the endpoint of this titration was reached, an excess of potassium iodide was added to the solution. The potassium iodide reacts with peroxycarboxylic acids to liberate iodine. The liberated iodine was titrated with a standard solution of sodium thiosulfate to yield the concentration of peroxycarboxylic acid. The remaining level of carboxylic acid can be (and was) calculated.

The peroxycarboxylic acid was titrated at a time after formulation that was practical in the laboratory. For example, the peroxycarboxylic acid was titrated for compositions AB, AD, AE, AF, AG, AH, AK, AL, AO, AP, AQ, AU, AV, AZ, BC, and BD after the sample had sat at room temperature for 0, 2 (BD), or 3 (AP, AU, and AV) days. For example, the peroxycarboxylic acid was titrated for compositions AC and BG-BK after the sample had sat at 100° F. for 4 days (AC) or 7 days (BG-BK). For example, the peroxycarboxylic acid was titrated for compositions AI, AN, AR, BE and BF after the sample had sat at 140° F. (60° C.) for 1 day (AI, AR, and BE) or 4 days (AN and BF).

For composition AB, no decomposition of peroxycarboxylic acid was observed upon aging the composition for 7 days at 140° F. (60° C.). For composition AC, no decomposition of peroxycarboxylic acid was observed upon aging the composition for 34 days at 100° F. Other compositions were also observed to include stable peroxycarboxylic acid.

The octanoic acid employed in the present examples was obtained from sources including Procter & Gamble Chemicals and includes a minimum of 95% octanoic acid with minor amounts of hexanoic acid (ca. 2%), decanoic acid (ca. 2%), and dodecanoic acid (<0.5%).

Fragrance

Certain of the compositions were evaluated for phase stability and for smell after addition of a fragrance. In particular, compositions AB and AG were evaluated. Fragrances evaluated included Green Meadow (Klabin); Vinegar Mask I (J&E Sozio); Vinegar Mask II (J&E Sozio); amyl acetate; isobornyl acetate; and methyl salicylate.

Composition AC included fragrance (1 wt-%), specifically a mint apple fragrance which is believed to be or include an alkyl salicylate. Composition AC altered to include 10 wt-% LAS remained single phase at 40° F., room temperature, and 70° F.

Foaming

The results in Table 37 show that the present medium chain peroxycarboxylic acid composition produced foam with desirable qualities. This study employed a "FOAM IT" brand tank foamer set to produce slightly wet foam, 2 turns from the mid point. The foam was dispensed from use composition at 95-98° F. The foam was sprayed on a vertical stainless steel surface (approximately 15 ft by 15 ft) from a distance of about 10 ft. The results of Table 37 demonstrate that the present compositions provided foam with desirable hang time and density. Each of the compositions tested at 1 oz/6 gal. provided foam with desirable characteristics, such as the breaking foam was visible for about 5 min, the foam drained well from the vertical surface, exhibited good sheeting down vertical surface, and dried evenly to no visible residue.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

TABLE 37

Foaming by the Present Medium Chain Peroxycarboxylic Acid Compositions.

| Composition | Amount in Use Solution (oz/gal) | Break Time | Foam Dry Time (min) | Odor | Initial Appearance of Foam | Comments |
|---|---|---|---|---|---|---|
| AB | 0.17 | slow, about 2 min | >10 | moderate | Covers well, wet, about 1/16 inch thick | foam breaks to spotty foam, dries to no visible residue |
| AG | 0.17 | slow, about 2 min | >10 | moderate | Covers well, wet, about 1/16 inch thick | foam breaks to spotty foam, dries to no visible residue |
| AH | 0.17 | faster, <2 min | 95% dry at 10 min | moderate | Covers well, wetter than above | foam breaks to spotty foam, dries to no visible residue |
| AK | 0.17 | fast, about 1 min | 95% dry at 10 min | moderate | Wetter than above | no visible residue |
| AY | 0.17 | fast, about 10 sec | 95% dry at 10 min | strong | Very wet, lays flat | no visible residue |
| AB | 0.13 | fast, <1 min | about 10 min | low | Covers, wet | spotty foam |
| AG | 0.13 | fast, <1 min | about 10 min | low | Covers, wet | streaky foam |
| AH | 0.13 | very fast, <1 min | about 10 min | low | Extremely wet | very spotty foam |
| AK | 0.13 | very fast, <1 min | about 10 min | low | Extremely wet | very spotty foam |
| AY | 0.13 | fast, about 10 sec | 95% dry at 10 min | strong | Very wet, lays flat | no visible residue |

We claim:

1. A method of cleaning a soiled object comprising:
   contacting the object with a neutral or alkaline medium chain peroxycarboxylic acid composition, wherein the step of contacting comprises:
   contacting the object with an acid pH medium chain peroxycarboxylic acid composition consisting essentially of:
   a C8 to C10 peroxycarboxylic acid;
   a C8 to C10 carboxylic acid;
   one or more inorganic oxidizing agents;
   a stabilizing agent;
   a solubilizer; and
   an acidulant, wherein the composition is free of short chain peroxycarboxylic acids, and short chain carboxylic acids; and
   contacting the object with a source of alkalinity comprising an alkali metal hydroxide to form the neutral or alkaline medium chain peroxycarboxylic acid composition.

2. The method of claim 1, comprising:
   contacting the object with the acid pH medium chain peroxycarboxylic acid composition for a predetermined time; and
   after passage of the predetermined time, contacting the object with the source of alkalinity to form the neutral or alkaline medium chain peroxycarboxylic acid composition.

3. The method of claim 1, wherein the neutral or alkaline pH is about 6 to about 14.

4. The method of claim 1, wherein the neutral or alkaline pH is about 9 to about 12.

5. The method of claim 1, wherein the neutral or alkaline pH is about 6 to about 8.

6. The method of claim 1, wherein the neutral or alkaline pH is about 8 to about 14.

7. The method of claim 1, wherein the soiled object comprises pipes or vessels in a food processing plant, wares, laundry, an oven, a grill, or a floor, a carpet, a medical device, a membrane, or a combination thereof.

8. The method of claim 1, wherein the soiled object comprises heat transfer equipment.

9. The method of claim 1, wherein the acidulant is selected from the group consisting of sulfuric acid, nitric acid, hydrochloric acid, methane sulfonic acid, ethane sulfonic acid, propane sulfonic acid, butane sulfonic acid, xylene sulfonic acid, benzene sulfonic acid, and mixtures thereof.

10. The method of claim 1, wherein the acidulant comprises a carboxylic acid with $pK_a$ less than 4.

11. The method of claim 1, wherein the C8 to C10 percarboxylic acid is selected from the group consisting of peroxyoctanoic acid, peroxynonanoic acid, peroxyisononanoic acid, peroxydecanoic acid, and mixtures thereof.

12. The method of claim 1, wherein the acid pH medium chain peroxycarboxylic acid composition consists essentially of:
   about 0.3 to 7 wt % of the C8 to C10 peroxycarboxylic acid;
   about 1.0 to about 10 wt % of the C8 to C10 carboxylic acid;
   about 25 to about 65 wt % of the inorganic oxidizing agent;
   about 1.0 to about 10 wt % of the stabilizing agent;
   about 1 to about 20 wt % of the solubilizer; and
   about 2 to about 10 wt % of the acidulant.

\* \* \* \* \*